US008329916B2

(12) United States Patent
Amarasinghe et al.

(10) Patent No.: US 8,329,916 B2
(45) Date of Patent: *Dec. 11, 2012

(54) HUMAN PROTEIN TYROSINE PHOSPHATASE INHIBITORS AND METHOD OF USE

(75) Inventors: Kande K. D. Amarasinghe, Latham, NY (US); Cynthia Monesa Clark, Concord, MA (US); Ryan Matthew Nichols, Cincinnati, OH (US); Matthew B. Maier, Springboro, OH (US); Jeffrey Lyle Gray, Loveland, OH (US)

(73) Assignee: Aerpio Therapeutics Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/309,445

(22) Filed: Dec. 1, 2011

(65) Prior Publication Data

US 2012/0077975 A1    Mar. 29, 2012

Related U.S. Application Data

(60) Continuation of application No. 12/850,026, filed on Aug. 4, 2010, now Pat. No. 8,106,078, which is a division of application No. 11/821,846, filed on Jun. 26, 2007, now Pat. No. 7,795,444.

(60) Provisional application No. 60/816,730, filed on Jun. 27, 2006, provisional application No. 60/816,731, filed on Jun. 27, 2006, provisional application No. 60/816,825, filed on Jun. 27, 2006.

(51) Int. Cl.
*C07D 277/30* (2006.01)
*A61K 31/426* (2006.01)

(52) U.S. Cl. ....................................... 548/205; 514/365

(58) Field of Classification Search .................. 548/205; 514/365
See application file for complete search history.

(56) References Cited

U.S. PATENT DOCUMENTS

| 4,673,641 | A | 6/1987 | George et al. |
| 5,424,398 | A | 6/1995 | Middeldorp et al. |
| 5,585,089 | A | 12/1996 | Queen et al. |
| 5,688,781 | A | 11/1997 | Siegall et al. |
| 5,807,819 | A | 9/1998 | Cheng et al. |
| 5,994,128 | A | 11/1999 | Fallaux et al. |
| 6,033,908 | A | 3/2000 | Bout et al. |
| 6,342,219 | B1 | 1/2002 | Thorpe et al. |
| 6,589,758 | B1 | 7/2003 | Zhu |
| 6,596,772 | B1 | 7/2003 | Huang et al. |
| 7,226,755 | B1 | 6/2007 | Peters et al. |
| 7,507,568 | B2 | 3/2009 | Evdokimov |
| 7,588,924 | B2 | 9/2009 | Evdokimov et al. |
| 7,589,212 | B2 | 9/2009 | Gray et al. |
| 7,622,593 | B2 | 11/2009 | Gray et al. |
| 7,795,444 | B2 | 9/2010 | Gray et al. |
| 7,973,142 | B2 | 7/2011 | Rotello et al. |
| 8,188,125 | B2 | 5/2012 | Gray et al. |
| 2004/0167183 | A1 * | 8/2004 | Klopfenstein et al. ........ 514/357 |
| 2004/0204863 | A1 | 10/2004 | Kim et al. |
| 2007/0299116 | A1 | 12/2007 | Gray |
| 2008/0004267 | A1 | 1/2008 | Gray |
| 2008/0076764 | A1 | 3/2008 | Peters et al. |
| 2008/0108631 | A1 | 5/2008 | Gray et al. |
| 2009/0227639 | A1 | 9/2009 | Gray et al. |

FOREIGN PATENT DOCUMENTS

| WO | WO 00/65085 | 11/2000 |
| WO | WO 00/65088 | 11/2000 |
| WO | WO 02/26774 | 4/2002 |
| WO | WO 2011/005330 | 1/2011 |

OTHER PUBLICATIONS

Altschul et al., "Gapped BLAST and PSI-BLAST: A New Generation of Protein Database Search Programs," *Nucleic Acids Res.*, 25(27):3389-3402 (1997).
Annex et al., "Growth Factor-Induced Therapeutic Angiogenesis in the Heart: Protein Therapy," *Cardiovascular Research*, 65(3):649-655 (2005).
Ardelt et al., "Estradiol Regulates Angiopoietin-1 mRNA Expression Through Estrogen Receptor-α in a Rodent Experimental Stroke Model," *Stroke*, 36:337-341 (2005).
Auerbach et al., "Angiogenesis Assays: A Critical Overview," *Clinical Chemistry*, 49:32-40 (2003).
Barany et al., "Solid-phase Peptide Synthesis: A Silver Anniversary Report," *Int. J. Peptide Protein Res.*, 30(6):705-739 (1987).
Bartlett et al., "Molecular Recognition in Chemical and Biological Problems; Cavet: A Program to Facilitate the Structure-Derived Design of Biologically Active Molecules," *Special Pub., Royal Chem. Soc.*, 78:182-196 (1989).
Bohm, "The Computer Program LUDI: A New Method for the De Novo Design of Enzyme Inhibitors," *J. Comuter-Aided. Molec. Design*, 6(1):61-78 (1992).
Bussolino, et al., "Molecular mechanisms of blood vessel formation," *Trends Biochem Sci.* 22(7):251-256 (1997).
Carano et al., "Angiogenesis and Bone Repair," *Drug Discovery Today*, 8(21):980-989 (2003).
Carvalho et al., "The Role of Angiogenesis in a Murine Tibial Model of Distraction Osteogenesis," *Bone*, 34:849-861 (2004).
Chanteau et al., "Synthesis of Anthropomorphic Molecules: The NanoPutians," *J. Org. Chem.*, 68:8750-8766 (2003).
Cohen et al., "Molecular Modeling Software and Methods for Medicinal Chemistry," *J. Med. Chem.*, 33(3):883-894 (1990).
Daar, "Perspective: Emerging Resistance Profiles of Newly Approved Antiretroviral Drugs," *Topics in HIV Medicine*, 16(4):110-116 (2008).
Dean, "Recent Advances in Drug Design Methods: Where Will They Lead?" *BioEssays*, 16(9):683-687 (1994).

(Continued)

*Primary Examiner* — Robert Havlin
(74) *Attorney, Agent, or Firm* — Richard S. Echler

(57) ABSTRACT

The present disclosure relates to compounds effective as human protein tyrosine phosphatase beta (HPTP-β) inhibitors thereby regulating angiogenesis. The present disclosure further relates to compositions comprising said human protein tyrosine phosphatase beta (HPTP-β) inhibitors, and to methods for regulating angiogenesis.

20 Claims, No Drawings

OTHER PUBLICATIONS

Fachinger et al., "Functional Interaction of Vascular Endothelial-Protein-Tyrosine Phosphatase with the Angiopoietin Receptor Tie-2," *Oncogene*, 18:5948-5953 (1999).

Flower, "Modelling G-Protein-Coupled Receptors for Drug Design," *Biochimica et Biophysica Acta*, 1422:207-234 (1999).

Folkman, J., "Tumor angiogenesis," *The Molecular Basis of Cancer* (eds. Mendelsohn, J., Howley, P. M., Israel, M. A. & Liotta, L. A.) 206-232 (1995).

Gaits et al., "Increase in Receptor-like Protein Tyrosine Phosphatase Activity and Express Level on Density-Dependent Growth Arrest of Endothelial Cells," *Biochem J.*, 311:97-103 (1995).

Goodford, "A Computational Procedure for Determining Energetically Favorable Binding Sites on Biologically Important Macromolecules," *J. Med. Chem.*, 28(7):849-57 (1985).

Goodsell et al., "Automated Docking of Substrates to Proteins by Simulated Annealing," *Proteins Struct. Funct. Genet.* 8:195-202 (1990).

Harder et al., "Characterization and Kinetic Analysis of the Intracellular Domain of Human Protein Tyrosine Phosphatase β (HPTPβ) Using Synthetic Phosphopeptides," *Biochem. J.*, 296:395-401 (1994).

Henikoff et al., "Amino Acid Substitution Matrices from Protein Blocks," *Proc. Natl. Acad. Sci. USA* 89:10915-10919 (1992).

Hopkins et al., "Inhibitors of Kinesin Activity from Structure-Based Computer Screening," *Biochemistry*, 39:2805-2814 (2000).

Huang et al., "HCPTPA, a Protein Tyrosine Phosphatase that Regulates Vascular Endothelial Growth Factor Receptor-Mediated Signal Transduction and Biological Activity," *J. Biol. Chem.*, 53:38183-38188 (1999).

Itoh et al., "Purification and Characterization of the Catalytic Domains of the Human Receptor-Linked Protein Tyrosine Phosphatases HPTPβ, Leukocyte Common Antigen (LCA), and Leukocyte Common Antigen-Related Molecule (LAR)," *Journal of Biological Chemistry*, 267(17):12356-12363 (1992).

Jones et al., "Development and Validation of a Genetic Algorithm for Flexible Docking," *J Mol. Biol.*, 267:727-748 (1997).

Jones et al., "Molecular Recognition of Receptor Sites Using a Genetic Algorithm with a Description of Desolvation," *J. Mol. Biol.*, 245:43-53 (1995).

Keen, "Radioligand Binding Methods for Membrane Preparations and Intact cells," *Methods in Molecular Biology*, 83:*Receptor Signal Transduction Protocols*, edited Humana Press Inc., Totoway N.J. (1997).

Köhler et al., "Continuous Cultures of Fused Cells Secreting Antibody of Predefined Specificity," *Biotechnology*, 24:524-526 (1992).

Krueger et al., "Structural Diversity and evolution of Human Receptor-Like Protein Tyrosine Phosphatases," *The EMBO Journal*, 9(10):3241-3252 (1990).

Kugathasan et al., "Role of Angiopoietin-1 in Experimental and Human Pulmonary Arterial Hpertension," *Chest*, 128:633-642 (2005).

Kuntz et al., "A Geometric Approach to Macromolecule-Ligand Interactions," *J. Mol. Biol.* 161:269-288 (1982).

Lin et al., "Inhibition of Tumor Angiogenesis Using a Soluble Receptor Establishes a Role for Tie2 in Pathologic Vascular Growth," *J. Clinical Invest.*,100(8):2072-2078 (1997).

Ma et al., "RNase Protection Assay," *Methods*, 10(3):273-8 (1996).

Martin, "3D Database Searching in Drug Design," *J. of Medicinal Chemistry*, 35(12):2145-2154 (1992).

Meadows, "Keeping Up with Drug Safety Information," 2006: *FDA Consumer Magazine*: http://www.fda.gov/fdac/features/2006/306_drugsafety.html, accessed Mar. 17, 2008.

Merrifield, "Solid Phase Peptide Synthesism. I. The Synthesis of a Tetrapeptide," *J. Am. Chem. Soc.*, 85:2149-2154 (1963).

Miranker et al., "Functionality Maps of Binding Sites: A Multiple Copy Simultaneous Search Method," *Proteins: Struc. Func. and Genectics,* 11(1):29-34 (1991).

Navaza, "AMoRe: An Automated Package for Molecular Replacement," *J. Acta Cryst.* A50:157-163 (1994).

Nguyen et al., "Cellular Interactions in Vascular Growth and Differentiation," *Int. Rev. Cytol.*, 204:1-48 (2001).

Nishibata et al., "Automatic Creation of Drug Candidate Structures Based on Receptor Structure. Starting Point for Artificial Lead Generation," *Tetrahedron*, 47(43):8985-8990 (1991).

O'Reilly, "Angiostatin: a novel angiogenesis inhibitor that mediates the suppression of metastases by a Lewis lung carcinoma," *Cell*, 79(2):315-28 (1994).

O'Reilly, "Endostatin: an endogenous inhibitor of angiogenesis and tumor growth," *Cell*, 88(2):277-85 (1997).

Rarey et al., "A Fast Flexible Docking Method Using an Incremental Construction Algorithm," *J. Mol. Biol.*, 261:470-489 (1996).

Riechmann et al., "Reshaping Human Antibodies for Therapy," *Nature*, 332:323-327 (1988).

Saliba, "Heparin in the Treatment of Burns: A Review," May 2001; Burn 27(4):349-358; full text edition, pp. 1-16.

Schöneberg et al., "Structural basis of G protein-coupled receptor function," *Molecular and Cellular Endocrinology*, 151:181-193 (1999).

Sexton, "Recent advances in our understanding of peptide hormone receptors and RAMPS," *Current Opinion in Drug Discovery and Development*, 2(5):440-448 (1999).

Shiojima et al., "Disruption of Coordinated Cardiac Hypertrophy and Angiogenesis Contributes to the Transition to Heart Failure," *Journal of Clinical Invest.*, 115(8):2108-2118 (2005).

Shoichet et al., "Lead Discovery Using Molecular Docking," *Chem. Biology*, 6:439-446 (2002).

Siddiqui et al., "Combination of angiopoietin-1 and vascular endothelial growth factor gene therapy enhances arteriogenesis in the ischemic myocardium," *Biochem. Biophys. Res. Comm.*, 310:1002-1009 (2003).

Simons, "Angiogenesis: Where Do We Stand Now?," *Circulation*, 111:1556-1566 (2005).

Simons et al., "Clinical Trials in Coronary Angiogenesis," *Circulation*, 102:73-86 (2000).

Stal et al., "Detailed Analysis of Scoring Functions for Virtual Screening," *J. Med. Chem.*, 44:1035-1042 (2001).

Stetler-Stevenson, "The Role of Matrix Metalloproteinases in Tumor Invasion, Metastasis, and Angiogenesis," *Surg. Oncol. Clin. N. Am.*, 10(2):383-392 (2001).

Suggitt et al., "50 Years of Preclinical Anticancer Drug Screening: Empirical to Target-Drive Approaches," *Clinical Cancer Research*, 11:971-981 (2005).

Suri et al., "Increased Vascularization in Mice Overexpressing Angiopoietin-1," *Science*, 282:468-471 (1998).

Takahashi et al.,"Adenoviral-Delivered Angiopoietin-1 Reduces the Infarction and Attenuates the Progression of Cardiace Dysfunction in the Rate Model of Acute Myocardial Infarction," *Molecular Therapy*, 8(4):584-592 (2003).

Teischer, "Potentiation of cytotoxic cancer therapies by TNP-470 alone and with other anti-angiogenic agents," *Int. J. Cancer*, 57(6)920-925 (1994).

Thurston, "Complimentary Actions of VEGF and Angiopoietin-1 on Blood Vessel Growth and Leakage," *J. Anat.*, 200:575-580 (2002).

Thurston et al., "Angiopoietin-1 Protects the Adult Vasculature Against Plasma Leakage," *Nature Medicine*, 6(4):460-463 (2000).

Vailhe et al., "In Vitro Models of Vasculogenesis and Angiogenesis," *Laboratory Investigation*, 81:439-452 (2001).

Wang et al., "Expressions and Characterization of Wild Type, Truncated, and Mutant Forms of the Intracellular Region of the Receptor-Like Protein Tyrosine Phosphatase HPTPβ," *J. of Bio. Chem.*, 267(23):16696-16702 (1992).

Weidner, "Tumor Angiogenesis and Metastasis Correlation in Invasive Breast Carcinoma," *New Eng. J. Med.*, 324(1):108 (1991).

Whitaker et al., "Vascular Endothelial Growth Factor Receptor-2 and Neuropilin-1 Form a Receptor Complex That is Responsible for the Differential Signaling Potency of VEGF$_{165}$ and VEGF$_{121}$," *Journal of Biological Chemistry*, 276(27):25520-25531 (2001).

Wright et al., "Protein-Tyrosine Phosphatases in the Vessel Wall Differential Expression After Actue Arterial Injury," *Arterioscler Thromb. Vasc.*, 1189-1198 (2000).

Yancopoulos et al., "Vascular-Specific Growth Factors and Blood Vessel Formation," *Nature*, 407(6801):242-248 (2000).

Zhang et al., "Vascular Endothelial Growth Factor and Angiopoietins in Focal Cerebral Ischemia," *Trends Cardiovascular Med.*, 12(2):62-66 (2002).

Collaborative Computational Project, No. 4, "The CCP4 Suite: Programs for Protein Crystallography," *Acta Cryst.*, D50:760-763 (1994).

* cited by examiner

HUMAN PROTEIN TYROSINE PHOSPHATASE INHIBITORS AND METHOD OF USE

PRIORITY

This application is a Continuation Application of U.S. application Ser. No. 12/850,026, filed Aug. 4, 2010 now U.S. Pat. No. 8,106,078, which is a Divisional Application of U.S. application Ser. No. 11/821,846, filed on Jun. 26, 2007, now U.S. Pat. No. 7,795,444, which claims the benefit of U.S. Provisional Applications Ser. Nos. 60/816,730, 60/816,731, and 60/816,825 all of which were filed on Jun. 27, 2006 and the entire disclosures of each of U.S. Provisional Applications Ser. Nos. 60/816,730, 60/816,731, and 60/816,825 and U.S. application Ser. Nos. 12/850,026 and 11/821,846, are all incorporated herein by reference in their entirety.

FIELD

The present disclosure relates to compounds effective as human protein tyrosine phosphatase beta (HPTP-β) inhibitors thereby regulating angiogenesis. The present disclosure further relates to compositions comprising one or more human protein tyrosine phosphatase beta (HPTP-β) inhibitors, and to methods for regulating angiogenesis.

BACKGROUND

Angiogenesis, the sprouting of new blood vessels from the pre-existing vasculature, plays a crucial role in a wide range of physiological and pathological processes (Nguyen, L. L. et al., *Int. Rev. Cytol.*, 204, 1-48, (2001)). Angiogenesis is a complex process, mediated by communication between the endothelial cells that line blood vessels and their surrounding environment. In the early stages of angiogenesis, tissue or tumor cells produce and secrete pro-angiogenic growth factors in response to environmental stimuli such as hypoxia. These factors diffuse to nearby endothelial cells and stimulate receptors that lead to the production and secretion of proteases that degrade the surrounding extracellular matrix. The activated endothelial cells begin to migrate and proliferate into the surrounding tissue toward the source of these growth factors (Bussolino, F., *Trends Biochem. Sci.*, 22, 251-256, (1997)). Endothelial cells then stop proliferating and differentiate into tubular structures, which is the first step in the formation of stable, mature blood vessels. Subsequently, periendothelial cells, such as pericytes and smooth muscle cells, are recruited to the newly formed vessel in a further step toward vessel maturation.

Angiogenesis is regulated by a balance of naturally occurring pro- and anti-angiogenic factors. Vascular endothelial growth factor, fibroblast growth factor, and angiopoeitin represent a few of the many potential pro-angiogenic growth factors. These ligands bind to their respective receptor tyrosine kinases on the endothelial cell surface and transduce signals that promote cell migration and proliferation. Whereas many regulatory factors have been identified, the molecular mechanisms of this process are still not fully understood.

There are many disease states driven by persistent unregulated or improperly regulated angiogenesis. In such disease states, unregulated or improperly regulated angiogenesis may either cause a particular disease or exacerbate an existing pathological condition. For example, ocular neovascularization has been implicated as the most common cause of blindness and underlies the pathology of approximately 20 eye diseases. In certain previously existing conditions such as arthritis, newly formed capillary blood vessels invade the joints and destroy cartilage. In diabetes, new capillaries formed in the retina invade the vitreous humor, causing bleeding and blindness. Both the growth and metastasis of solid tumors are also angiogenesis-dependent (Folkman et al., "Tumor Angiogenesis," Chapter 10, 206-32, in The Molecular Basis of Cancer, Mendelsohn et al., eds., W.B. Saunders, (1995)). It has been shown that tumors which enlarge to greater than 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, *New Eng. J. Med.*, 324, 1, 1-8 (1991)). When used as drugs in tumor-bearing animals, natural inhibitors of angiogenesis may prevent the growth of small tumors (O'Reilly et al., *Cell*, 79, 315-28 (1994)). In some protocols, the application of such inhibitors leads to tumor regression and dormancy even after cessation of treatment (O'Reilly et al., *Cell*, 88, 277-85 (1997)). Moreover, supplying inhibitors of angiogenesis to certain tumors may potentiate their response to other therapeutic regimens (Teischer et al., *Int. J. Cancer*, 57, 920-25 (1994)).

Although many disease states are driven by persistent unregulated or improperly regulated angiogenesis, some disease states could be treated by increased angiogenesis. Tissue growth and repair are biologic events wherein cellular proliferation and angiogenesis occur. Thus an important aspect of wound repair is the revascularization of damaged tissue by angiogenesis.

Chronic, non-healing wounds are a major cause of prolonged morbidity in the aged human population. This is especially the case in bedridden or diabetic patients who develop severe, non-healing skin ulcers. In many of these cases, the delay in healing is a result of inadequate blood supply either as a result of continuous pressure or of vascular blockage. Poor capillary circulation due to small artery atherosclerosis or venous stasis contributes to the failure to repair damaged tissue. Such tissues are often infected with microorganisms that proliferate unchallenged by the innate defense systems of the body which require well vascularized tissue to effectively eliminate pathogenic organisms. As a result, most therapeutic intervention centers on restoring blood flow to ischemic tissues thereby allowing nutrients and immunological factors access to the site of the wound.

Atherosclerotic lesions in large vessels may cause tissue ischemia that could be ameliorated by modulating blood vessel growth to the affected tissue. For example, atherosclerotic lesions in the coronary arteries may cause angina and myocardial infarction that could be prevented if one could restore blood flow by stimulating the growth of collateral arteries. Similarly, atherosclerotic lesions in the large arteries that supply the legs may cause ischemia in the skeletal muscle that limits mobility and in some cases necessitates amputation, which may also be prevented by improving blood flow with angiogenic therapy.

Other diseases such as diabetes and hypertension are characterized by a decrease in the number and density of small blood vessels such as arterioles and capillaries. These small blood vessels are important for the delivery of oxygen and nutrients. A decrease in the number and density of these vessels contributes to the adverse consequences of hypertension and diabetes including claudication, ischemic ulcers, accelerated hypertension, and renal failure. These common disorders and many other less common ailments, such as Burgers disease, could be ameliorated by increasing the number and density of small blood vessels using angiogenic therapy.

It has been suggested that one means for regulating angiogenesis is to treat patients with a human protein tyrosine phosphatase beta (HPTP-β) inhibitor (Kruegar et al., *EMBO J.*, 9, (1990)) and, therefore, to satisfy this need the compounds of the present disclosure have been prepared.

SUMMARY

The present disclosure relates to compounds having Formula (I) as shown below:

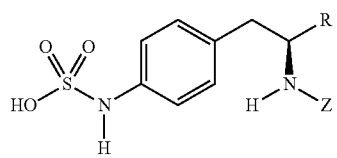

(I)

or pharmaceutically acceptable salts thereof, wherein the R and Z groups can be defined by any of the various alternative descriptions offered below. The compounds of Formula (I), and/or their pharmaceutically acceptable salts have been found to be inhibitors of human protein tyrosine phosphatase beta (HPTP-β), and hence are capable of regulating angiogenesis in humans, so as to treat various diseases that include but are not limited to diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma and post-laser complications, diseases associated with rubeosis, and proliferative vitreoretinopathy, Crohn's disease and ulcerative colitis, psoriasis, sarcoidosis, rheumatoid arthritis, hemangiomas, Osler-Weber-Rendu disease, hereditary hemorrhagic telangiectasia, solid or blood borne tumors and acquired immune deficiency syndrome, skeletal muscle and myocardial ischemia, stroke, coronary artery disease, peripheral vascular disease, and coronary artery disease.

The present disclosure further relates to pharmaceutical compositions comprising one or more of the compounds of Formula (I), and pharmaceutically acceptable salts thereof.

The present disclosure also relates to methods for controlling angiogenesis, and thereby providing a treatment for diseases affected by angiogenesis, said methods comprising administering to a human an effective amount of one or more compounds having Formula (I), and pharmaceutically acceptable salts thereof, as disclosed herein.

These and other objects, features, and advantages will become apparent to those of ordinary skill in the art from a reading of the following detailed description and the appended claims. All documents cited are in relevant part, incorporated herein by reference; the citation of any document is not to be construed as an admission that it is prior art with respect to the present disclosure.

DETAILED DESCRIPTION

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

An organic unit can have, for example, 1-26 carbon atoms, 1-18 carbon atoms, 1-12 carbon atoms, 1-8 carbon atoms, or 1-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like.

Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Substituted and unsubstituted linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 2,2,2-trifluoroethyl ($C_3$), 3-carboxypropyl ($C_3$), 2,3-dihydroxycyclobutyl ($C_4$), and the like.

Substituted and unsubstituted linear, branched, or cyclic alkenyl include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

Substituted and unsubstituted linear or branched alkynyl include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

The term "aryl" as used herein denotes organic rings that consist only of a conjugated planar carbon ring system with delocalized pi electrons, non-limiting examples of which include phenyl ($C_6$), naphthylen-1-yl ($C_{10}$), naphthylen-2-yl ($C_{10}$). Aryl rings can have one or more hydrogen atoms substituted by another organic or inorganic radical. Non-limiting examples of substituted aryl rings include: 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$).

The term "heteroaryl" denotes an aromatic ring system having from 5 to 10 atoms. The rings can be a single ring, for example, a ring having 5 or 6 atoms wherein at least one ring atom is a heteroatom not limited to nitrogen, oxygen, or sulfur. Or "heteroaryl" can denote a fused ring system having 8 to 10 atoms wherein at least one of the rings is an aromatic ring and at least one atom of the aromatic ring is a heteroatom not limited nitrogen, oxygen, or sulfur.

The following are non-limiting examples of heteroaryl rings according to the present disclosure:

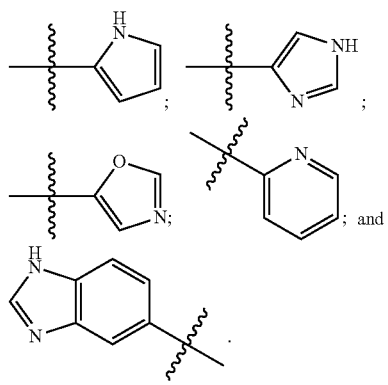

The term "heterocyclic" denotes a ring system having from 3 to 10 atoms wherein at least one of the ring atoms is a heteroatom not limited to nitrogen, oxygen, or sulfur. The rings can be single rings, fused rings, or bicyclic rings. Non-limiting examples of heterocyclic rings include:

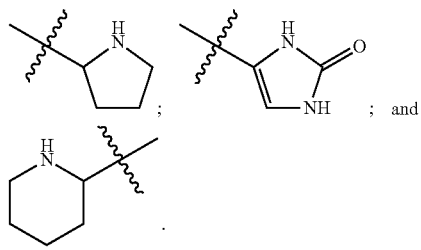

All of the aforementioned heteroaryl or heterocyclic rings can be optionally substituted with one or more substitutes for hydrogen as described herein further.

Throughout the description of the present disclosure the terms having the spelling "thiophene-2-yl and thiophene-3-yl" are used to describe the heteroaryl units having the respective formulae:

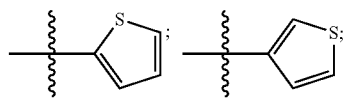

whereas in naming the compounds of the present disclosure, the chemical nomenclature for these moieties are typically spelled "thiophen-2-yl and thiophen-3-yl" respectively. Herein the terms "thiophene-2-yl and thiophene-3-yl" are used when describing these rings as units or moieties which make up the compounds of the present disclosure solely to make it unambiguous to the artisan of ordinary skill which rings are referred to herein.

The term "substituted" is used throughout the specification. The term "substituted" is defined herein as "a hydrocarbyl moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. A three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

The following are non-limiting examples of units that can substitute for hydrogen atoms on a unit:

i) $C_1$-$C_{12}$ linear, branched, or cyclic alkyl, alkenyl, and alkynyl; for example, methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_1$-$C_9$ heterocyclic rings; as described herein below;

iv) substituted or unsubstituted $C_1$-$C_9$ heteroaryl rings; as described herein below;

v) —$(CR^{14a}R^{14b})_zOR^{13}$; or example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vi) —$(CR^{14a}R^{14b})_zC(O)R^{13}$; for example, —$COCH_3$, —$CH_2COCH_3$, —$OCH_2CH_3$, —$CH_2COCH_2CH_3$, —$COCH_2CH_2CH_3$, and —$CH_2COCH_2CH_2CH_3$;

vii) —$(CR^{14a}R^{14b})_zC(O)OR^{13}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

viii) —$(CR^{14a}R^{14b})_zC(O)N(R^{13})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

ix) —$(CR^{14a}R^{14b})_zN(R^{13})_2$; for example, —$NH_2$, —$CH_2NH_2$, —$NHCH_3$, —$N(CH_3)_2$, —$NH(CH_2CH_3)$, —$CH_2NHCH_3$, —$CH_2N(CH_3)_2$, and —$CH_2NH(CH_2CH_3)$;

x) halogen; —F, —Cl, —Br, and —I;

xi) —$(CR^{14a}R^{14b})_zCN$;

xii) —$(CR^{14a}R^{14b})_zNO_2$;

xiii) —$CH_jX_k$; wherein X is halogen, j is from 0 to 2, j+k=3; for example, —$CH_2F$, —$CHF_2$, —$CF_3$, —$CCl_3$, or —$CBr_3$;

xiv) —$(CR^{14a}R^{14b})_zSR^{13}$; —SH, —$CH_2SH$, —$SCH_3$, —$CH_2SCH_3$, —$SC_6H_5$, and —$CH_2SC_6H_5$;

xv) —$(CR^{14a}R^{14b})_zSO_2R^{13}$; —$SO_2H$, —$CH_2SO_2H$, —$SO_2CH_3$, —$CH_2SO_2CH_3$, —$SO_2C_6H_5$, and —$CH_2SO_2C_6H_5$; and xiii) —$(CR^{14a}R^{14b})_zSO_3R^{13}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{13}$ is independently hydrogen, substituted or unsubstituted $C_1$-$C_4$ linear, branched, or cyclic alkyl, phenyl, benzyl; or two $R^{13}$ units can be taken together to form a ring comprising 3-7 atoms; $R^{14a}$ and $R^{14b}$ are each independently hydrogen or $C_1$-$C_4$ linear or branched alkyl; the index p is from 0 to 4.

The present disclosure addresses several unmet medical needs, inter alia;

1) Providing compositions effective as human protein tyrosine phosphatase beta (HPTP-β) inhibitors; and thereby providing a method for regulating angiogenesis in a disorder, disease, malady, or condition wherein angiogenesis is elevated;

2) Providing compositions effective as human protein tyrosine phosphatase beta (HPTP-β) inhibitors; and thereby providing a method for regulating angiogenesis in a disorder, disease, malady, or condition; and 3) Providing compositions effective as human protein tyrosine phosphatase beta (HPTP-β) inhibitors; and thereby providing a method for regulating angiogenesis in a disorder, disease, malady, or condition wherein angiogenesis is decreased.

These and other unmet medical needs are resolved by the human protein tyrosine phosphatase beta (HPTP-β) inhibitors of the present disclosure, that are capable of regulating angiogenesis and thereby serving as a method for treating elevated or diminished angiogenesis in humans or in treating diseases that are caused by insufficient regulation of human protein tyrosine phosphatase beta (HPTP-β).

The compounds disclosed herein include all pharmaceutically acceptable salt forms, for example, salts of both basic groups, inter alia, amines, as well as salts of acidic groups, inter alia, sulfamic acids, and carboxylic acids. The following are non-limiting examples of anions that can form salts with basic groups, such as amines: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups, such as carboxylic acid/carboxylate units: sodium, lithium, potassium, calcium, magnesium, bismuth, and the like.

The compounds of the present disclosure are ethyl-amino substituted phenylsulfamic acids, or their pharmaceutically acceptable salts, having the core structure of Compound (I) shown in the drawing below:

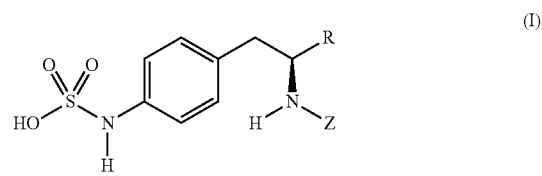

wherein the units R and Z can be any of the alternatives further defined and exemplified herein below. In such compounds of Formula (I), the carbon atom bearing the amino unit has the absolute stereochemistry (S) stereochemistry as indicated in the drawing above, which typically corresponds to an (S) configuration at the same amine-bearing carbon atom, but which could vary depending on the nature of the R substituent group and the resulting priority changes.

R Units

In some embodiments, the R units of the compounds of Formula (I) can be substituted or unsubstituted heterocyclic or heteroaryl rings having from 3 to 15 ring atoms. The heterocyclic or heteroaryl rings can be represented below by the generic ring, A, in the formula:

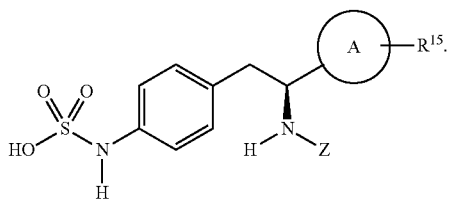

Examples of the heterocyclic or heteroaryl "A" rings include the ring structures

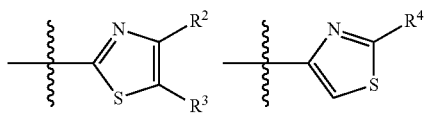

These heterocyclic or heteroaryl rings can be substituted by one or more independently chosen substituents represented in the generic formula by $R^{15}$ units. Non-limiting examples of $R^{15}$ units include:

i) linear, branched, or cyclic alkyl, alkenyl, and alkynyl; for example, methyl ($C_1$), ethyl ($C_2$), n-propyl ($C_3$), iso-propyl ($C_3$), cyclopropyl ($C_3$), propylen-2-yl ($C_3$), propargyl ($C_3$), n-butyl ($C_4$), iso-butyl ($C_4$), sec-butyl ($C_4$), tert-butyl ($C_4$), cyclobutyl ($C_4$), n-pentyl ($C_5$), cyclopentyl ($C_5$), n-hexyl ($C_6$), and cyclohexyl ($C_6$);

ii) substituted or unsubstituted aryl; for example, phenyl, 2-fluorophenyl, 3-chlorophenyl, 4-methylphenyl, 2-aminophenyl, 3-hydroxyphenyl, 4-trifluoromethylphenyl, and biphenyl-4-yl;

iii) substituted or unsubstituted heterocyclic; examples of which are provided herein below;

iv) substituted or unsubstituted heteroaryl; examples of which are provided herein below;

v) —$(CR^{17a}R^{17b})_q OR^{16}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vi) —$(CR^{17a}R^{17b})_q C(O)OR^{16}$; (for example, —$COCH_3$, —$CH_2COCH_3$, —$OCH_2CH_3$, —$CH_2COCH_2CH_3$, —$COCH_2CH_3$, and —$CH_2COCH_2CH_3$;

vii) —$(CR^{17a}R^{17b})_q C(O)OR^{16}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

viii) —$(CR^{17a}R^{17b})_q C(O)N(R^{16})_2$; for example, —$CONH_2$, —$CH_2CONH_2$, $CONHCH_3$, —$CH_2CONHCH_3$, —$CON(CH_3)_2$, and —$CH_2CON(CH_3)_2$;

ix) —$(CR^{17a}R^{17b})_q OC(O)N(R^{16})_2$; for example, —$OC(O)NH_2$, —$CH_2OC(O)NH_2$, —$OC(O)NHCH_3$, —$CH_2OC(O)NHCH_3$, —$OC(O)N(CH_3)_2$, and —$CH_2OC(O)N(CH_3)_2$;

x) —$(CR^{17a}R^{17b})_q N(R^{16})_2$; for example, —$NH_2$, —$CH_2NH_2$, —$NHCH_3$, —$N(CH_3)_2$, —$NH(CH_2CH_3)$, —$CH_2NHCH_3$, —$CH_2N(CH_3)_2$, and —$CH_2NH(CH_2CH_3)$;

xi) halogen: —F, —Cl, —Br, and —I;

xii) —$CH_mX_n$; wherein X is halogen, m is from 0 to 2, m+n=3; for example, —$CH_2F$, —$CHF_2$, —$CF_3$, —$CCl_3$, or —$CBr_3$;

xiii) —$(CR^{17a}R^{17b})_q CN$; for example; —CN, —$CH_2CN$, and —$CH_2CH_2CN$;

xiv) —$(CR^{17a}R^{17b})_q NO_2$; for example; —$NO_2$, —$CH_2NO_2$, and —$CH_2CH_2NO_2$;

xv) —$(CR^{17a}R^{17b})_q SO_2R^{16}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and xvi) —$(CR^{17a}R^{17b})_q SO_3R^{16}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{16}$ is independently hydrogen, substituted or unsubstituted $C_1$-$C_4$ linear, branched, or cyclic alkyl; or two $R^{16}$ units can be taken together to form a ring comprising 3-7 atoms; $R^{17a}$ and $R^{17b}$ are each independently hydrogen or $C_1$-$C_4$ linear or branched alkyl; the index q is from 0 to 4.

When $R^{15}$ units comprise $C_1$-$C_{12}$ linear, branched, or cyclic alkyl, alkenyl; substituted or unsubstituted $C_6$ or $C_{10}$ aryl; substituted or unsubstituted $C_1$-$C_9$ heterocyclic; or substituted or unsubstituted $C_1$-$C_9$ heteroaryl; $R^{15}$ units can further have one or more hydrogen atoms substituted by $R^{18}$ units. Non-limiting examples of $R^{18}$ units include:

i) linear, branched, or cyclic alkyl, alkenyl, and alkynyl; for example, methyl ($C_1$), ethyl ($C_2$), n-propyl ($C_3$), iso-propyl ($C_3$), cyclopropyl ($C_3$), propylen-2-yl ($C_3$), propargyl ($C_3$), n-butyl ($C_4$), iso-butyl ($C_4$), sec-butyl ($C_4$), tert-butyl ($C_4$), cyclobutyl ($C_4$), n-pentyl ($C_5$), cyclopentyl ($C_5$), n-hexyl ($C_6$), and cyclohexyl ($C_6$);

ii) —$(CR^{20a}R^{20b})_q OR^{19}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

iii) —$(CR^{20a}R^{20b})_q C(O)R^{19}$; for example, —$COCH_3$, —$CH_2COCH_3$, —$OCH_2CH_3$, —$CH_2COCH_2CH_3$, —$COCH_2CH_3$, and —$CH_2COCH_2CH_3$;

iv) —$(CR^{20a}R^{20b})_q C(O)OR^{19}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

v) —$(CR^{20a}R^{20b})_q C(O)N(R^{19})_2$; for example, —$CONH_2$, —$CH_2CONH_2$, $CONHCH_3$, —$CH_2CONHCH_3$, —$CON(CH_3)_2$, and —$CH_2CON(CH_3)_2$;

vi) —$(CR^{20a}R^{20b})_q OC(O)N(R^{19})_2$; for example, —$OC(O)NH_2$, —$CH_2OC(O)NH_2$, —$OC(O)NHCH_3$, —$CH_2OC(O)NHCH_3$, —$OC(O)N(CH_3)_2$, and —$CH_2OC(O)N(CH_3)_2$;

vii) —$(CR^{20a}R^{20b})_q N(R^{19})_2$; for example, —$NH_2$, —$CH_2NH_2$, —$NHCH_3$, —$N(CH_3)_2$, —$NH(CH_2CH_3)$, —$CH_2NHCH_3$, —$CH_2N(CH_3)_2$, and —$CH_2NH(CH_2CH_3)$;

viii) halogen: —F, —Cl, —Br, and —I;

ix) —$CH_mX_n$; wherein X is halogen, m is from 0 to 2, m+n=3; for example, —$CH_2F$, —$CF_3$, —$CCl_3$, or —$CBr_3$;

x) —$(CR^{20a}R^{20b})_q CN$; for example; —CN, —$CH_2CN$, and —$CH_2CH_2CN$;

xi) —$(CR^{20a}R^{20b})_q NO_2$; for example; —$NO_2$, —$CH_2NO_2$, and —$CH_2CH_2NO_2$;

xii) —$(CR^{20a}R^{20b})_q SO_2R^{19}$; for example, —$SO_2H$, —$CH_2SO_2H$, —$SO_2CH_3$, $CH_2SO_2CH_3$, —$SO_2C_6H_5$, and —$CH_2SO_2C_6H_5$; and xiii) —$(CR^{20a}R^{20b})_q SO_3R^{19}$; for example, —$SO_3H$, —$CH_2SO_3H$, —$SO_3CH_3$, $CH_2SO_3CH_3$, —$SO_3C_6H_5$, and —$CH_2SO_3C_6H_5$;

wherein each $R^{19}$ is independently hydrogen, substituted or unsubstituted $C_1$-$C_4$ linear, branched, or cyclic alkyl; or two $R^{19}$ units can be taken together to form a ring comprising 3-7 atoms; $R^{20a}$ and $R^{20b}$ are each independently hydrogen or $C_1$-$C_4$ linear or branched alkyl; the index p is from 0 to 4.

In the description that follows, $R^{15}$ and $R^{18}$ units may be represented by specific ring substitutions, for example, a ring encompassed within the definition of R can be depicted as either having the formula:

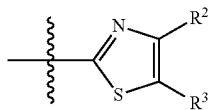

or as having the formula:

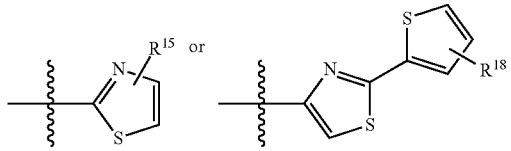

Both of the above formulae stand equally well for an optionally substituted thiazolyl ring.

R Units

R units comprise a ring having from 3 to 15 ring atoms.

R units can comprise 5-member heteroaryl rings. The following are non-limiting examples of 5-member heteroaryl rings:

i)

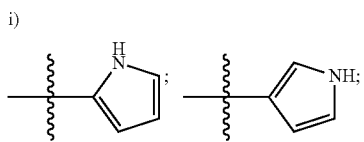

ii)

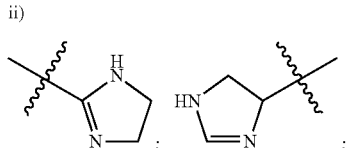

iii)

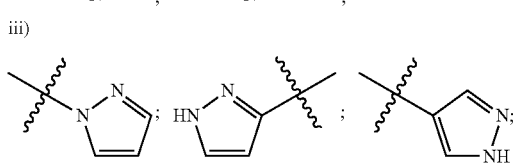

iv)

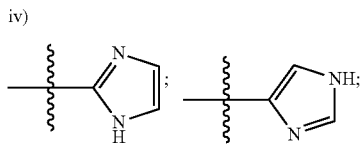

v)

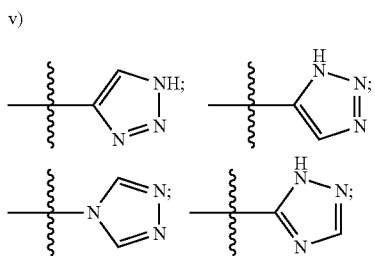

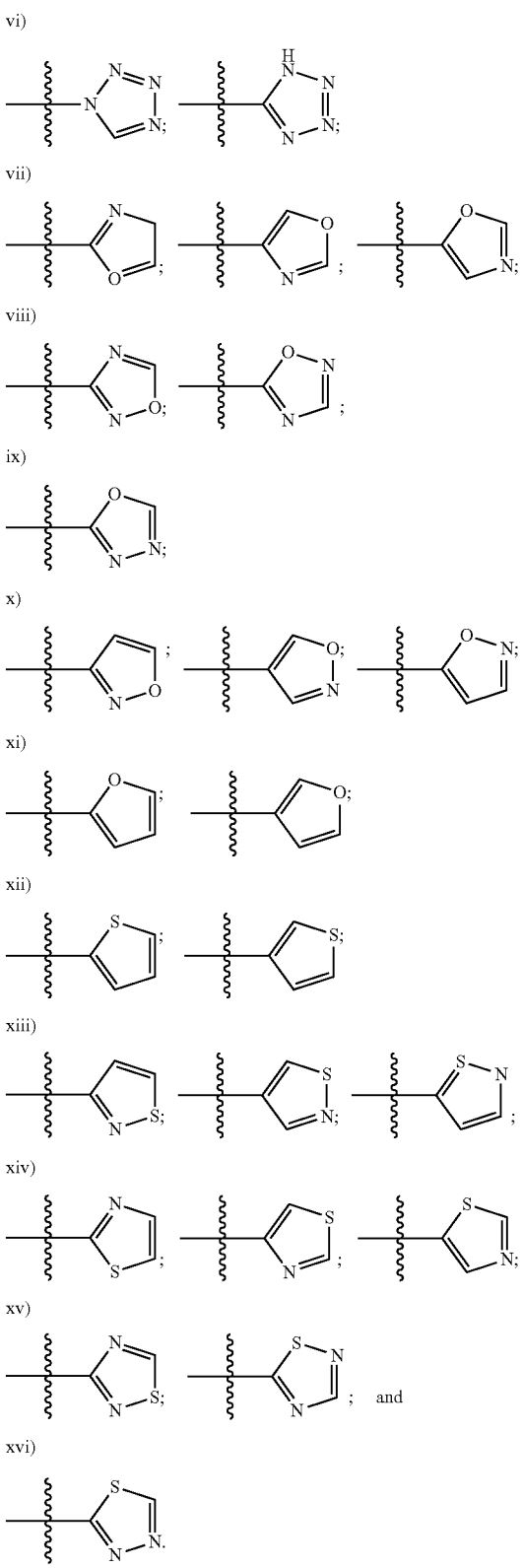

As described herein, the 5-member heteroaryl rings can be substituted with one or more substitutes for hydrogen, for example, with a methyl group:

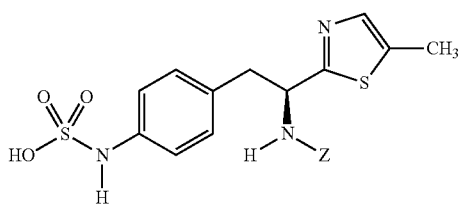

or with a substitute for hydrogen that itself is further substituted, for example:

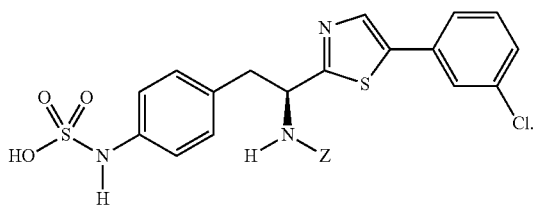

Examples of 5-member ring R units includes thiazolyl units having the formula:

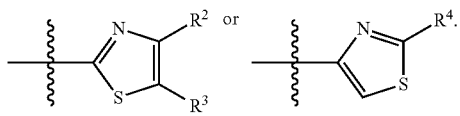

One example of a thiazolyl R unit includes thiazol-2-yl units having the formula:

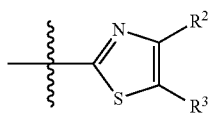

wherein $R^2$ and $R^3$ are each independently chosen from:
  i) hydrogen;
  ii) substituted or unsubstituted $C_1$-$C_6$ linear, branched, or cyclic alkyl;
  iii) substituted or unsubstituted phenyl;
  iv) substituted or unsubstituted $C_1$-$C_9$ heteroaryl; or
$R^2$ and $R^3$ can be taken together to form a saturated or unsaturated ring having from 5 to 7 atoms.

One example of this R unit relates to units having the formula:

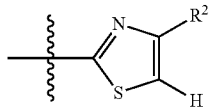

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

Another example of this R unit relates to units wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylthiazol-2-yl, 4-ethyl-5-methylthiazol-2-yl, 4-methyl-5-ethylthiazol-2-yl, and 4,5-diethylthiazol-2-yl.

A further example of this R unit relates to units wherein $R^3$ is hydrogen and $R^2$ is a substituted alkyl unit, the substitutions chosen from:
  i) halogen: —F, —Cl, —Br, and —I;
  ii) —N($R^{11}$)$_2$; and
  iii) —O$R^{11}$;
wherein each $R^{11}$ is independently hydrogen or $C_1$-$C_4$ linear or branched alkyl.

Non-limiting examples of units comprising this embodiment of R includes: —CH$_2$F, —CHF$_2$, —CF$_3$, —CH$_2$CF$_3$, —CH$_2$Cl, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and —CH$_2$NH(CH$_2$CH$_3$).

A yet further example of R units include units wherein $R^3$ is hydrogen and $R^2$ is phenyl.

A still further example of R units include units wherein $R^3$ is hydrogen and $R^2$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophene-2-yl, thiophene-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

One example of R includes units wherein $R^2$ is thiophene-2-yl or thiophene-3-yl.

Another example of R units includes thiazol-4-yl units having the formula:

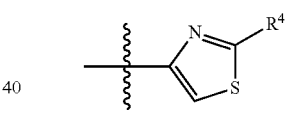

wherein $R^4$ is a unit chosen from:
  i) hydrogen;
  ii) substituted or unsubstituted $C_1$-$C_6$ linear, branched, or cyclic alkyl;
  iii) substituted or unsubstituted phenyl; or
  iv) substituted or unsubstituted $C_1$-$C_9$ heteroaryl.

An example of R units includes compounds wherein $R^4$ is hydrogen.

Another example of R units includes compounds wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methylthiazol-4-yl, 2-ethylthiazol-4-yl, 2-(n-propyl)thiazol-4-yl, and 2-(iso-propyl)thiazol-4-yl.

A further example of R units includes compounds wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

A yet further example of R units includes compounds wherein $R^4$ is substituted or unsubstituted heteroaryl, non-limiting examples of which include thiophene-2-yl, thiophene-3-yl, thiazol-2-yl, thiazol-4-yl, thiazol-5-yl, 2,5- dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

Another example of 5-member ring R units includes substituted or unsubstituted imidazolyl units having the formula:

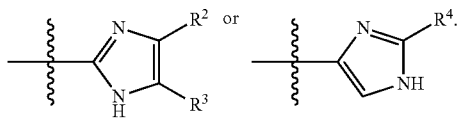

One example of imidazolyl R units includes imidazol-2-yl units having the formula:

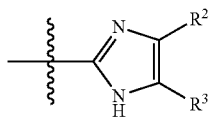

wherein $R^2$ and $R^3$ are each independently chosen from:
  i) hydrogen;
  ii) substituted or unsubstituted $C_1$-$C_6$ linear, branched, or cyclic alkyl;
  iii) substituted or unsubstituted phenyl;
  iv) substituted or unsubstituted $C_1$-$C_9$ heteroaryl; or
$R^2$ and $R^3$ can be taken together to form a saturated or unsaturated ring having from 5 to 7 atoms.

One example of R units includes compounds wherein R units have the formula:

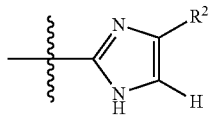

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

Another example of R units includes compounds wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylimidazol-2-yl, 4-ethyl-5-methylimidazol-2-yl, 4-methyl-5-ethylimidazol-2-yl, and 4,5-diethylimidazol-2-yl.

An example of R units includes compounds wherein $R^3$ is hydrogen and $R^2$ is a substituted alkyl unit chosen, said substitutions chosen from:
  i) halogen: —F, —Cl, —Br, and —I;
  ii) —N($R^{11}$)$_2$; and
  iii) —O$R^{11}$;
wherein each $R^{11}$ is independently hydrogen or $C_1$-$C_4$ linear or branched alkyl.
Non-limiting examples of units comprising this embodiment of R includes: —CH$_2$F, —CHF$_2$, —CF$_3$, —CH$_2$CF$_3$, —CH$_2$Cl, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and —CH$_2$NH(CH$_2$CH$_3$).

A yet further example of R units include units wherein $R^3$ is hydrogen and $R^2$ is phenyl.

A still further example of R units include units wherein $R^3$ is hydrogen and $R^2$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophene-2-yl, thiophene-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

One example of R includes units wherein $R^2$ is thiophene-2-yl or thiophene-3-yl.

Another example of R units includes imidazol-4-yl units having the formula:

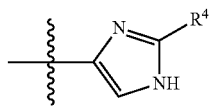

wherein $R^4$ is a unit chosen from:
  i) hydrogen;
  ii) substituted or unsubstituted $C_1$-$C_6$ linear, branched, or cyclic alkyl;
  iii) substituted or unsubstituted phenyl; or
  iv) substituted or unsubstituted $C_1$-$C_9$ heteroaryl.

One example of this embodiment of R units relates to compounds wherein $R^4$ is hydrogen.

An example of R units includes compounds wherein $R^4$ is hydrogen.

Another example of R units includes compounds wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methylimidazol-4-yl, 2-ethylimidazol-4-yl, 2-(n-propyl)imidazol-4-yl, and 2-(iso-propyl)imidazol-4-yl.

A further example of R units includes compounds wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

A yet further example of R units includes compounds wherein $R^4$ is substituted or unsubstituted heteroaryl, non-limiting examples of which include thiophene-2-yl, thiophene-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

Further examples of 5-member ring R units are substituted or unsubstituted oxazolyl units having the formula:

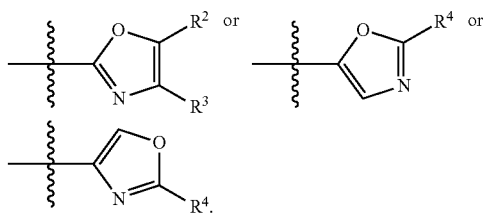

One example of oxazolyl R units includes oxazol-2-yl units having the formula:

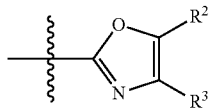

wherein $R^2$ and $R^3$ are each independently chosen from:
i) hydrogen;
ii) substituted or unsubstituted $C_1$-$C_6$ linear, branched, or cyclic alkyl;
iii) substituted or unsubstituted phenyl;
iv) substituted or unsubstituted $C_1$-$C_9$ heteroaryl; or
$R^2$ and $R^3$ can be taken together to form a saturated or unsaturated ring having from 5 to 7 atoms.

One example of R units includes compounds wherein R units have the formula:

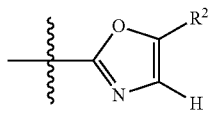

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

Another example of R units includes units wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethyloxazol-2-yl, 4-ethyl-5-methyloxazol-2-yl, 4-methyl-5-ethyloxazol-2-yl, and 4,5-diethyloxazol-2-yl.

A further example of R units includes units wherein $R^3$ is hydrogen and $R^2$ is a substituted alkyl unit chosen, said substitutions chosen from:
i) halogen: —F, —Cl, —Br, and —I;
ii) —N($R^{11}$)$_2$; and
iii) —O$R^{11}$;
wherein each $R^{11}$ is independently hydrogen or $C_1$-$C_4$ linear or branched alkyl.

Non-limiting examples of units comprising this embodiment of R includes: —CH$_2$F, —CHF$_2$, —CF$_3$, —CH$_2$CF$_3$, —CH$_2$Cl, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and —CH$_2$NH(CH$_2$CH$_3$).

A yet further example of R units include units wherein $R^3$ is hydrogen and $R^2$ is phenyl.

A still further example of R units include units wherein $R^3$ is hydrogen and $R^2$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophene-2-yl, thiophene-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

One example of R includes units wherein $R^2$ is thiophene-2-yl or thiophene-3-yl.

Another example of R units includes oxazol-4-yl units having the formula:

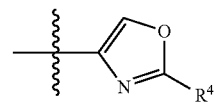

wherein $R^4$ is a unit chosen from:
i) hydrogen;
ii) substituted or unsubstituted $C_1$-$C_6$ linear, branched, or cyclic alkyl;
iii) substituted or unsubstituted phenyl; or
iv) substituted or unsubstituted $C_1$-$C_9$ heteroaryl.
wherein $R^4$ is a unit chosen from:
i) hydrogen;
ii) substituted or unsubstituted $C_1$-$C_6$ linear, branched, or cyclic alkyl;
iii) substituted or unsubstituted phenyl; or
iv) substituted or unsubstituted $C_1$-$C_9$ heteroaryl.

One example of this embodiment of R units relates to compounds wherein $R^4$ is hydrogen.

An example of R units includes compounds wherein $R^4$ is hydrogen.

Another example of R units includes compounds wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methyloxazol-4-yl, 2-ethyloxazol-4-yl, 2-(n-propyl)oxazol-4-yl, and 2-(iso-propyl)oxazol-4-yl.

A further example of R units includes compounds wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

A yet further example of R units includes compounds wherein $R^4$ is substituted or unsubstituted heteroaryl, non-limiting examples of which include thiophene-2-yl, thiophene-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

A further example of R units relates to oxazol-5-yl units having the formula:

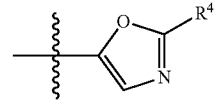

wherein $R^4$ is a unit chosen from:
i) hydrogen;
ii) substituted or unsubstituted $C_1$-$C_6$ linear, branched, or cyclic alkyl;
iii) substituted or unsubstituted phenyl; or
iv) substituted or unsubstituted $C_1$-$C_9$ heteroaryl.

An example of R units includes compounds wherein $R^4$ is hydrogen.

Another example of R units includes compounds wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methyloxazol-4-yl, 2-ethyloxazol-4-yl, 2-(n-propyl)oxazol-4-yl, and 2-(iso-propyl)oxazol-4-yl.

A further example of R units includes compounds wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

A yet further example of R units includes compounds wherein $R^4$ is substituted or unsubstituted heteroaryl, non-limiting examples of which include thiophene-2-yl, thiophene-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

A yet further example of 5-member ring R units includes substituted or unsubstituted [1,2,4]oxadiazolyl units having the formula:

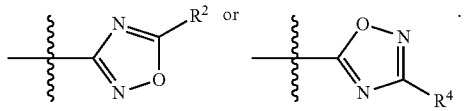

One example of [1,2,4]oxadiazolyl R units includes [1,2,4]oxadiazol-3-yl units having the formula:

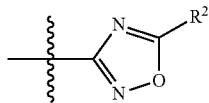

wherein $R^2$ is chosen from:
  i) hydrogen;
  ii) substituted or unsubstituted $C_1$-$C_6$ linear, branched, or cyclic alkyl;
  iii) substituted or unsubstituted phenyl; or
  iv) substituted or unsubstituted $C_1$-$C_9$ heteroaryl;

One example of R units includes units wherein $R^2$ is hydrogen.

Another example includes R units wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 5-methyl[1,2,4]oxadiazol-2-yl, 5-ethyl[1,2,4]-oxadiazol-2-yl, 5-propyl[1,2,4]oxadiazol-2-yl, and 5-cyclopropyl[1,2,4]oxadiazol-2-yl.

A further example of R units includes units wherein $R^2$ is a substituted alkyl unit chosen, said substitutions chosen from:
  i) halogen: —F, —Cl, —Br, and —I;
  ii) —N($R^{11}$)$_2$; and
  iii) —O$R^{11}$;
wherein each $R^{11}$ is independently hydrogen or $C_1$-$C_4$ linear or branched alkyl.

Non-limiting examples of units comprising this embodiment of R includes: —CH$_2$F, —CHF$_2$, —CF$_3$, —CH$_2$CF$_3$, —CH$_2$Cl, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and —CH$_2$NH(CH$_2$CH$_3$).

A yet further example of R units includes units wherein $R^2$ is phenyl.

A still further example of R units includes units wherein $R^2$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophene-2-yl, thiophene-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Specific examples of R units include units wherein $R^2$ is thiophene-2-yl or thiophene-3-yl.

Another example of R units includes [1,2,4]oxadiazol-5-yl units having the formula:

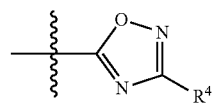

wherein $R^4$ is a unit chosen from:
  i) hydrogen;
  ii) substituted or unsubstituted $C_1$-$C_6$ linear, branched, or cyclic alkyl;
  iii) substituted or unsubstituted phenyl; or
  iv) substituted or unsubstituted $C_1$-$C_9$ heteroaryl.

One example of R units includes compounds wherein $R^4$ is hydrogen.

Another example of R units include compounds wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 3-methyl[1,2,4]oxadiazol-5-yl, 3-ethyl[1,2,4]oxadiazol-5-yl, 3-(n-propyl)[1,2,4]oxadiazol-5-yl, and 3-(iso-propyl)[1,2,4]oxadiazol-5-yl.

A further example of R units includes compounds wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

A yet further example of R units includes compounds wherein $R^4$ is substituted or unsubstituted heteroaryl, non-limiting examples of which include thiophene-2-yl, thiophene-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

Further non-limiting examples of 5-member heteroaryl rings include:

i)
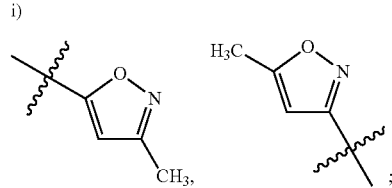

ii) 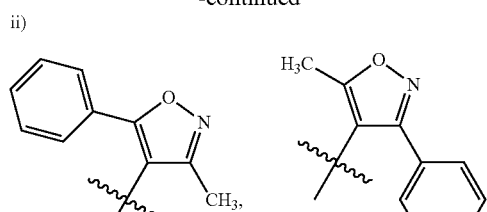
iii) 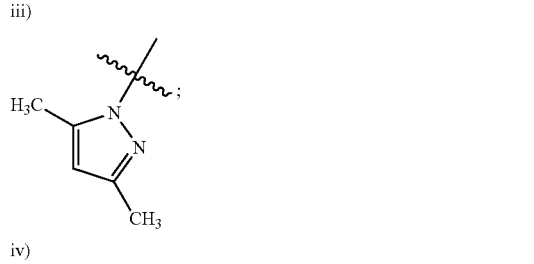
iv) 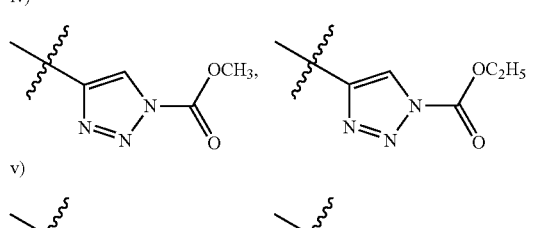
v) 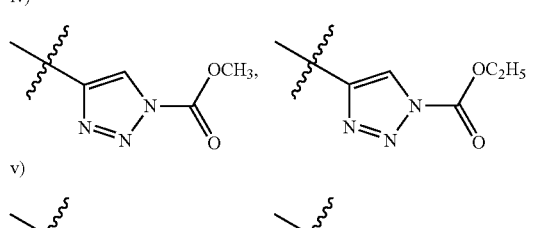
vi) 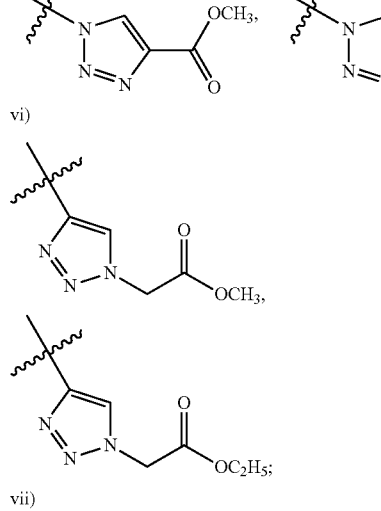
vii) 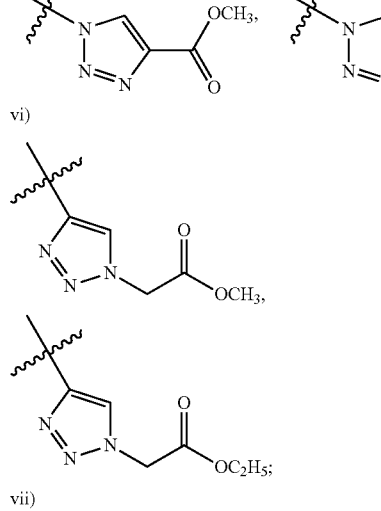
viii) 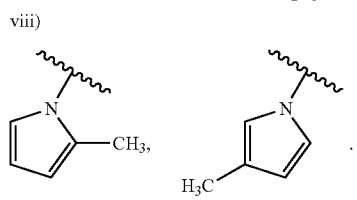
R units can comprise 5-member heterocyclic rings. Non-limiting examples of 5-member heterocyclic rings include:
i) 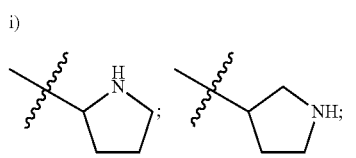
ii) 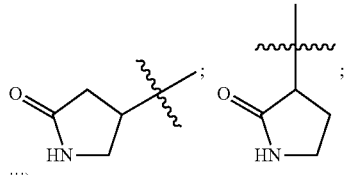
iii) 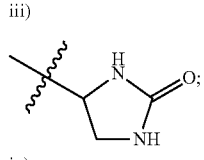
iv) 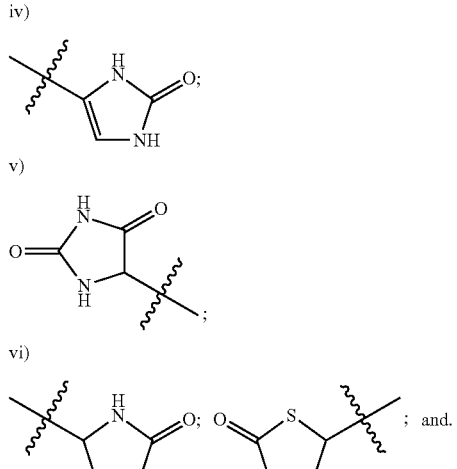
v) 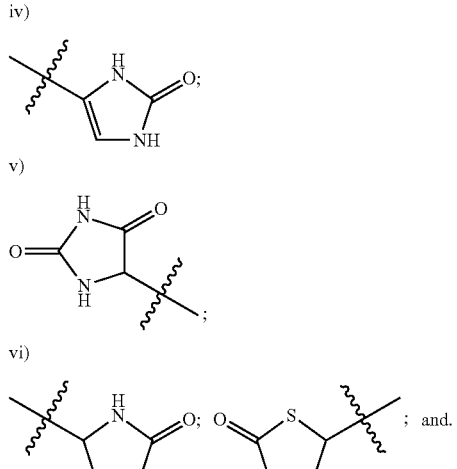
vi) 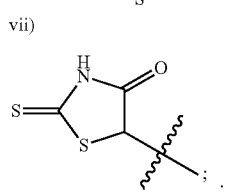
vii) 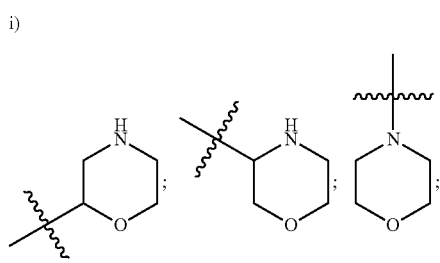
R units can comprise 6-member heterocyclic rings. Non-limiting examples of 6-member heterocyclic rings include:
i) 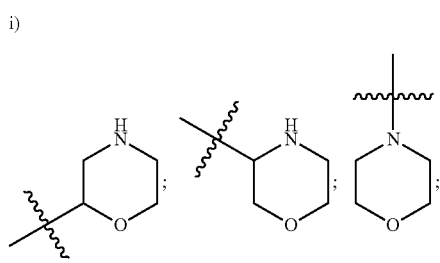

ii)

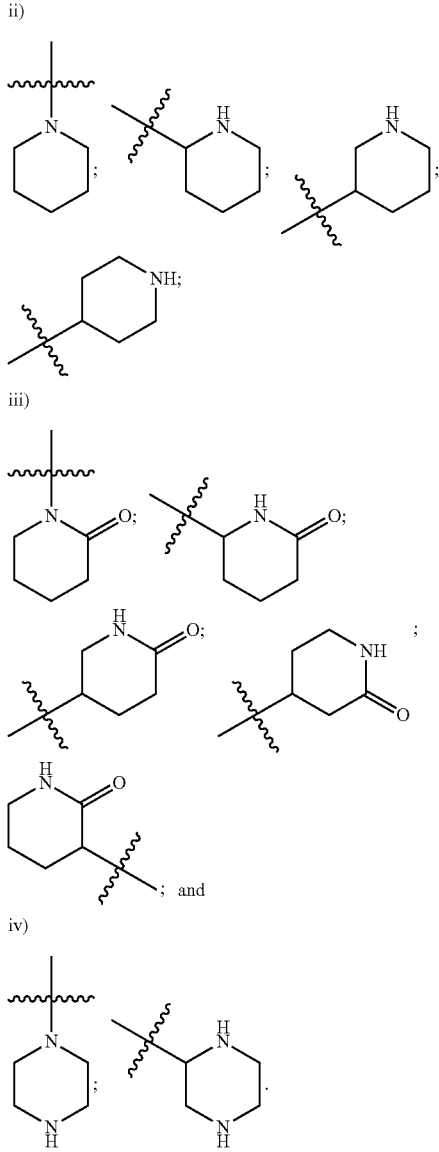

iii)

iv)

R units can comprise 6-member heteraryl rings. Non-limiting examples of 6-member heteroaryl rings include:

i)

ii)

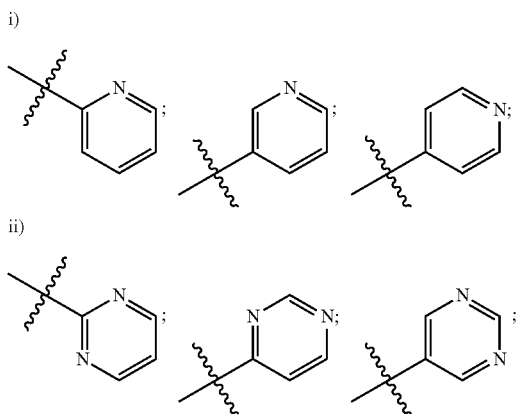

iii)

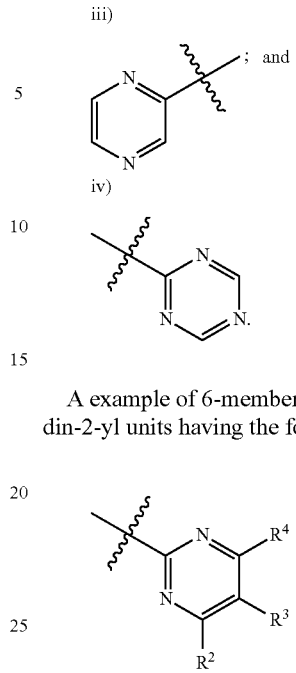

; and iv)

A example of 6-member heteroaryl rings includes pyrimidin-2-yl units having the formula:

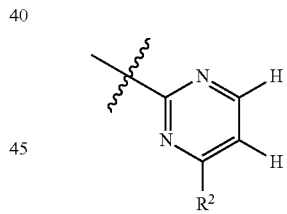

wherein $R^2$, $R^3$ and $R^4$ are each independently chosen from:
  i) hydrogen;
  ii) substituted or unsubstituted $C_1$-$C_6$ linear, branched, or cyclic alkyl;
  iii) substituted or unsubstituted phenyl;
  iv) substituted or unsubstituted $C_1$-$C_9$ heteroaryl; or
$R^2$ and $R^3$ or $R^3$ and $R^4$ can be taken together to form a saturated or unsaturated ring having from 5 to 7 atoms.

Another example of R units includes units having the formula:

wherein $R^3$ and $R^4$ are both hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

Further examples of R units include units wherein $R^2$ and $R^3$ are chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^4$ is hydrogen. Non-limiting examples of this aspect of R includes 4,5-dimethylpyrimidin-2-yl, 4,5-diethylpyrimidin-2-yl, 4-methyl-5-ethyl-pyrimidin-2-yl, and 4-ethyl-5-methyl-pyrimidin-2-yl.

A yet further example of R units include units wherein $R^4$ is hydrogen and $R^2$ and $R^3$ are chosen from:
  i) halogen: —F, —Cl, —Br, and —I;
  ii) —N($R^{11}$)$_2$; and
  iii) —O$R^{11}$;
wherein each $R^{11}$ is independently hydrogen or $C_1$-$C_4$ linear or branched alkyl.

Non-limiting examples of units comprising this embodiment of R includes: —CH$_2$F, —CHF$_2$, —CF$_3$, —CH$_2$CF$_3$, —CH$_2$Cl, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and —CH$_2$NH(CH$_2$CH$_3$).

A yet further example of R units includes units wherein R$^2$ or R$^3$ is substituted phenyl and R$^4$ is hydrogen.

A still further example of R units includes units wherein R$^4$ is hydrogen and R$^2$ or R$^3$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophene-2-yl, thiophene-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

The following are non-limiting examples of R units wherein R$^2$ is thiophene-2-yl and wherein R$^2$ is thiophene-3-yl thereby providing R units that are 4-(thiophene-2-yl)pyrimidin-2-yl, 5-(thiophene-2-yl)pyrimidin-2-yl, 4-(thiophene-3-yl)pyrimidin-2-yl, and 5-(thiophene-2-yl)pyrimidin-3-yl.

Non-limiting examples of 6-member heteroaryl rings include:

i)

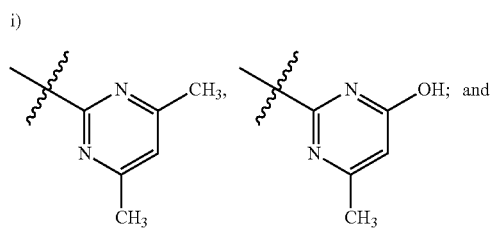

ii)

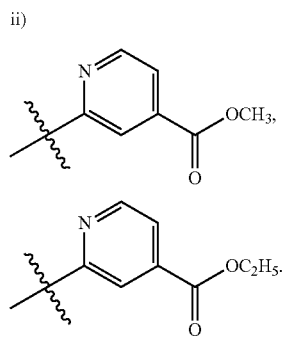

R units can also comprise fuse ring heteroaryl units. Non-limiting examples of R units include:

i)

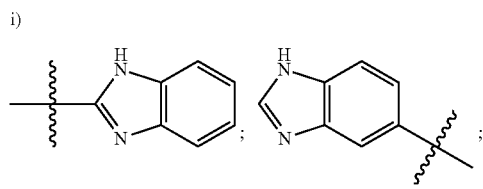

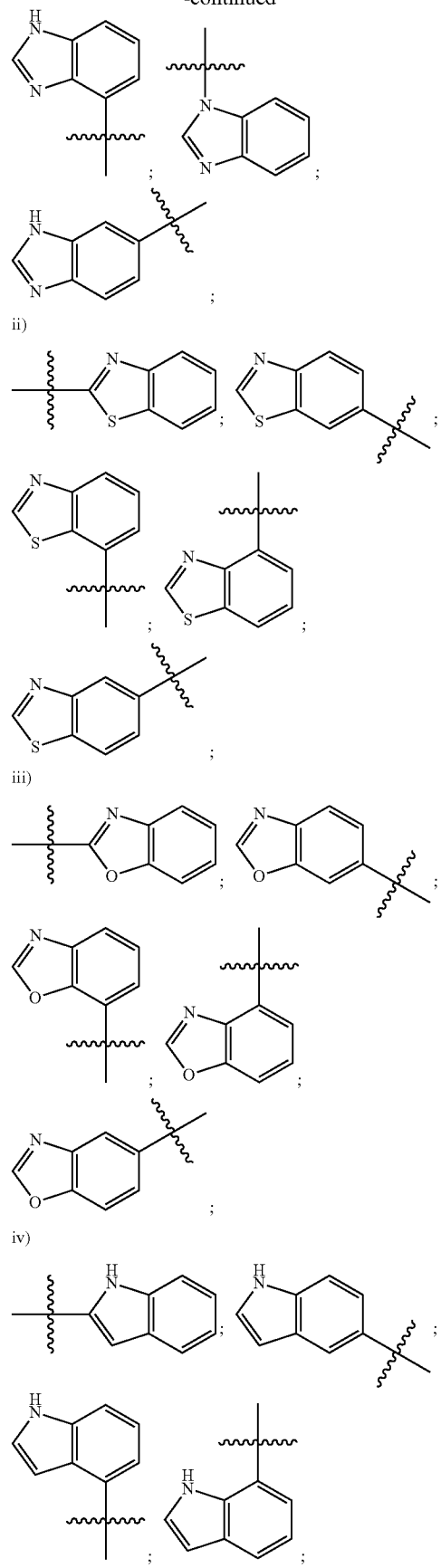

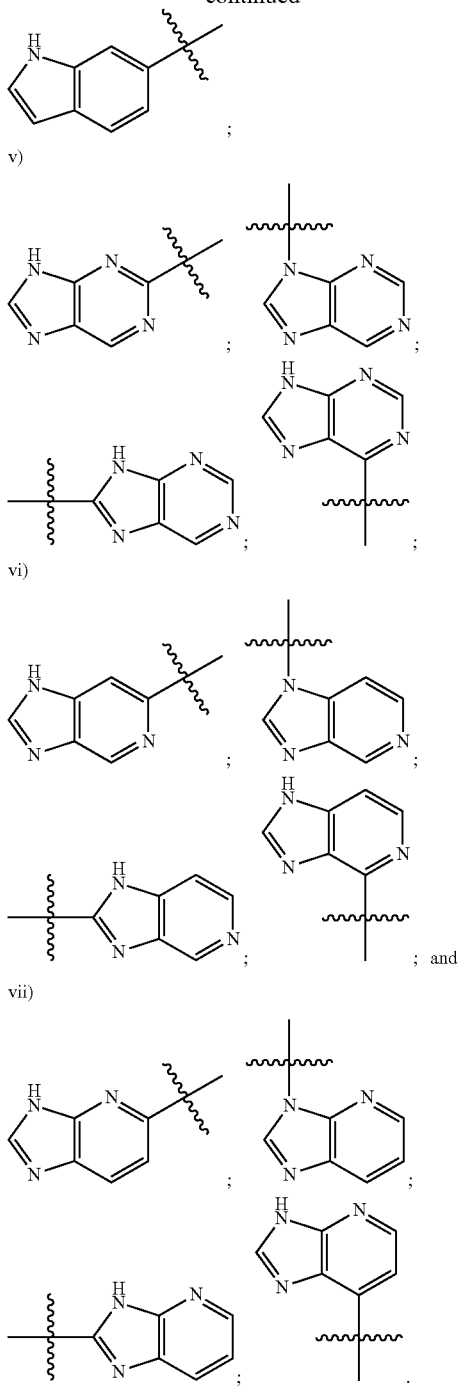

R units that are fused heteroaryl rings can be optionally substituted by one or more independently chosen substitutes for hydrogen as described herein above.

Z Units

Z is a unit having the formula:

-(L)$_n$-R$^1$ wherein R$^1$ is chosen from:
i) hydrogen;
ii) substituted or unsubstituted C$_1$-C$_6$ linear, branched or cyclic alkyl;
iii) substituted or unsubstituted C$_6$ or C$_{10}$ aryl;
iv) substituted or unsubstituted C$_1$-C$_9$ heterocyclic rings; or
v) substituted or unsubstituted C$_1$-C$_9$ heteroaryl rings.

One example of R$^1$ units includes substituted or unsubstituted phenyl (C$_6$ aryl) units, wherein each substitution is independently chosen from: halogen, C$_1$-C$_4$ linear, branched alkyl, or cyclic alkyl, —OR$^{11}$, —CN, —N(R$^{11}$)$_2$, —CO$_2$R$^{11}$, —C(O)N(R$^{11}$)$_2$, —NR$^{11}$C(O)R$^{11}$, —NO$_2$, and —SO$_2$R$^{11}$; each R$^{11}$ is independently hydrogen; substituted or unsubstituted C$_1$-C$_4$ linear, branched, cyclic alkyl, alkenyl, or alkynyl; substituted or unsubstituted phenyl or benzyl; or two R$^{11}$ units can be taken together to form a ring comprising from 3-7 atoms.

Another example of R$^1$ units includes substituted C$_6$ aryl units chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl.

A further example of R$^1$ units includes substituted or unsubstituted C$_6$ aryl units chosen from phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, and 2,4,6-trichlorophenyl.

A yet further example of R$^1$ units includes substituted C$_6$ aryl units chosen from 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethyl-phenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Another still further example of R$^1$ units includes substituted C$_6$ aryl units chosen from 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

R$^1$ can comprise heteroaryl units. Non-limiting examples of heteroaryl units include:

i)

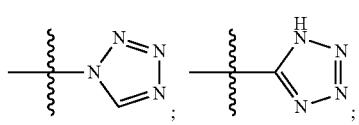

ii)

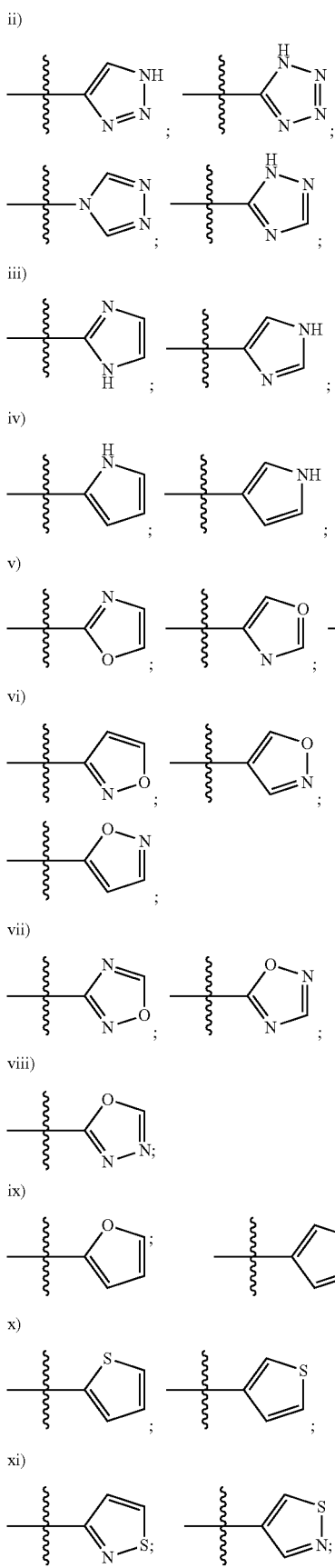

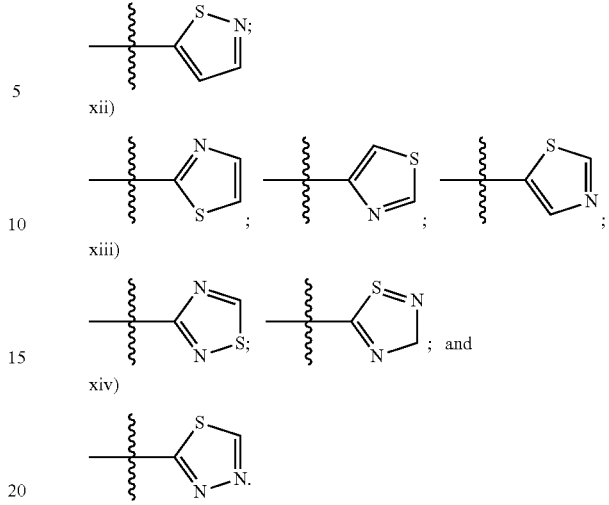

R[1] heteroaryl units can be substituted or unsubstituted. Non-limiting examples of units that can substitute for hydrogen include units chosen from:
  i) $C_1$-$C_6$ linear, branched, and cyclic alkyl;
  ii) substituted or unsubstituted phenyl and benzyl;
  iii) substituted of unsubstituted $C_1$-$C_9$ heteroaryl;
  iv) —C(O)R[9]; and
  v) —NHC(O)R[9];
wherein R[9] is $C_1$-$C_6$ linear and branched alkyl; $C_1$-$C_6$ linear and branched alkoxy; or —NHCH$_2$C(O)R[10]; R[10] is chosen from hydrogen, methyl, ethyl, and tert-butyl.

An example of R[1] relates to units substituted by an alkyl unit chosen from methyl, ethyl, n-propyl, iso-propyl, n-butyl, iso-butyl, sec-butyl, and tert-butyl.

Another example of R[1] includes units that are substituted by substituted or unsubstituted phenyl and benzyl, wherein the phenyl and benzyl substitutions are chosen from one or more:
  i) halogen;
  ii) $C_1$-$C_3$ alkyl;
  iii) $C_1$-$C_3$ alkoxy;
  iv) —CO$_2$R[11]; and
  v) —NHCOR[16];
wherein R[11] and R[16] are each independently hydrogen, methyl, or ethyl.

Another example of R[1] relates to phenyl and benzyl units substituted by a carboxy unit having the formula —C(O)R[9]; R[9] is chosen from methyl, methoxy, ethyl, and ethoxy.

A further example of R[1] includes phenyl and benzyl units substituted by an amide unit having the formula —NHC(O)R[9]; R[9] is chosen from methyl, methoxy, ethyl, ethoxy, tert-butyl, and tert-butoxy.

A yet further example of R[1] includes phenyl and benzyl units substituted by one or more fluoro or chloro units.

L is a linking unit chosen from:
  i) —C(O)NH[C(R[5a]R[5b])]$_w$—;
  ii) —C(O)[C(R[6a]R[6b])]$_x$—;
  iii) —C(O)[C(R[7a]R[7b])]$_y$C(O)—;
  iv) —SO$_2$[C(R[8a]R[8b])]$_z$—,
wherein R[5a], R[5b], R[6a], R[6b], R[7a], R[7b], R[8a], and R[8b] are each independently:
  i) hydrogen;
  ii) $C_1$-$C_4$ substituted or unsubstituted linear or branched alkyl;
  iii) substituted or unsubstituted aryl;

iv) substituted or unsubstituted heterocyclic rings;
v) substituted or unsubstituted $C_1$-$C_9$ heteroaryl rings;
and the indices w, x, y, and z are each independently from 1 to 4. The linking group may be present, i.e. when the index n is equal to 1, or absent when the index n is equal to 0, for example, the linking unit is absent in Category V compounds further described herein below.

One example of L units includes linking units having the formula:

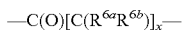
—C(O)[C($R^{6a}R^{6b}$)]$_x$— wherein $R^{6a}$ is hydrogen, substituted or unsubstituted phenyl, and substituted or unsubstituted heteroaryl, said substitutions for phenyl and heteroaryl are chosen from:
  i) $C_1$-$C_6$ linear, branched, and cyclic alkyl;
  ii) substituted or unsubstituted phenyl and benzyl;
  iii) substituted of unsubstituted $C_1$-$C_9$ heteroaryl;
  iv) —C(O)$R^{16}$; and
  v) —NHC(O)$R^{16}$;
wherein $R^{16}$ is $C_1$-$C_6$ linear and branched alkyl; $C_1$-$C_6$ linear and branched alkoxy; or —NHCH$_2$C(O)$R^{17}$; $R^{17}$ is chosen from hydrogen, methyl, ethyl, and tert-butyl; the index x is 1 or 2.

Another example of L units includes units wherein a first $R^{6a}$ unit chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl; a second $R^{6a}$ unit is hydrogen and $R^{6b}$ units are hydrogen. For example a linking unit having the formula:

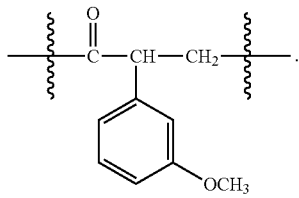

A further example of L includes a first $R^{6a}$ unit as depicted herein above that is a substituted or unsubstituted heteroaryl unit as described herein above.

A yet further example of L includes units having the formula:

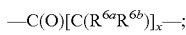
—C(O)[C($R^{6a}R^{6b}$)]$_x$—;

wherein $R^{6a}$ and $R^{6b}$ are hydrogen and the index x is equal to 1 or 2; said units chosen from:
  i) —C(O)CH$_2$—; and
  ii) —C(O)CH$_2$CH$_2$—.

Another example of L units includes units having the formula:

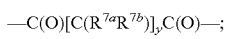
—C(O)[C($R^{7a}R^{7b}$)]$_y$C(O)—;

wherein $R^{7a}$ and $R^{7b}$ are hydrogen and the index x is equal to 1 or 2; said units chosen from:
  i) —C(O)CH$_2$C(O)—; and
  ii) —C(O)CH$_2$CH$_2$C(O)—.

A still further example of L units includes units having the formula:

—C(O)NH[C($R^{5a}R^{5b}$)]$_w$—;

wherein $R^{5a}$ and $R^{5b}$ are hydrogen and the index w is equal to 0, 1 or 2; said units chosen from:
  ii) —C(O)NH—;
  ii) —C(O)NHCH$_2$—; and
  iii) —C(O)NHCH$_2$CH$_2$—.

A yet still further example of L units includes units having the formula:

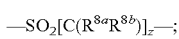
—SO$_2$[C($R^{8a}R^{8b}$)]$_z$—;

wherein $R^{8a}$ and $R^{8b}$ are hydrogen and the index z is equal to 0, 1 or 2; said units chosen from:
  ii) —SO$_2$—;
  ii) —SO$_2$CH$_2$—; and
  iii) —SO$_2$CH$_2$CH$_2$—.

A described herein above the compounds of the present invention includes all pharmaceutically acceptable salt forms. A compound having the formula:

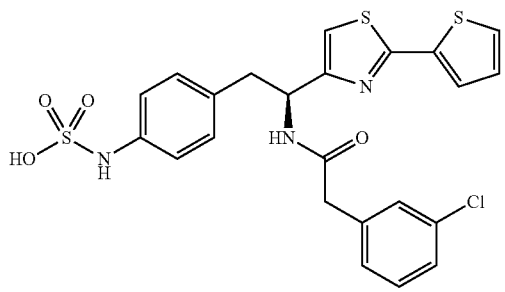

can form salts, for example, a salt of the sulfonic acid:

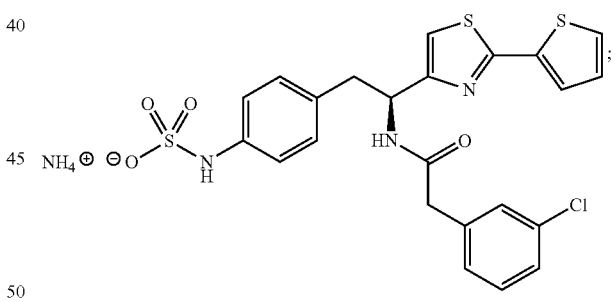

and

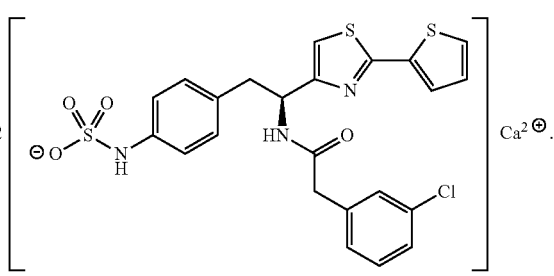

The compounds can also exist in a zwitterionic form, for example:

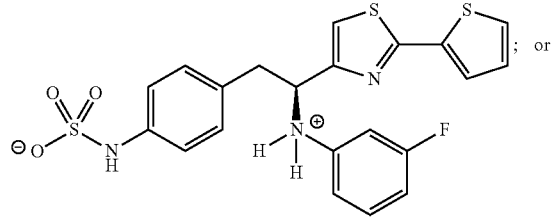

as a salt of a strong acid, for example:

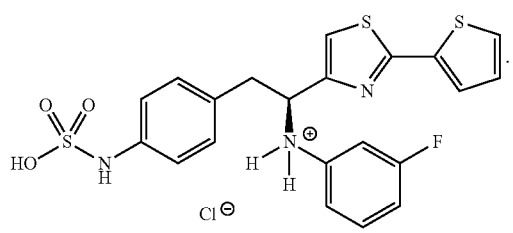

The analogs (compounds) of the present disclosure are arranged into several Categories to assist the formulator in applying a rational synthetic strategy for the preparation of analogs which are not expressly examples herein. The arrangement into categories does not imply increased or decreased efficacy for any of the compositions of matter described herein.

The first aspect of Category I of the present disclosure relates to 2-(thiazol-2-yl) compounds having the formula:

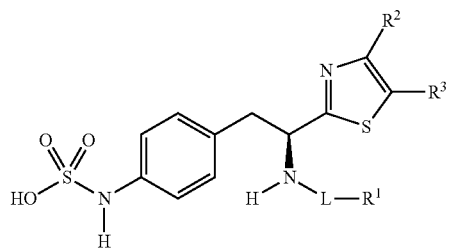

wherein $R^1$, $R^2$, $R^3$, and L are further defined herein in Table I herein below.

TABLE I

| No. | L | $R^1$ | $R^2$ | $R^3$ |
|---|---|---|---|---|
| 1 | —C(O)CH$_2$— | phenyl | —CH$_3$ | —H |
| 2 | —C(O)CH$_2$— | 2-fluorophenyl | —CH$_3$ | —H |
| 3 | —C(O)CH$_2$— | 3-fluorophenyl | —CH$_3$ | —H |
| 4 | —C(O)CH$_2$— | 4-fluorophenyl | —CH$_3$ | —H |
| 5 | —C(O)CH$_2$— | 2,3-difluorophenyl | —CH$_3$ | —H |
| 6 | —C(O)CH$_2$— | 3,4-difluorophenyl | —CH$_3$ | —H |
| 7 | —C(O)CH$_2$— | 3,5-difluorophenyl | —CH$_3$ | —H |
| 8 | —C(O)CH$_2$— | 2-chlorophenyl | —CH$_3$ | —H |
| 9 | —C(O)CH$_2$— | 3-chlorophenyl | —CH$_3$ | —H |
| 10 | —C(O)CH$_2$— | 4-chlorophenyl | —CH$_3$ | —H |
| 11 | —C(O)CH$_2$— | 2,3-dichlorophenyl | —CH$_3$ | —H |
| 12 | —C(O)CH$_2$— | 3,4-dichlorophenyl | —CH$_3$ | —H |
| 13 | —C(O)CH$_2$— | 3,5-dichlorophenyl | —CH$_3$ | —H |
| 14 | —C(O)CH$_2$— | 2-hydroxyphenyl | —CH$_3$ | —H |
| 15 | —C(O)CH$_2$— | 3-hydroxyphenyl | —CH$_3$ | —H |
| 16 | —C(O)CH$_2$— | 4-hydroxyphenyl | —CH$_3$ | —H |
| 17 | —C(O)CH$_2$— | 2-methoxyphenyl | —CH$_3$ | —H |
| 18 | —C(O)CH$_2$— | 3-methoxyphenyl | —CH$_3$ | —H |
| 19 | —C(O)CH$_2$— | 4-methoxyphenyl | —CH$_3$ | —H |
| 20 | —C(O)CH$_2$— | 2,3-dimethoxyphenyl | —CH$_3$ | —H |
| 21 | —C(O)CH$_2$— | 3,4-dimethoxyphenyl | —CH$_3$ | —H |
| 22 | —C(O)CH$_2$— | 3,5-dimethoxyphenyl | —CH$_3$ | —H |
| 23 | —C(O)CH$_2$— | phenyl | —CH$_2$CH$_3$ | —H |
| 24 | —C(O)CH$_2$— | 2-fluorophenyl | —CH$_2$CH$_3$ | —H |
| 25 | —C(O)CH$_2$— | 3-fluorophenyl | —CH$_2$CH$_3$ | —H |
| 26 | —C(O)CH$_2$— | 4-fluorophenyl | —CH$_2$CH$_3$ | —H |
| 27 | —C(O)CH$_2$— | 2,3-difluorophenyl | —CH$_2$CH$_3$ | —H |
| 28 | —C(O)CH$_2$— | 3,4-difluorophenyl | —CH$_2$CH$_3$ | —H |
| 29 | —C(O)CH$_2$— | 3,5-difluorophenyl | —CH$_2$CH$_3$ | —H |
| 30 | —C(O)CH$_2$— | 2-chlorophenyl | —CH$_2$CH$_3$ | —H |
| 31 | —C(O)CH$_2$— | 3-chlorophenyl | —CH$_2$CH$_3$ | —H |
| 32 | —C(O)CH$_2$— | 4-chlorophenyl | —CH$_2$CH$_3$ | —H |
| 33 | —C(O)CH$_2$— | 2,3-dichlorophenyl | —CH$_2$CH$_3$ | —H |
| 34 | —C(O)CH$_2$— | 3,4-dichlorophenyl | —CH$_2$CH$_3$ | —H |
| 35 | —C(O)CH$_2$— | 3,5-dichlorophenyl | —CH$_2$CH$_3$ | —H |
| 36 | —C(O)CH$_2$— | 2-hydroxyphenyl | —CH$_2$CH$_3$ | —H |
| 37 | —C(O)CH$_2$— | 3-hydroxyphenyl | —CH$_2$CH$_3$ | —H |
| 38 | —C(O)CH$_2$— | 4-hydroxyphenyl | —CH$_2$CH$_3$ | —H |
| 39 | —C(O)CH$_2$— | 2-methoxyphenyl | —CH$_2$CH$_3$ | —H |
| 40 | —C(O)CH$_2$— | 3-methoxyphenyl | —CH$_2$CH$_3$ | —H |
| 41 | —C(O)CH$_2$— | 4-methoxyphenyl | —CH$_2$CH$_3$ | —H |
| 42 | —C(O)CH$_2$— | 2,3-dimethoxyphenyl | —CH$_2$CH$_3$ | —H |
| 43 | —C(O)CH$_2$— | 3,4-dimethoxyphenyl | —CH$_2$CH$_3$ | —H |
| 44 | —C(O)CH$_2$— | 3,5-dimethoxyphenyl | —CH$_2$CH$_3$ | —H |
| 45 | —C(O)CH$_2$CH$_2$— | phenyl | —CH$_3$ | —H |
| 46 | —C(O)CH$_2$CH$_2$— | 2-fluorophenyl | —CH$_3$ | —H |
| 47 | —C(O)CH$_2$CH$_2$— | 3-fluorophenyl | —CH$_3$ | —H |
| 48 | —C(O)CH$_2$CH$_2$— | 4-fluorophenyl | —CH$_3$ | —H |
| 49 | —C(O)CH$_2$CH$_2$— | 2,3-difluorophenyl | —CH$_3$ | —H |
| 50 | —C(O)CH$_2$CH$_2$— | 3,4-difluorophenyl | —CH$_3$ | —H |
| 51 | —C(O)CH$_2$CH$_2$— | 3,5-difluorophenyl | —CH$_3$ | —H |
| 52 | —C(O)CH$_2$CH$_2$— | 2-chlorophenyl | —CH$_3$ | —H |
| 53 | —C(O)CH$_2$CH$_2$— | 3-chlorophenyl | —CH$_3$ | —H |
| 54 | —C(O)CH$_2$CH$_2$— | 4-chlorophenyl | —CH$_3$ | —H |
| 55 | —C(O)CH$_2$CH$_2$— | 2,3-dichlorophenyl | —CH$_3$ | —H |
| 56 | —C(O)CH$_2$CH$_2$— | 3,4-dichlorophenyl | —CH$_3$ | —H |
| 57 | —C(O)CH$_2$CH$_2$— | 3,5-dichlorophenyl | —CH$_3$ | —H |
| 58 | —C(O)CH$_2$CH$_2$— | 2-hydroxyphenyl | —CH$_3$ | —H |
| 59 | —C(O)CH$_2$CH$_2$— | 3-hydroxyphenyl | —CH$_3$ | —H |
| 60 | —C(O)CH$_2$CH$_2$— | 4-hydroxyphenyl | —CH$_3$ | —H |
| 61 | —C(O)CH$_2$CH$_2$— | 2-methoxyphenyl | —CH$_3$ | —H |
| 62 | —C(O)CH$_2$CH$_2$— | 3-methoxyphenyl | —CH$_3$ | —H |
| 63 | —C(O)CH$_2$CH$_2$— | 4-methoxyphenyl | —CH$_3$ | —H |
| 64 | —C(O)CH$_2$CH$_2$— | 2,3-dimethoxyphenyl | —CH$_3$ | —H |
| 65 | —C(O)CH$_2$CH$_2$— | 3,4-dimethoxyphenyl | —CH$_3$ | —H |
| 66 | —C(O)CH$_2$CH$_2$— | 3,5-dimethoxyphenyl | —CH$_3$ | —H |
| 67 | —C(O)CH$_2$CH$_2$— | phenyl | —CH$_2$CH$_3$ | —H |
| 68 | —C(O)CH$_2$CH$_2$— | 2-fluorophenyl | —CH$_2$CH$_3$ | —H |
| 69 | —C(O)CH$_2$CH$_2$— | 3-fluorophenyl | —CH$_2$CH$_3$ | —H |
| 70 | —C(O)CH$_2$CH$_2$— | 4-fluorophenyl | —CH$_2$CH$_3$ | —H |
| 71 | —C(O)CH$_2$CH$_2$— | 2,3-difluorophenyl | —CH$_2$CH$_3$ | —H |
| 72 | —C(O)CH$_2$CH$_2$— | 3,4-difluorophenyl | —CH$_2$CH$_3$ | —H |
| 73 | —C(O)CH$_2$CH$_2$— | 3,5-difluorophenyl | —CH$_2$CH$_3$ | —H |
| 74 | —C(O)CH$_2$CH$_2$— | 2-chlorophenyl | —CH$_2$CH$_3$ | —H |
| 75 | —C(O)CH$_2$CH$_2$— | 3-chlorophenyl | —CH$_2$CH$_3$ | —H |
| 76 | —C(O)CH$_2$CH$_2$— | 4-chlorophenyl | —CH$_2$CH$_3$ | —H |
| 77 | —C(O)CH$_2$CH$_2$— | 2,3-dichlorophenyl | —CH$_2$CH$_3$ | —H |
| 78 | —C(O)CH$_2$CH$_2$— | 3,4-dichlorophenyl | —CH$_2$CH$_3$ | —H |
| 79 | —C(O)CH$_2$CH$_2$— | 3,5-dichlorophenyl | —CH$_2$CH$_3$ | —H |
| 80 | —C(O)CH$_2$CH$_2$— | 2-hydroxyphenyl | —CH$_2$CH$_3$ | —H |
| 81 | —C(O)CH$_2$CH$_2$— | 3-hydroxyphenyl | —CH$_2$CH$_3$ | —H |
| 82 | —C(O)CH$_2$CH$_2$— | 4-hydroxyphenyl | —CH$_2$CH$_3$ | —H |
| 83 | —C(O)CH$_2$CH$_2$— | 2-methoxyphenyl | —CH$_2$CH$_3$ | —H |
| 84 | —C(O)CH$_2$CH$_2$— | 3-methoxyphenyl | —CH$_2$CH$_3$ | —H |
| 85 | —C(O)CH$_2$CH$_2$— | 4-methoxyphenyl | —CH$_2$CH$_3$ | —H |
| 86 | —C(O)CH$_2$CH$_2$— | 2,3-dimethoxyphenyl | —CH$_2$CH$_3$ | —H |
| 87 | —C(O)CH$_2$CH$_2$— | 3,4-dimethoxyphenyl | —CH$_2$CH$_3$ | —H |
| 88 | —C(O)CH$_2$CH$_2$— | 3,5-dimethoxyphenyl | —CH$_2$CH$_3$ | —H |

The compounds encompassed within the first aspect of Category I of the present disclosure can be prepared by the procedure outlined in Scheme I and described in Example 1 herein below.

Scheme I

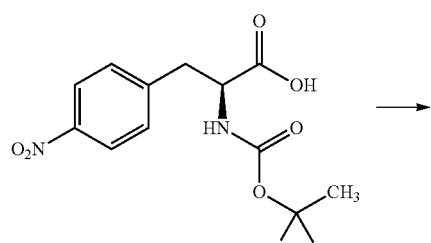

Reagents and conditions: (a) (i) (iso-butyl)OCOCl, NMM, DMF; 0° C., 20 min. (ii) NH$_3$; 0° C. for 30 min.

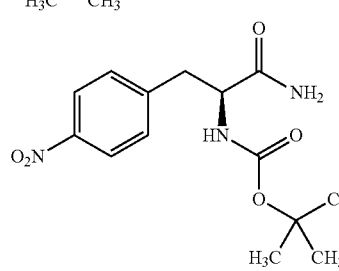

1

Reagents and conditions: (b) Lawesson's reagent, THF; rt, 3 hr.

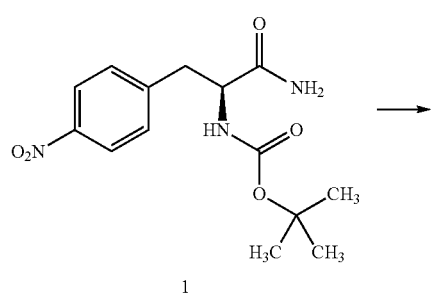

2

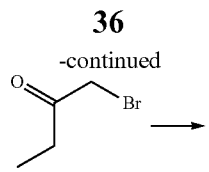

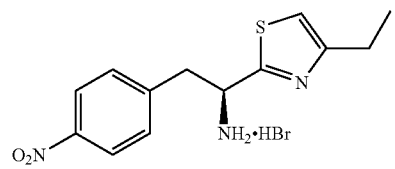

3

Reagents and conditions: (c) CH$_3$CN; reflux, 2 hr.

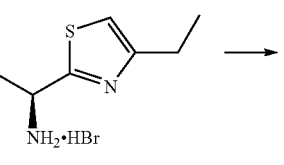

3

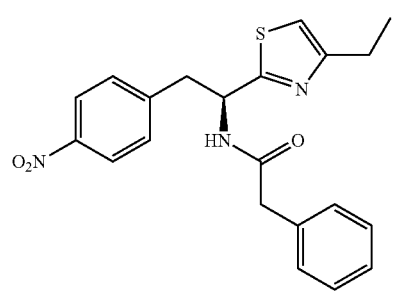

4

Reagents and conditions: (d) C$_6$H$_4$CO$_2$H, EDCI, HOBt, DIPEA, DMF; rt, 18 hr.

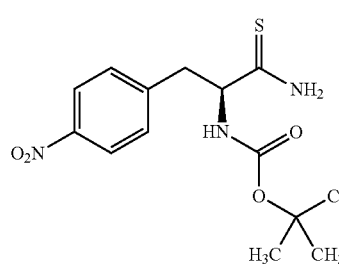

4

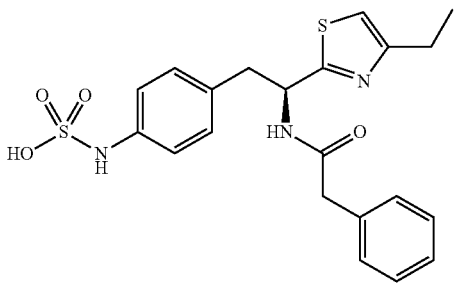

5

Reagents and conditions: (e) (i) H$_2$:Pd/C, MeOH; (ii) SO$_3$-pyridine, NH$_4$OH, rt, 18 hr.

Example 1

{4-[2-(S)-(4-Ethylthiazol-2-yl)-2-(2-phenylacetyla-mido)ethyl]phenyl}sulfamic acid (5)

Preparation of [1-(S)-carbamoyl-2-(4-nitrophenyl)ethyl] carbamic acid tert-butyl ester (1): To a 0° C. solution of 2-(S)-tert-butoxycarbonylamino-3-(4-nitrophenyl)-propionic acid and N-methylmorpholine (1.1 mL, 9.65 mmol) in DMF (10 mL) is added dropwise iso-butyl chloroformate (1.25 mL, 9.65 mmol). The mixture is stirred at 0° C. for 20 minutes. after which $NH_3$ (g) is passed through the reaction mixture for 30 minutes at 0° C. The reaction mixture is concentrated and the residue dissolved in EtOAc, washed successively with 5% citric acid, water, 5% $NaHCO_3$, water and brine, dried ($Na_2SO_4$), filtered and concentrated in vacuo to a residue that is triturated with a mixture of EtOAc/petroleum ether to provide 2.2 g (74% yield) of the desired product as a white solid.

Preparation of [2-(4-nitrophenyl)-1-(S)-thiocarbamoyl-ethyl]carbamic acid tert-butyl ester (2): To a solution of [1-(S)-carbamoyl-2-(4-nitrophenyl)ethyl-carbamic acid tert-butyl ester, 1, (0.400 g, 1.29 mmol) in THF (10 mL) is added Lawesson's reagent (0.262 g. 0.65 mmol). The reaction mixture is stirred for 3 hours and concentrated to a residue that is purified over silica to provide 0.350 g (83% yield) of the desired product. $^1$H NMR (300 MHz, $CDCl_3$) δ 8.29 (s, 1H), 8.10 (d. J=8.4 Hz, 2H), 8.01 (s, 1H), 7.42 (d, J=8.4 Hz, 2H), 5.70 (d, J=7.2 Hz, 1H), 4.85 (d, J=7.2 Hz, 1H), 3.11-3.30 (m, 1H), 1.21 (s, 9H).

Preparation of 1-(S)-(4-ethylthiazol-2-yl)-2-(4-nitrophenyl)ethyl amine hydrobromide (3): A mixture of [2-(4-nitrophenyl)-1-(S)-thiocarbamoylethyl]-carbamic acid tert-butyl ester, 2, (10 g, 30.7 mmol) and 1-bromo-2-butanone (90%, 3.8 mL, 33.8 mmol) in $CH_3CN$ (500 mL) is refluxed for 18 hours. The reaction mixture is cooled to room temperature and diethyl ether is added to the solution and the precipitate which forms is removed by filtration to afford 7.47 g of the desired product. ESI+MS 278 (M+1).

Preparation of N-[1-(4-ethylthiazol-2-yl)-2-(4-nitrophenyl)ethyl]-2-phenyl-acetamide (4): To a solution of 1-(S)-(4-ethylthiazol-2-yl)-2-(4-nitrophenyl)ethyl amine hydrobromide, 3, (0.393 g, 1.1 mmol), phenylacetic acid (0.190 g, 1.4 mmol) and 1-hydroxybenzotriazole (HOBt) (0.094 g, 0.70 mmol) in DMF (10 mL) at 0°, is added 1-(3-dimethylamino-propyl)-3-ethylcarbodiimide (EDCI) (0.268 g, 1.4 mmol) followed by triethylamine (0.60 mL, 4.2 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous $NaHCO_3$, water and brine, and dried over $Na_2SO_4$. The solvent is removed in vacuo to afford 0.260 g (60% yield) of the desired product which is used without further purification. ESI+MS 396 (M+1).

Preparation of {4-[2-(S)-(4-ethylthiazol-2-yl)-2-(2-phenylacetylamido)ethyl]-phenyl}sulfamic acid (5): N-[1-(4-ethylthiazol-2-yl)-2-(4-nitrophenyl)ethyl]-2-phenyl-acetamide, 4, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with $SO_3$-pyridine (0.177 g, 1.23). The reaction is stirred at room temperature for 5 minutes after which a 7% solution of $NH_4OH$ (10 mL) is added. The mixture is then concentrated and the resulting residue is purified by reverse phase chromatography to afford 0.136 g of the desired product as the ammonium salt. $^1$H NMR ($CD_3OD$) δ 8.60 (d, 1H, J=8.1 Hz), 7.33-7.23 (m, 3H), 7.16-7.00 (m, 6H), 5.44-5.41 (m, 1H), 3.28 (1H, A of ABX, obscured by solvent), 3.03 (1H, B of ABX, J=14.1, 9.6 Hz), 2.80 (q, 2H, J=10.5, 7.8 Hz) 1.31 (t, 3H, J=4.6 Hz).

The following is a general procedure for isolating the final compound as a free acid.

Reduction of the aryl nitro group to free a amine:

To a Parr hydrogenation vessel is charged the nitro compound [for example, intermediate 4] (1.0 eq) and Pd/C (10% Pd on C, 50% wet, Degussa-type E101 NE/W, 2.68 g, 15 wt %) as solids. MeOH (15 mL/g) is added to provide a suspension. The vessel is put on a Parr hydrogenation apparatus. The vessel is submitted to a fill/vacuum evacuate process with $N_2$ (3×20 psi) to inert, followed by the same procedure with $H_2$ (3×40 psi). The vessel is filled with $H_2$ and the vessel is shaken under 40 psi $H_2$ for ~40 hr. The vessel is evacuated and the atmosphere is purged with $N_2$ (5×20 psi). An aliquot is filtered and analyzed by HPLC to insure complete conversion. The suspension is filtered through a pad of CELITE™ to remove the catalyst, and the homogeneous yellow filtrate is concentrated by rotary evaporation to afford the desired product which is used without further purification.

Preparation of free sulfamic acid: A 100 mL RBF is charged with the free amine (1.0 eq) prepared in the step described herein above. Acetonitrile (5 mL/g) is added and the yellow suspension which is typically yellow to orange in color is stirred at room temperature. A second 3-necked 500 mL RBF is charged with $SO_3$. pyr (1.4 eq) and acetonitrile (5 mL/g) and the suspension is stirred at room temperature. Both suspensions are gently heated until the reaction solution containing the amine becomes orange to red-orange in color (typically at about 40-45° C.). This substrate containing solution is poured in one portion into the stirring suspension of $SO_3$. pyr at 35° C. The resulting opaque mixture is stirred vigorously while allowed to slowly cool to room temperature. After stirring for 45 min, or once the reaction is determined to be complete by HPLC, water (20 mL/g) is added to the colored suspension to provide a homogeneous solution having a pH of approximately 2.4. Concentrated $H_3PO_4$ is added slowly to lower the pH to approximately 1.4. During this pH adjustment, an off-white precipitate typically forms and the solution is stirred at room temperature for an additional hour. The suspension is filtered and the filter cake is washed with the filtrate. The filter cake is air-dried overnight to afford the desired product as the free acid.

The following are non-limiting examples of the first aspect of Category I of the present disclosure.

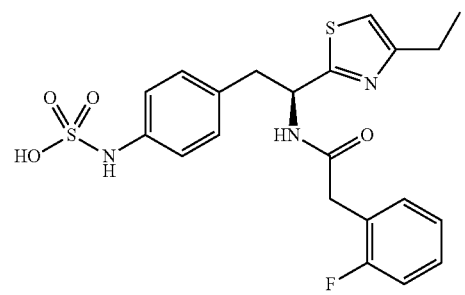

(S)-4-(2-(4-Ethylthiazol-2-yl)-2-(2-(2-fluorophenyl)ac-etamido)ethyl)phenyl-sulfamic acid: $^1$H NMR ($CD_3OD$) δ 8.65 (d, 1H, J=8.4 Hz), 7.29-7.15 (m, 1H), 7.13-7.03 (m, 7H), 5.46-5.42 (m, 1H), 3.64-3.51 (m, 2H), 3.29 (1H), 3.04 (1H, B of ABX, J=13.8, 9.6 Hz), 2.81 (q, 2H, J=15.6, 3.9 Hz), 1.31 (t, 3H, J=7.8 Hz). $^{19}$F NMR (CD$_3$OD) δ 43.64.

(S)-4-(2-(4-Ethylthiazol-2-yl)-2-(2-(2-fluorophenyl)acetamido)ethyl)phenyl-sulfamic acid

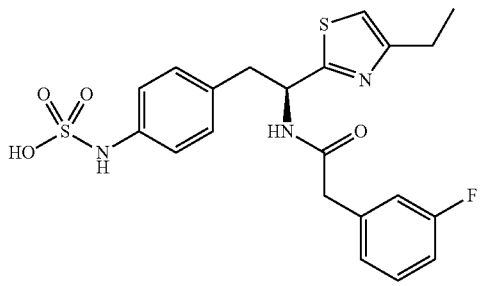

(S)-4-(2-(4-Ethylthiazol-2-yl)-2-(2-(3-fluorophenyl)acetamido)ethyl)phenyl-sulfamic acid: $^1$H NMR (CD$_3$OD) δ 8.74 (d, 1H, J=8.4 Hz), 7.32 (q, 1H, J=6.6, 14.2 Hz), 7.10-6.91 (m, 8H), 5.47-5.40 (m, 1H), 3.53 (s, 2H), 3.30 (1H), 3.11 (1H, B of ABX, J=9.6, 14.1 Hz), 2.80 (q, 2H, J=6.6, 15.1 Hz), 1.31 (t, 3H, J=7.8 Hz). $^{19}$F NMR δ 47.42.

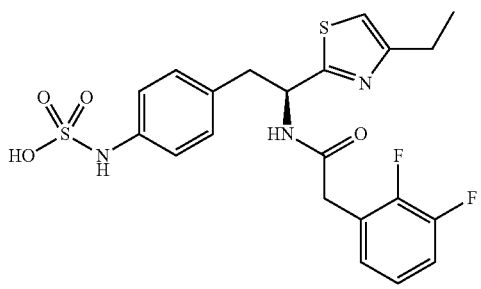

(S)-4-(2-(2-(2,3-Difluorophenyl)acetamido)-2-(4-ethylthiazol-2-yl)ethyl)phenyl-sulfamic acid: $^1$H NMR (CD$_3$OD) δ 7.16-7.05 (m, 5H), 6.85-6.80 (m, 1H), 5.48-5.43 (m, 1H), 3.63 (s, 2H), 3.38 (1H, A of ABX, obscured by solvent), 3.03 (1H), 2.80 (q, H, J=15.1, 7.8 Hz), 1.31 (t, 3H, J=7.5 Hz).

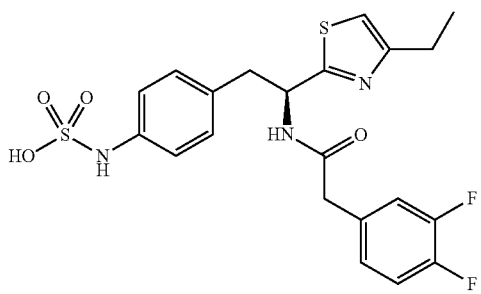

(S)-4-(2-(2-(3,4-Difluorophenyl)acetamido)-2-(4-ethylthiazol-2-yl)ethyl)phenyl-sulfamic acid: $^1$H NMR (CD$_3$OD) δ 8.75 (d, 1H, J=7.8 Hz), 7.23-7.04 (m, 6H), 6.88-6.84 (m, 1H), 5.44-5.40 (m, 1H), 3.49 (s, 2H), 3.34 (1H), 3.02 (1H, B of ABX, J=14.1, 9.9 Hz), 2.80 (q, 2H, J=15.1, 7.8 Hz), 1.31 (t, 1H, J=7.5 Hz). $^{19}$F NMR (CD$_3$OD) δ 22.18, 19.45.

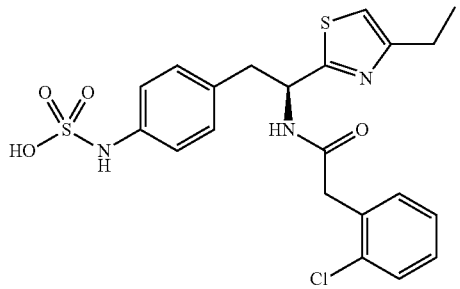

(S)-4-(2-(2-(2-Chlorophenyl)acetamido)-2-(4-ethylthiazol-2-yl)ethyl)phenyl-sulfamic acid: $^1$H NMR (CD3OD) δ 7.39-7.36 (m, 1H), 7.27-7.21 (m, 2H), 7.15-6.98 (m, 5H), 5.49-5.44 (m, 1H), 3.69 (d, 2H, J=11.7 Hz), 3.32 (1H), 3.04 (1H, B of ABX, J=9.3, 13.9 Hz), 2.80 (q, 2H, J=7.8, 15.3 Hz), 1.31 (t, 3H, J=7.5 Hz).

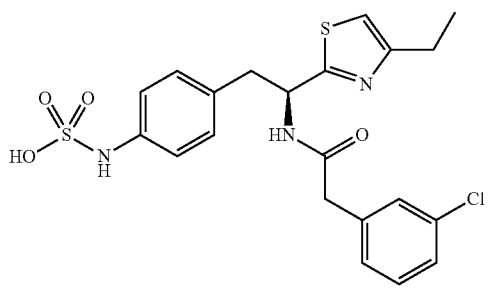

(S)-4-(2-(2-(3-Chlorophenyl)acetamido)-2-(4-ethylthiazol-2-yl)ethyl)phenyl-sulfamic acid: $^1$H NMR (CD3OD) δ 7.33-7.23 (m, 3H), 7.13-7.03 (m, 5H), 5.43 (q, 1H, J=5.1, 9.6 Hz), 3.51 (s, 2H), 3.29 (1H), 3.03 (1H, B of ABX, J=9.9, 14.1 Hz), 2.80 (q, 2H, J=7.5, 15 Hz), 1.31 (t, 3H, J=7.8 Hz).

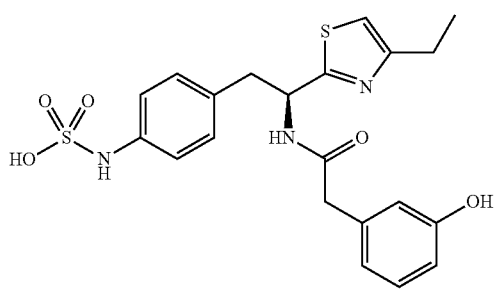

(S)-4-(2-(4-Ethylthiazol-2-yl)-2-(2-(3-hydroxyphenyl)acetamido)ethyl)phenyl-sulfamic acid: $^1$H NMR (CD$_3$OD) δ 7.16-7.08 (m, 3H), 7.03-7.00 (m, 3H), 6.70-6.63 (m, 2H), 5.42-5.40 (m, 1H), 3.44 (s, 2H), 3.28 (1H, A of ABX, obscured by solvent), 3.04 (B of ABX, J=14.1, 9.6 Hz), 2.89 (q, 2H, J=15, 7.5 Hz), 1.31 (t, 3H, J=7.5 Hz).

2.58-2.76 (m, 3H), 2.98 (q, 2H, J=13.8, 7.2 Hz), 1.29 (t, 3H, J=8.7 Hz).

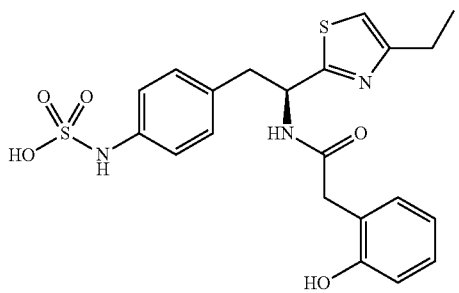

(S)-4-(2-(4-Ethylthiazol-2-yl)-2-(2-(2-methoxyphenyl) acetamido)ethyl)phenyl-sulfamic acid: $^1$H NMR (CD$_3$OD) δ 8.00 (d, 1H, J=7.8 Hz), 7.26 (t, 1H, J=13.2 Hz), 7.09-7.05 (m, 4H), 7.01 (s, 1H), 6.91-6.89 (m, 4H), 5.44-5.39 (m, 1H), 3.71 (s, 3H), 3.52 (s, 2H), 3.26 (1H, A of ABX, J=14.1, 5.1 Hz), 3.06 (1H B of ABX, J=13.8, 8.4 Hz), 2.80 (q, 2H, J=8.1, 15.6 Hz), 1.31 (t, 3H, J=1.2 Hz).

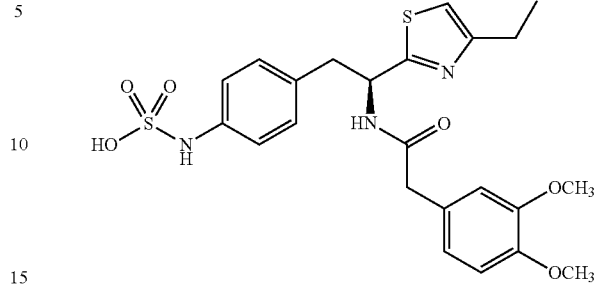

(S)-4-(2-(2-(3,4-Dimethoxyphenyl)acetamido)-2-(4-ethylthiazol-2-yl)ethyl)-phenylsulfamic acid: $^1$H NMR (CD$_3$OD) δ 7.12-7.03 (m, 3H), 6.91 (d, 1H, J=8.4 Hz), 6.82 (s, 1H), 6.66 (d, 1H, J=2.1 Hz), 6.63 (d, 1H, J=2.1 Hz), 5.43 (m, 1H), 3.84 (s, 3H), 3.80 (s, 3H), 3.45 (s, 2H), 3.30 (1H), 3.03 (1H, B of ABX, J=14.1, 9.6 Hz), 2.79 (q, 2H, J=15.1, 7.2 Hz), 1.30 (t, 3H, J=7.2 Hz).

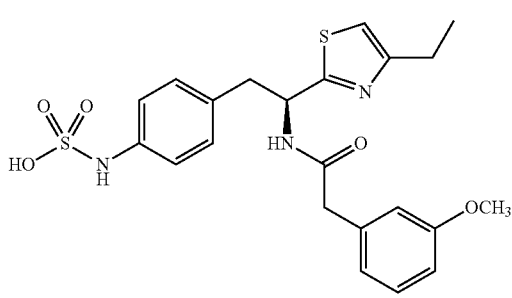

(S)-4-{2-(4-Ethylthiazol-2-yl)-2-[2-(3-methoxyphenyl) acetamido]ethyl}phenyl-sulfamic acid: $^1$H NMR (CD$_3$OD) δ 8.58 (d, 1H, J=8.1 Hz), 7.21 (t, 1H, J=7.8 Hz), 7.12-7.02 (m, 4H), 6.81 (s, 2H), 6.72 (d, 1H, J=7.5 Hz), 5.45-5.40 (m, 1H), 3.79 (s, 3H), 3.50 (s, 2H), 3.29 (1H, A of ABX, obscured by solvent), 3.08 (1H, B of ABX, J=11.8, 5.1 Hz), 2.80 (q, 2H, J=15, 7.5 Hz), 1.31 (t, 3H, J=6.6 Hz).

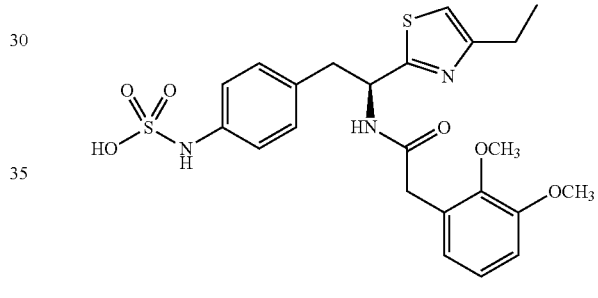

(S)-4-(2-(2-(2,3-Dimethoxyphenyl)acetamido)-2-(4-ethylthiazol-2-yl)ethyl)-phenylsulfamic acid: $^1$H NMR (CD$_3$OD) δ 8.31 (d, 1H, J=7.8 Hz), 7.11-6.93 (m, 6H), 6.68 (d, 1H, J=7.5 Hz), 5.49-5.40 (m, 1H), 3.87 (s, 3H), 3.70 (s, 3H), 3.55 (s, 2H), 3.26 (1H, A of ABX, obscured by solvent), 3.06 (1H, B of ABX, J=13.9, 9 Hz), 2.80 (q, 2H, J=14.8, 7.5 Hz), 1.31 (t, 3H, J=7.5 Hz).

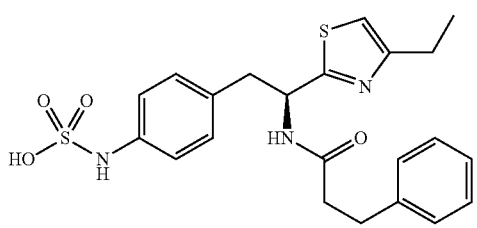

(S)-4-(2-(4-Ethylthiazol-2-yl)-2-(3-phenylpropanamido) ethyl)phenylsulfamic acid: $^1$H NMR (CD$_3$OD) δ 8.56 (d, 1H, J=8.4 Hz), 7.25-6.98 (m, 9H), 5.43-5.38 (m, 1H), 3.26 (1H, A of ABX, J=14.1, 9.6 Hz), 2.97 (1H, B of ABX, J=10.9, 3 Hz),

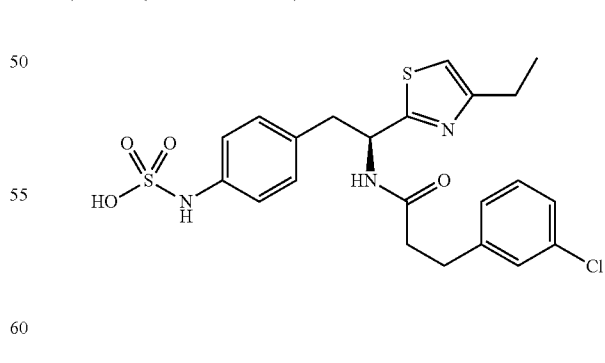

(S)-4-(2-(3-(3-Chlorophenyl)propanamido)-2-(4-ethylthiazol-2-yl)ethyl)phenyl-sulfamic acid: $^1$H NMR (CD3OD) δ 7.27-7.18 (m, 3H), 7.13-7.08 (m, 5H), 7.01 (s, 1H), 5.39 (q, 1H, J=5.1, 9.4 Hz), 3.28 (1H, A of ABX, J=5.1, 14.1 Hz), 2.97 (1H, B of ABX, J=9.3, 13.9 Hz), 2.88-2.76 (m, 4H), 2.50 (t, 2H, J=8.1 Hz), 1.31 (t, 3H, J=7.8 Hz).

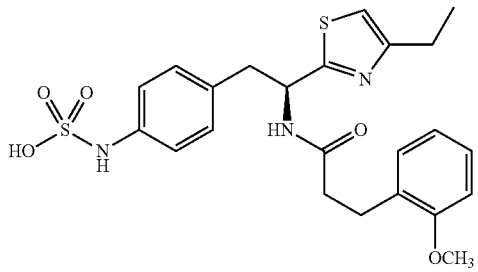

(S)-4-(2-(4-Ethylthiazol-2-yl)-2-(3-(2-methoxyphenyl)propanamido)ethyl)phenyl-sulfamic acid: ¹H NMR (CD₃OD) δ 7.18-7.08 (m, 6H), 6.92 (d, 1H, J=8.1 Hz), 6.82 (t, 1H, J=7.5 Hz), 5.40-5.35 (m, 1H), 3.25 (1H, A of ABX, J=15, 5.4 Hz), 3.00 (1H, B of ABX, J=10.5, 7.5 Hz), 2.88-2.76 (m, 4H), 2.47 (q, 2H, J=9.1, 6 Hz), 1.31 (t, 3H, J=7.8 Hz).

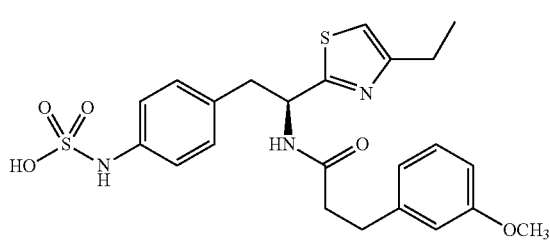

(S)-4-(2-(4-Ethylthiazol-2-yl)-2-(3-(3-methoxyphenyl)propanamido)ethyl)phenyl-sulfamic acid: ¹H NMR (CD₃OD) δ 7.19-7.00 (m, 5H), 6.75 (s, 1H), 6.73 (s, 1H), 5.42-5.37 (m, 1H), 3.76 (s, 3H), 3.25 (1H, A of ABX, J=13.9, 5.4 Hz), 2.98 (1H, B of ABX, J=14.1, 9.6 Hz), 2.86-2.75 (m, 4H), 2.48 (q, 2H, J=11.7, 1.2 Hz), 1.31 (t, 3H, J=7.5 Hz).

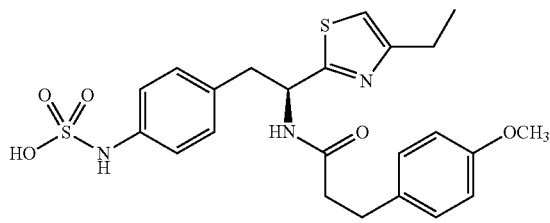

(S)-4-(2-(4-Ethylthiazol-2-yl)-2-(3-(4-methoxyphenyl)propanamido)ethyl)phenyl-sulfamic acid: ¹H NMR (CD₃OD) δ 7.13-6.99 (m, 7H), 6.82-6.78 (m, 2H), 5.42-5.37 (m, 1H), 3.33 (s, 3H), 3.23 (1H), 2.97 (1H, B of ABX, J=13.3, 11.4 Hz), 2.83-2.75 (m, 4H), 2.49 (q, 2H, J=6.4, 3.3 Hz), 1.31 (t, 3H, J=7.5 Hz).

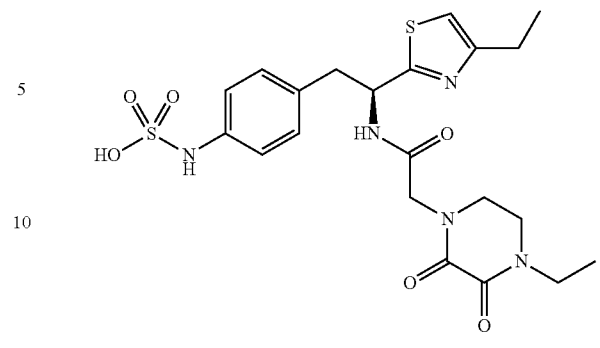

(S)-4-{2-[2-(4-Ethyl-2,3-dioxopiperazin-1-yl)acetamido]-2-(4-ethylthiazol-2-yl)ethyl}phenylsulfamic acid: ¹H NMR (CD₃OD) δ 7.14 (s, 4H), 7.08 (s, 1H), 5.56-5.51 (m, 1H), 4.34 (d, 2H, J=16.2 Hz), 3.88 (d, 2H, J=17.6 Hz), 3.59-3.40 (m, 3H), 3.26-3.14 (m, 3H), 2.98 (1H, B of ABX, J=10.8, 13.9 Hz), 2.82 (q, 2H, J=6.9, 15 Hz), 1.32 (t, 3H, J=7.5 Hz), 1.21 (t, 3H, J=7.2 Hz).

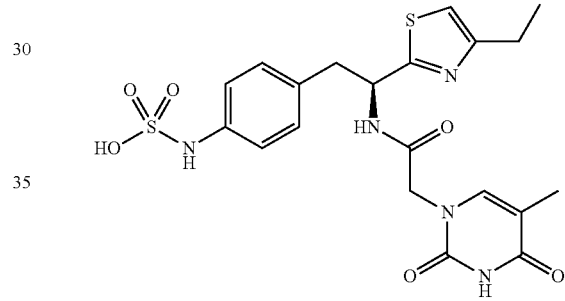

(S)-4-{2-(4-Ethylthiazol-2-yl)-2-[2-(5-methyl-2,4-dioxo-3,4-dihydropyrimidin-1(2H)-yl)acetamido]ethyl}phenylsulfamic acid: ¹H(CD₃OD): δ 7.13 (s, 1H), 7.06-7.02 (m, 4H), 6.95 (s, 1H), 5.42-5.31 (m, 1H), 4.43-4.18 (dd, 2H, J=16.5 Hz), 3.24-2.93 (m, 2H), 2.74-2.69 (q, 2H, J=7.3 Hz), 1.79 (s, 3H), 1.22 (t, 3H, J=7.5 Hz).

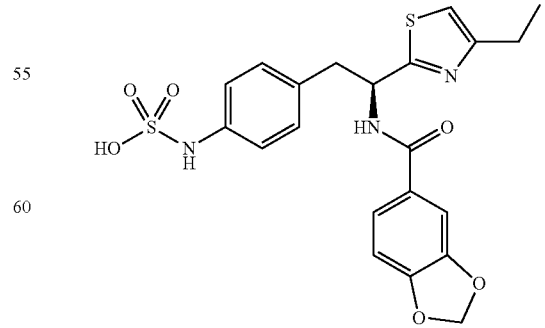

(S)-4-[2-(benzo[d][1,3]dioxole-5-carboxamido)-2-(4-ethylthiazol-2-yl)ethyl]-phenylsulfamic acid: $^1$H NMR (CD$_3$OD) δ 7.25 (d, 1H, J=6.5 Hz), 7.13 (s, 1H), 7.06 (d, 2H, J=8.5 Hz), 7.00 (d, 2H, J=8.5 Hz), 6.91 (s, 1H), 6.76 (d, 1H, J=8.1 Hz), 5.90 (s, 2H), 5.48 (q, 1H, J=5.0 Hz), 3.32-3.24 (m, 2H), 3.07-2.99 (m, 2H), 2.72 (q, 2H, J=7.5 Hz), 1.21 (t, 3H, J=7.5 Hz).

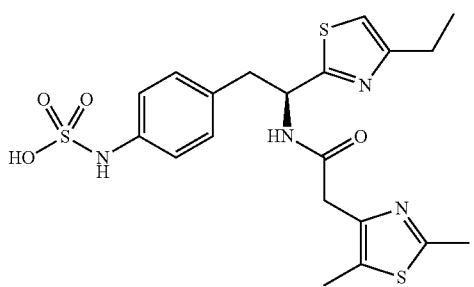

(S)-4-{2-[2-(2,5-Dimethylthiazol-4-yl)acetamido]-2-(4-ethylthiazol-2-yl)ethyl}-phenylsulfamic acid: $^1$H(CD$_3$OD): δ 7.10-7.01 (m, 5H), 5.41 (t, 1H, J=6.9 Hz), 3.58 (s, 2H), 3.33-3.01 (m, 2H), 2.82-2.75 (q, 2H, J=7.5 Hz), 2.59 (s, 3H), 2.23 (s, 3H), 1.30 (t, 3H, J=7.5 Hz).

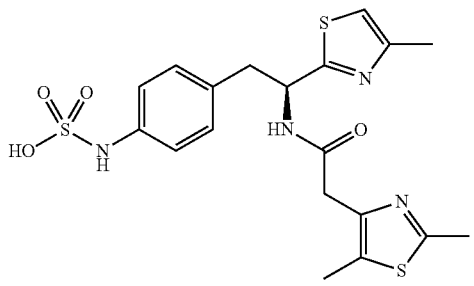

(S)-4-{2-[2-(2,4-Dimethylthiazol-5-yl)acetamido]-2-(4-methylthiazol-2-yl)ethyl}phenylsulfamic acid: $^1$H(CD$_3$OD): δ 8.71-8.68 (d, 1H, J=8.4 Hz), 7.10-7.03 (m, 4H), 7.01 (s, 1H), 5.41 (m, 1H), 3.59 (s, 1H), 3.34-2.96 (m, 2H), 2.59 (s, 3H), 2.40 (s, 3H), 2.23 (s, 3H).

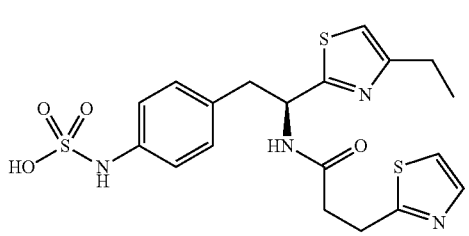

(S)-4-{2-(4-Ethylthiazol-2-yl)-2-[3-(thiazol-2-yl)propanamido]ethyl}phenyl-sulfamic acid: $^1$H(CD$_3$OD): δ 7.67-7.65 (m, 1H), 7.49-7.47 (m, 1H), 7.14-7.08 (m, 4H), 7.04 (s, 1H), 5.46-5.41 (q, 1H, J=5.1 Hz), 3.58 (s, 2H), 3.30-3.25 (m, 3H), 3.02-2.67 (m, 5H), 1.31 (t, 3H, J=7.5 Hz).

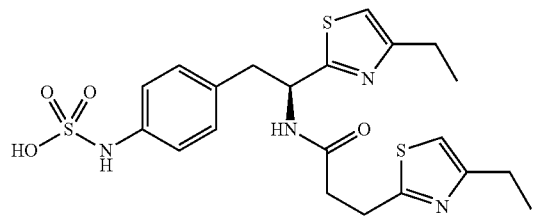

(S)-4-{2-(4-Ethylthiazol-2-yl)-2-[2-(4-ethylthiazol-2-yl)acetamido]ethyl}phenyl-sulfamic acid: $^1$H(CD$_3$OD) δ 7.04-6.91 (m, 6H), 5.32 (t, 1H, J=5.4 Hz), 3.25-2.90 (m, 2H), 2.71-2.61 (m, 4H) 1.93 (s, 2H) 1.22-1.14 (m, 6H).

The second aspect of Category I of the present disclosure relates to 2-(thiazol-4-yl) compounds having the formula:

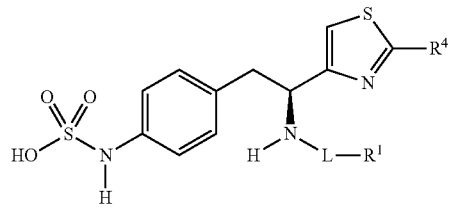

wherein R$^1$, R$^4$, and L are further defined herein in Table II herein below.

TABLE II

| No. | L | R$^1$ | R$^4$ |
|---|---|---|---|
| 89 | —C(O)CH$_2$— | phenyl | methyl |
| 90 | —C(O)CH$_2$— | phenyl | ethyl |
| 91 | —C(O)CH$_2$— | phenyl | phenyl |
| 92 | —C(O)CH$_2$— | phenyl | thiophene-2-yl |
| 93 | —C(O)CH$_2$— | phenyl | thiazol-2-yl |
| 94 | —C(O)CH$_2$— | phenyl | oxazol-2-yl |
| 95 | —C(O)CH$_2$— | phenyl | isoxazol-3-yl |
| 96 | —C(O)CH$_2$— | 3-chlorophenyl | methyl |
| 97 | —C(O)CH$_2$— | 3-chlorophenyl | ethyl |
| 98 | —C(O)CH$_2$— | 3-chlorophenyl | phenyl |
| 99 | —C(O)CH$_2$— | 3-chlorophenyl | thiophene-2-yl |
| 100 | —C(O)CH$_2$— | 3-chlorophenyl | thiazol-2-yl |
| 101 | —C(O)CH$_2$— | 3-chlorophenyl | oxazol-2-yl |
| 102 | —C(O)CH$_2$— | 3-chlorophenyl | isoxazol-3-yl |
| 103 | —C(O)CH$_2$— | 3-methoxyphenyl | methyl |
| 104 | —C(O)CH$_2$— | 3-methoxyphenyl | ethyl |
| 105 | —C(O)CH$_2$— | 3-methoxyphenyl | phenyl |
| 106 | —C(O)CH$_2$— | 3-methoxyphenyl | thiophene-2-yl |
| 107 | —C(O)CH$_2$— | 3-methoxyphenyl | thiazol-2-yl |
| 108 | —C(O)CH$_2$— | 3-methoxyphenyl | oxazol-2-yl |
| 109 | —C(O)CH$_2$— | 3-methoxyphenyl | isoxazol-3-yl |
| 110 | —C(O)CH$_2$— | 3-fluorophenyl | methyl |
| 111 | —C(O)CH$_2$— | 3-fluorophenyl | ethyl |
| 112 | —C(O)CH$_2$— | 3-fluorophenyl | phenyl |
| 113 | —C(O)CH$_2$— | 3-fluorophenyl | thiophene-2-yl |
| 114 | —C(O)CH$_2$— | 3-fluorophenyl | thiazol-2-yl |
| 115 | —C(O)CH$_2$— | 3-fluorophenyl | oxazol-2-yl |
| 116 | —C(O)CH$_2$— | 3-fluorophenyl | isoxazol-3-yl |
| 117 | —C(O)CH$_2$— | 2,5-dimethylthiazol-4-yl | methyl |
| 118 | —C(O)CH$_2$— | 2,5-dimethylthiazol-4-yl | ethyl |
| 119 | —C(O)CH$_2$— | 2,5-dimethylthiazol-4-yl | phenyl |
| 120 | —C(O)CH$_2$— | 2,5-dimethylthiazol-4-yl | thiophene-2-yl |
| 121 | —C(O)CH$_2$— | 2,5-dimethylthiazol-4-yl | thiazol-2-yl |
| 122 | —C(O)CH$_2$— | 2,5-dimethylthiazol-4-yl | oxazol-2-yl |
| 123 | —C(O)CH$_2$— | 2,5-dimethylthiazol-4-yl | isoxazol-3-yl |

TABLE II-continued

| No. | L | R¹ | R⁴ |
|---|---|---|---|
| 124 | —C(O)CH₂— | 2,4-dimethylthiazol-5-yl | methyl |
| 125 | —C(O)CH₂— | 2,4-dimethylthiazol-5-yl | ethyl |
| 126 | —C(O)CH₂— | 2,4-dimethylthiazol-5-yl | phenyl |
| 127 | —C(O)CH₂— | 2,4-dimethylthiazol-5-yl | thiophene-2-yl |
| 128 | —C(O)CH₂— | 2,4-dimethylthiazol-5-yl | thiazol-2-yl |
| 129 | —C(O)CH₂— | 2,4-dimethylthiazol-5-yl | oxazol-2-yl |
| 130 | —C(O)CH₂— | 2,4-dimethylthiazol-5-yl | isoxazol-3-yl |
| 131 | —C(O)CH₂— | 4-ethylthiazol-2-yl | methyl |
| 132 | —C(O)CH₂— | 4-ethylthiazol-2-yl | ethyl |
| 133 | —C(O)CH₂— | 4-ethylthiazol-2-yl | phenyl |
| 134 | —C(O)CH₂— | 4-ethylthiazol-2-yl | thiophene-2-yl |
| 135 | —C(O)CH₂— | 4-ethylthiazol-2-yl | thiazol-2-yl |
| 136 | —C(O)CH₂— | 4-ethylthiazol-2-yl | oxazol-2-yl |
| 137 | —C(O)CH₂— | 4-ethylthiazol-2-yl | isoxazol-3-yl |
| 138 | —C(O)CH₂— | 3-methyl-1,2,4-oxadiazol-5-yl | methyl |
| 139 | —C(O)CH₂— | 3-methyl-1,2,4-oxadiazol-5-yl | ethyl |
| 140 | —C(O)CH₂— | 3-methyl-1,2,4-oxadiazol-5-yl | phenyl |
| 141 | —C(O)CH₂— | 3-methyl-1,2,4-oxadiazol-5-yl | thiophene-2-yl |
| 142 | —C(O)CH₂— | 3-methyl-1,2,4-oxadiazol-5-yl | thiazol-2-yl |
| 143 | —C(O)CH₂— | 3-methyl-1,2,4-oxadiazol-5-yl | oxazol-2-yl |
| 144 | —C(O)CH₂— | 3-methyl-1,2,4-oxadiazol-5-yl | isoxazol-3-yl |
| 145 | —C(O)CH₂CH₂— | phenyl | methyl |
| 146 | —C(O)CH₂CH₂— | phenyl | ethyl |
| 147 | —C(O)CH₂CH₂— | phenyl | phenyl |
| 148 | —C(O)CH₂CH₂— | phenyl | thiophene-2-yl |
| 149 | —C(O)CH₂CH₂— | phenyl | thiazol-2-yl |
| 150 | —C(O)CH₂CH₂— | phenyl | oxazol-2-yl |
| 151 | —C(O)CH₂CH₂— | phenyl | isoxazol-3-yl |
| 152 | —C(O)CH₂CH₂— | 3-chlorophenyl | methyl |
| 153 | —C(O)CH₂CH₂— | 3-chlorophenyl | ethyl |
| 154 | —C(O)CH₂CH₂— | 3-chlorophenyl | phenyl |
| 155 | —C(O)CH₂CH₂— | 3-chlorophenyl | thiophene-2-yl |
| 156 | —C(O)CH₂CH₂— | 3-chlorophenyl | thiazol-2-yl |
| 157 | —C(O)CH₂CH₂— | 3-chlorophenyl | oxazol-2-yl |
| 158 | —C(O)CH₂CH₂— | 3-chlorophenyl | isoxazol-3-yl |
| 159 | —C(O)CH₂CH₂— | 3-methoxyphenyl | methyl |
| 160 | —C(O)CH₂CH₂— | 3-methoxyphenyl | ethyl |
| 161 | —C(O)CH₂CH₂— | 3-methoxyphenyl | phenyl |
| 162 | —C(O)CH₂CH₂— | 3-methoxyphenyl | thiophene-2-yl |
| 163 | —C(O)CH₂CH₂— | 3-methoxyphenyl | thiazol-2-yl |
| 164 | —C(O)CH₂CH₂— | 3-methoxyphenyl | oxazol-2-yl |
| 165 | —C(O)CH₂CH₂— | 3-methoxyphenyl | isoxazol-3-yl |
| 166 | —C(O)CH₂CH₂— | 3-fluorophenyl | methyl |
| 167 | —C(O)CH₂CH₂— | 3-fluorophenyl | ethyl |
| 168 | —C(O)CH₂CH₂— | 3-fluorophenyl | phenyl |
| 169 | —C(O)CH₂CH₂— | 3-fluorophenyl | thiophene-2-yl |
| 170 | —C(O)CH₂CH₂— | 3-fluorophenyl | thiazol-2-yl |
| 171 | —C(O)CH₂CH₂— | 3-fluorophenyl | oxazol-2-yl |
| 172 | —C(O)CH₂CH₂— | 3-fluorophenyl | isoxazol-3-yl |
| 173 | —C(O)CH₂CH₂— | 2,5-dimethylthiazol-4-yl | methyl |
| 174 | —C(O)CH₂CH₂— | 2,5-dimethylthiazol-4-yl | ethyl |
| 175 | —C(O)CH₂CH₂— | 2,5-dimethylthiazol-4-yl | phenyl |
| 176 | —C(O)CH₂CH₂— | 2,5-dimethylthiazol-4-yl | thiophene-2-yl |
| 177 | —C(O)CH₂CH₂— | 2,5-dimethylthiazol-4-yl | thiazol-2-yl |
| 178 | —C(O)CH₂CH₂— | 2,5-dimethylthiazol-4-yl | oxazol-2-yl |
| 179 | —C(O)CH₂CH₂— | 2,5-dimethylthiazol-4-yl | isoxazol-3-yl |
| 180 | —C(O)CH₂CH₂— | 2,4-dimethylthiazol-5-yl | methyl |
| 181 | —C(O)CH₂CH₂— | 2,4-dimethylthiazol-5-yl | ethyl |
| 182 | —C(O)CH₂CH₂— | 2,4-dimethylthiazol-5-yl | phenyl |
| 183 | —C(O)CH₂CH₂— | 2,4-dimethylthiazol-5-yl | thiophene-2-yl |
| 184 | —C(O)CH₂CH₂— | 2,4-dimethylthiazol-5-yl | thiazol-2-yl |
| 185 | —C(O)CH₂CH₂— | 2,4-dimethylthiazol-5-yl | oxazol-2-yl |
| 186 | —C(O)CH₂CH₂— | 2,4-dimethylthiazol-5-yl | isoxazol-3-yl |
| 187 | —C(O)CH₂CH₂— | 4-ethylthiazol-2-yl | methyl |
| 188 | —C(O)CH₂CH₂— | 4-ethylthiazol-2-yl | ethyl |
| 189 | —C(O)CH₂CH₂— | 4-ethylthiazol-2-yl | phenyl |
| 190 | —C(O)CH₂CH₂— | 4-ethylthiazol-2-yl | thiophene-2-yl |
| 191 | —C(O)CH₂CH₂— | 4-ethylthiazol-2-yl | thiazol-2-yl |
| 192 | —C(O)CH₂CH₂— | 4-ethylthiazol-2-yl | oxazol-2-yl |
| 193 | —C(O)CH₂CH₂— | 4-ethylthiazol-2-yl | isoxazol-3-yl |
| 194 | —C(O)CH₂CH₂— | 3-methyl-1,2,4-oxadiazol-5-yl | methyl |
| 195 | —C(O)CH₂CH₂— | 3-methyl-1,2,4-oxadiazol-5-yl | ethyl |
| 196 | —C(O)CH₂CH₂— | 3-methyl-1,2,4-oxadiazol-5-yl | phenyl |
| 197 | —C(O)CH₂CH₂— | 3-methyl-1,2,4-oxadiazol-5-yl | thiophene-2-yl |
| 198 | —C(O)CH₂CH₂— | 3-methyl-1,2,4-oxadiazol-5-yl | thiazol-2-yl |
| 199 | —C(O)CH₂CH₂— | 3-methyl-1,2,4-oxadiazol-5-yl | oxazol-2-yl |
| 200 | —C(O)CH₂CH₂— | 3-methyl-1,2,4-oxadiazol-5-yl | isoxazol-3-yl |

The compounds encompassed within the second aspect of Category I of the present disclosure can be prepared by the procedure outlined in Scheme II and described in Example 2 herein below.

Scheme II

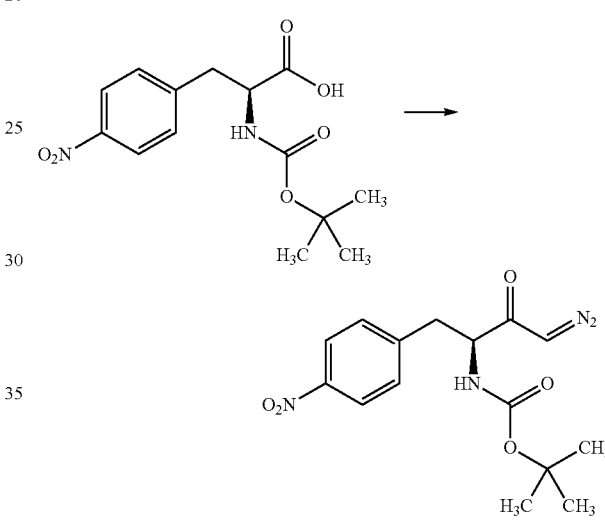

Reagents and conditions: (a) (i) (iso-butyl)OCOCl, Et₃N, THF; 0° C., 20 min. (ii) CH₂N₂; room temp for 3 hours.

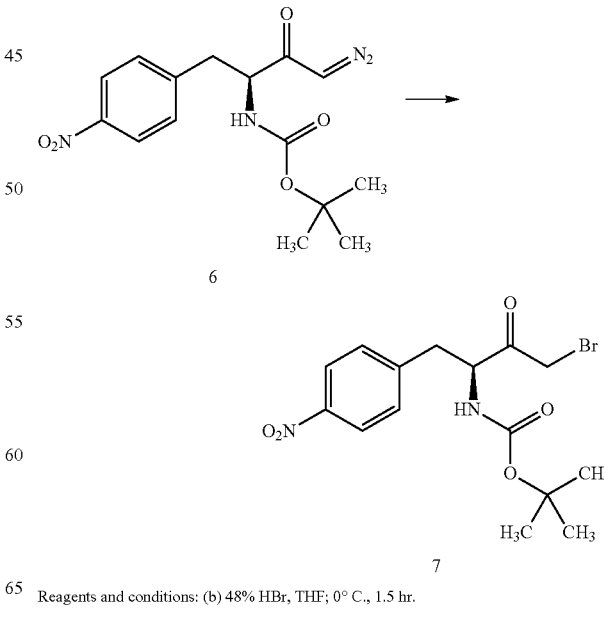

Reagents and conditions: (b) 48% HBr, THF; 0° C., 1.5 hr.

-continued

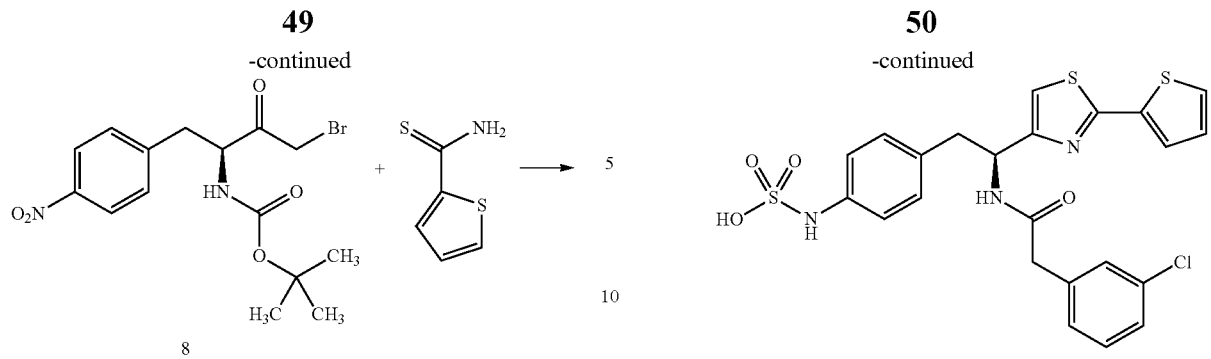

Reagents and conditions: (c) CH₃CN; reflux 5 hr.

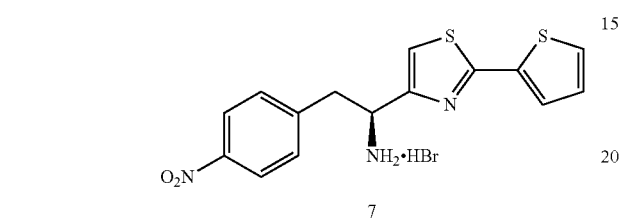

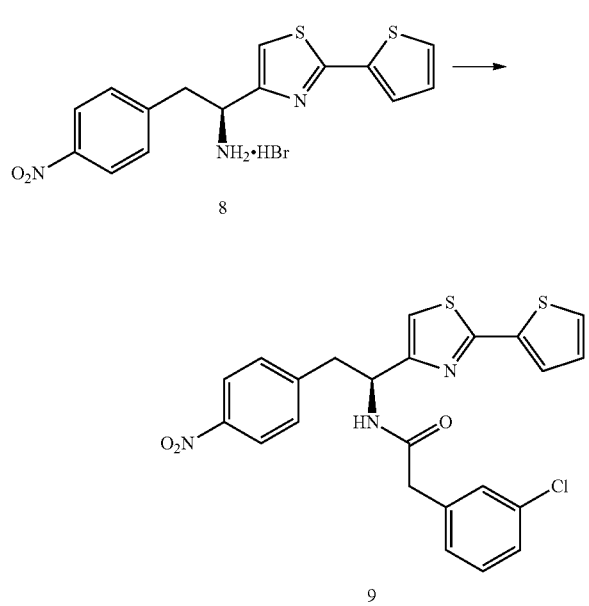

Reagents and conditions: (d) (3-Cl) C₆H₄CO₂H, EDCI, HOBt, DIPEA, DMF; rt, 18 hr.

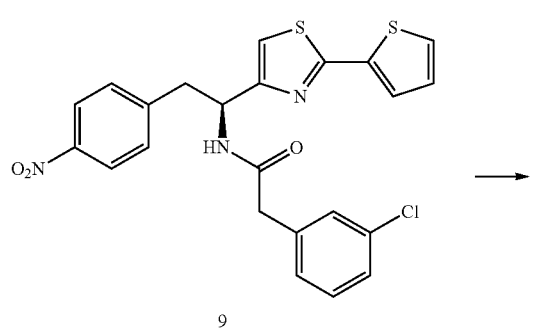

-continued

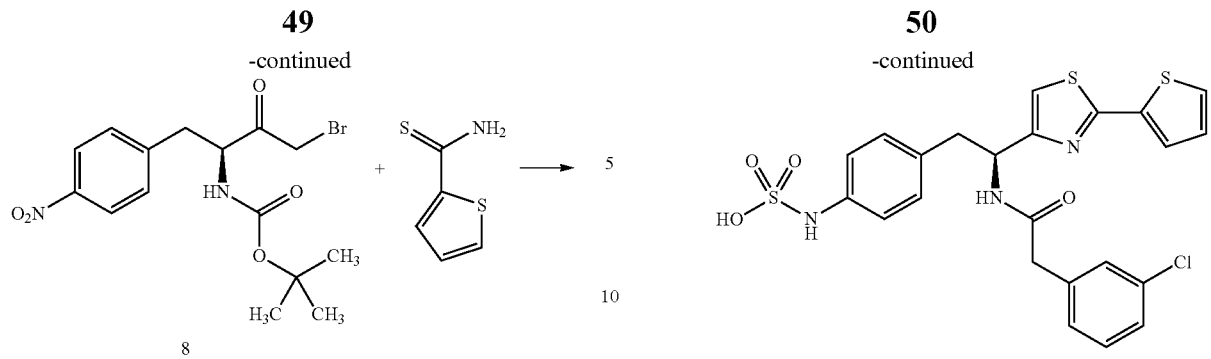

Reagents and conditions: (e) (i) H₂:Pd/C, MeOH; (ii) SO₃-pyridine, NH₄OH, rt, 18 hr.

Example 2

4-((S)-2-(2-(3-chlorophenyl)acetamido)-2-(2-(thiophene-2-yl)thiazol-4-yl)ethyl)phenylsulfamic acid (10)

Preparation of (S)-[3-diazo-1-(4-nitrobenzyl)-2-oxo-propyl]-carbamic acid tert-butyl ester (6): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by isobutyl chloroformate (0.57 mL, 4.4 mmol). The reaction mixture is stirred at 0° C. for 20 minutes and filtered. The filtrate is treated with an ether solution of diazomethane (~16 mmol) at 0° C. The reaction mixture is stirred at room temperature for 3 hours then concentrated in vacuo. The resulting residue is dissolved in EtOAc and washed successively with water and brine, dried (Na₂SO₄), filtered and concentrated. The residue is purified over silica (hexane/EtOAc 2:1) to afford 1.1 g (82% yield) of the desired product as a slightly yellow solid. ¹H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of (S)-tert-butyl 4-bromo-1-(4-nitrophenyl)-3-oxobutan-2-ylcarbamate (7): To a 0° C. solution of (S)-[3-diazo-1-(4-nitrobenzyl)-2-oxo-propyl]-carbamic acid tert-butyl ester, 6, (0.350 g, 1.04 mmol) in THF (5 mL) is added dropwise 48% aq. HBr (0.14 mL, 1.25 mmol). The reaction mixture is stirred at 0° C. for 1.5 hours then the reaction is quenched at 0° C. with sat. Na₂CO₃. The mixture is extracted with EtOAc (3×25 mL) and the combined organic extracts are washed with brine, dried (Na₂SO₄), filtered and concentrated to obtain 0.400 g of the product which is used in the next step without further purification. ¹H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of (S)-2-(4-nitrophenyl)-1-[(thiophene-2-yl)thiazol-4-yl]ethanamine hydrobromide salt (8): A mixture of (S)-tert-butyl 4-bromo-1-(4-nitrophenyl)-3-oxobutan-2-ylcarbamate, 7, (7.74 g, 20 mmol), and thiophene-2-carbothioic acid amide (3.14 g, 22 mmol) in CH₃CN (200 mL) is refluxed for 5 hours. The reaction mixture is cooled to room temperature and diethyl ether (50 mL) is added to the solution. The precipitate which forms is collected by filtration. The solid is dried under vacuum to afford 7.14 g (87% yield) of the desired product. ESI+MS 332 (M+1).

Preparation of 2-(3-chlorophenyl)-N-{(S)-2-(4-nitrophenyl)-1-[2-(thiophene-2-yl)thiazol-4-yl]ethyl}acetamide (9): To a solution of 2-(4-nitrophenyl)-1-(2-thiophene2-ylthiazol- 4-yl)ethylamine, 8, (0.41 g, 1 mmol) 3-chlorophenylacetic acid (0.170 g, 1 mmol) and 1-hydroxybenzotriazole (HOBt) (0.070 g, 0.50 mmol) in DMF (5 mL) at 0°, is added 1-(3-dimethylaminopropyl)-3-ethylcarbodiimide (EDCI) (0.190 g, 1 mmol) followed by triethylamine (0.42 mL, 3 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.290 g (60% yield) of the desired product which is used without further purification. ESI– MS 482 (M–1).

Preparation of {4-[2-(3-chlorophenyl)acetylamino]-2-(2-thiophen-2-ylthiazol-4-yl)ethyl]phenyl}sulfamic acid (10): 2-(3-chlorophenyl)-N-{(S)-2-(4-nitrophenyl)-1-[2-(thiophene2-yl)thiazol-4-yl]ethyl}acetamide, 9, (0.290 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue is purified by reverse phase chromatography to afford 0.078 g of the desired product as the ammonium salt. ¹H NMR (CD3OD) δ 7.61 (d, 1H, J=3.6 Hz), 7.58 (d, 1H, J=5.1 Hz), 7.41-7.35 (m, 1H), 7.28-7.22 (m, 2H), 7.18-6.98 (m, 6H), 5.33 (t, 1H, J=6.6 Hz), 3.70 (d, 2H, J=3.9 Hz), 3.23 (1H, A of ABX, J=6.6, 13.8 Hz), 3.07 (1H, B of ABX, J=8.1, 13.5 Hz).

The following are non-limiting examples of compounds encompassed within the second aspect of Category I of the present disclosure.

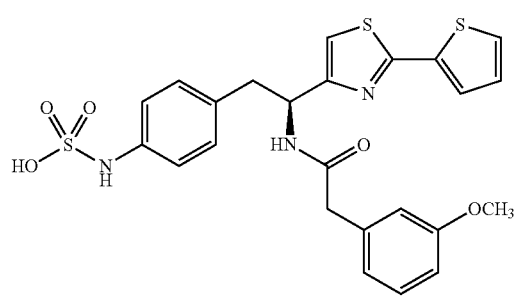

4-((S)-2-(2-(3-Methoxyphenyl)acetamido)-2-[2-(thiophene2-yl)thiazol-4-yl]ethyl)-phenylsulfamic acid: ¹H NMR (CD3OD) δ 8.35 (d, 1H, J=8.7 Hz), 7.61-7.57 (m, 2H), 7.25-7.20 (m, 2H), 7.25-7.20 (m, 2H), 7.09 (s, 1H), 7.05 (d, 2H, J=4.2 Hz), 6.99 (d, 1H, J=8.7 Hz), 6.81 (d, 1H, J=7.8 Hz), 6.77 (s, 1H), 5.30-5.28 (m, 1H), 3.76 (s, 3H), 3.51 (s, 2H), 3.20 (1H, A of ABX, J=6.3, 13.6 Hz), 3.06 (1H, B of ABX, J=8.1, 13.8 Hz).

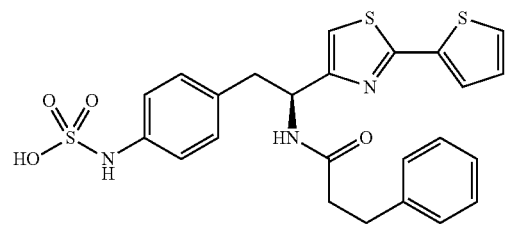

4-{(S)-2-(3-Phenylpropanamido)-2-[2-(thiophene2-yl)thiazol-4-yl]ethyl}phenyl-sulfamic acid: ¹H NMR (CD₃OD) δ 8.30 (d, 1H, J=9 Hz), 7.61-7.56 (m, 2H), 7.26-7.14 (m, 7H), 7.12 (d, 1H, J=1.5 Hz), 7.09 (d, 1H, J=2.1 Hz), 6.89 (s, 1H), 5.28-5.26 (m, 1H), 3.18 (1H, A of ABX, J=6.2, 13.8 Hz), 2.96 (1H, B of ABX, J=8.4, 13.6 Hz).

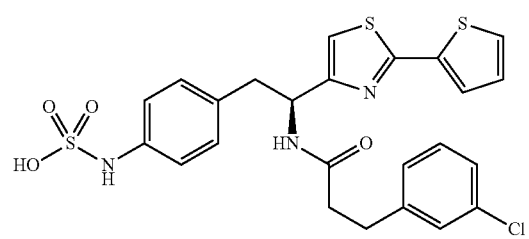

4-{(S)-2-(3-(3-Chlorophenyl)propanamido)-2-[2-(thiophene2-yl)thiazol-4-yl]ethyl}phenylsulfamic acid: ¹H NMR (CD₃OD) δ 7.61-7.56 (m, 3H), 7.22-7.14 (m, 6H), 7.08 (d, 1H), 7.00 (d, 1H, J=77.5 Hz), 6.870 (s, 1H), 5.25 (t, 1H, J=7.8 Hz), 3.18 (1H, A of ABX, J=6.6, 13.8 Hz), 2.97 (1H, B of ABX, J=7.8, 13.8 Hz), 2.87 (t, 2H, J=7.5 Hz), 2.51 (t, 2H, J=7.2 Hz).

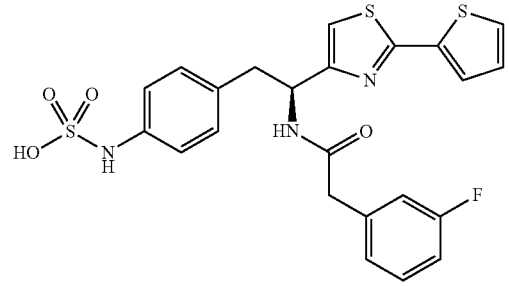

4-{(S)-2-[2-(3-Fluorophenyl)acetamido]-2-[2-(thiophene-2-yl)thiazol-4-yl]ethyl}phenylsulfamic acid: ¹H NMR (CD3OD) δ 7.61-7.57 (m, 2H), 7.32-7.28 (m, 1H), 7.19-7.16 (m, 2H), 7.08 (t, 1H, J=4.5 Hz), 7.02-6.95 (m, 6H), 5.29 (t, 1H, J=8.1 Hz), 3.53 (s, 2H), 3.22 (1H, A of ABX, J=6.6, 13.9 Hz), 3.06 (1H, B of ABX, J=8.4, 13.6 Hz).

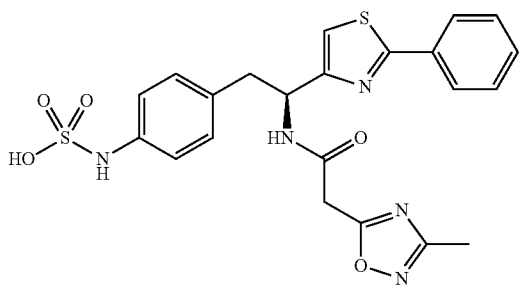

(S)-4-{2-[2-(3-Methyl-1,2,4-oxadiazol-5-yl)acetamido]-2-(2-phenylthiazol-4-yl)ethyl}phenylsulfamic acid: $^1$H(CD$_3$OD): δ 7.98-7.95 (m, 2H), 7.48-7.46 (m, 3H), 7.23 (s, 1H), 7.09-7.05 (m, 4H), 5.33 (t, 1H, J=7.2 Hz), 3.33-3.06 (m, 2H), 2.35 (s, 3H).

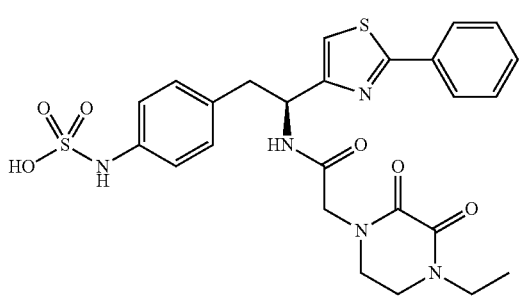

4-{(S)-2-[2-(4-ethyl-2,3-dioxopiperazin-1-yl)acetamido]-2-[2-(thiophene-2-yl)thiazol-4-yl]ethyl}phenylsulfamic acid: $^1$H NMR (CD3OD) δ 7.62 (d, 1H, J=3 Hz), 7.58 (d, 1H, J=15.6 Hz), 7.27 (s, 1H), 7.16 (t, 1H, J=1.5 Hz), 5.42-5.32 (m, 1H), 4.31 (d, 1H, J=15.6 Hz), 3.91 (d, 1H, J=15.9 Hz), 3.60-3.50 (m, 4H), 3.30-3.23 (m, 2H), 2.98 (1H, B of ABX, J=9.9, 13.8 Hz), 1.21 (t, 3H, J=6.9 Hz).

The third aspect of Category I of the present disclosure relates to compounds having the formula:

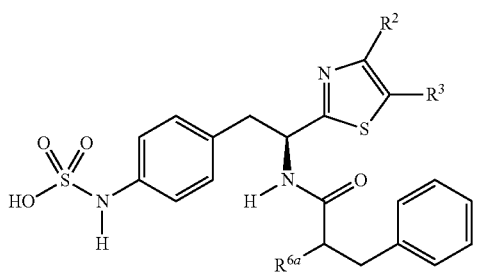

wherein the linking unit L comprises a phenyl unit, said linking group having the formula:

—C(O)[(CR$^{6a}$H)][(CH$_2$)]—

$R^{5a}$ is phenyl or substituted phenyl and non-limiting examples of the units $R^2$, $R^3$, and $R^{6a}$ are further exemplified herein below in Table III.

TABLE III

| No. | $R^2$ | $R^3$ | $R^{6a}$ |
|---|---|---|---|
| 201 | methyl | hydrogen | phenyl |
| 202 | methyl | hydrogen | 2-fluorophenyl |
| 203 | methyl | hydrogen | 3-fluorophenyl |
| 204 | methyl | hydrogen | 4-fluorophenyl |
| 205 | methyl | hydrogen | 3,4-difluorophenyl |
| 206 | methyl | hydrogen | 2-chlorophenyl |
| 207 | methyl | hydrogen | 3-chlorophenyl |
| 208 | methyl | hydrogen | 4-chlorophenyl |
| 209 | methyl | hydrogen | 3,4-dichlorophenyl |
| 210 | methyl | hydrogen | 2-methoxyphenyl |
| 211 | methyl | hydrogen | 3-methoxyphenyl |
| 212 | methyl | hydrogen | 4-methoxyphenyl |
| 213 | ethyl | hydrogen | phenyl |
| 214 | ethyl | hydrogen | 2-fluorophenyl |
| 215 | ethyl | hydrogen | 3-fluorophenyl |
| 216 | ethyl | hydrogen | 4-fluorophenyl |
| 217 | ethyl | hydrogen | 3,4-difluorophenyl |
| 218 | ethyl | hydrogen | 2-chlorophenyl |
| 219 | ethyl | hydrogen | 3-chlorophenyl |
| 220 | ethyl | hydrogen | 4-chlorophenyl |
| 221 | ethyl | hydrogen | 3,4-dichlorophenyl |
| 222 | ethyl | hydrogen | 2-methoxyphenyl |
| 223 | ethyl | hydrogen | 3-methoxyphenyl |
| 224 | ethyl | hydrogen | 4-methoxyphenyl |

The compounds encompassed within the third aspect of Category I of the present disclosure can be prepared by the procedure outlined in Scheme III and described in Example 3 herein below.

Scheme III

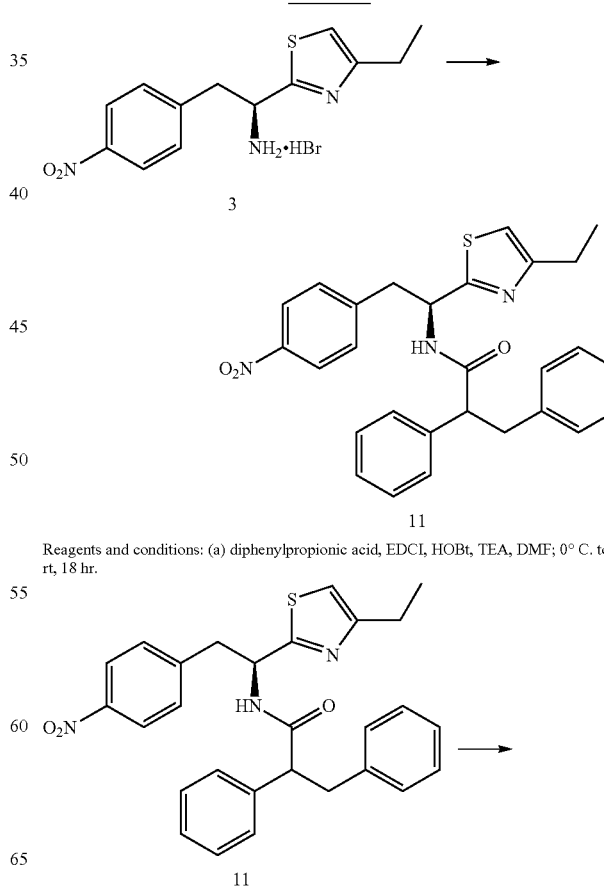

Reagents and conditions: (a) diphenylpropionic acid, EDCI, HOBt, TEA, DMF; 0° C. to rt, 18 hr.

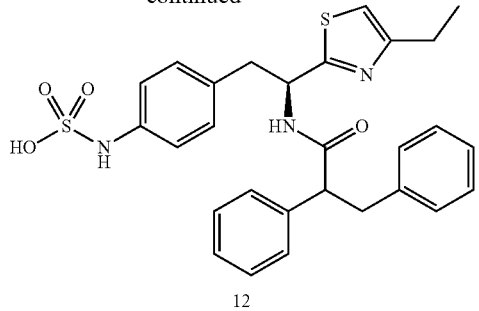

12

Reagents and conditions: (b) (i) H$_2$:Pd/C, MeOH; (ii) SO$_3$-pyridine, NH$_4$OH; rt, 18 hr.

Example 3

(S)-4-(2-(2,3-Diphenylpropanamido)-2-(4-ethylthiazol-2-yl)ethyl)-phenylsulfamic acid (12)

Preparation of (S)—N-[1-(4-ethylthiazol-2-yl)-2-(4-nitrophenyl)ethyl]-2,3-diphenyl-propanamide (11): To a solution of 1-(S)-(4-ethylthiazol-2-yl)-2-(4-nitrophenyl)ethyl amine hydrobromide, 3, (0.95 g, 2.65 mmol), diphenylpropionic acid (0.60 g, 2.65 mmol) and 1-hydroxybenzotriazole (HOBt) (0.180 g, 1.33 mmol) in DMF (10 mL) at 0°, is added 1-(3-dimethylaminopropyl)-3-ethylcarbodiimide (EDCI) (0.502 g, 2.62 mmol) followed by triethylamine (1.1 mL, 7.95 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.903 g (70% yield) of the desired product which is used without further purification.

Preparation of (S)-4-(2-(2,3-diphenylpropanamido)-2-(4-ethylthiazol-2-yl)ethyl)phenylsulfamic acid (12) (S)—N-[1-(4-ethylthiazol-2-yl)-2-(4-nitrophenyl)ethyl]-2,3-diphenyl-propanamide, 11, (0.903 g) is dissolved in MeOH (10 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (30 mL) and treated with SO$_3$-pyridine (0.621 g). The reaction is stirred at room temperature for 5 minutes after which a 7% solution of NH$_4$OH is added. The mixture is then concentrated and the resulting residue is purified by reverse phase chromatography to afford 0.415 g of the desired product as the ammonium salt. $^1$H NMR (CD3OD) δ 8.59-8.52 (m, 1H), 7.37-7.04 (m, 9H), 6.97-6.93 (m, 1H), 6.89-6.85 (m, 2H), 5.36-5.32 (m, 1H), 3.91-3.83 (m, 1H), 3.29 (1H, A of ABX, obscured by solvent), 3.15 (1H, B of ABX, J=5.4, 33.8 Hz), 2.99-2.88 (m, 2H), 2.81-2.69 (m, 2H), 1.32-1.25 (m, 3H).

The precursors of many of the Z units which comprise the third aspect of Category I are not readily available. The following procedure illustrates an example of the procedure which can be used to provide different $R^{6a}$ units according to the present disclosure. Using the procedure outlined in Scheme IV and described in Example 4 the artisan can make modifications without undue experimentation to achieve the $R^{5a}$ units encompassed by the present disclosure.

Scheme IV

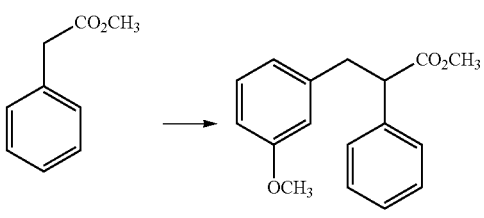

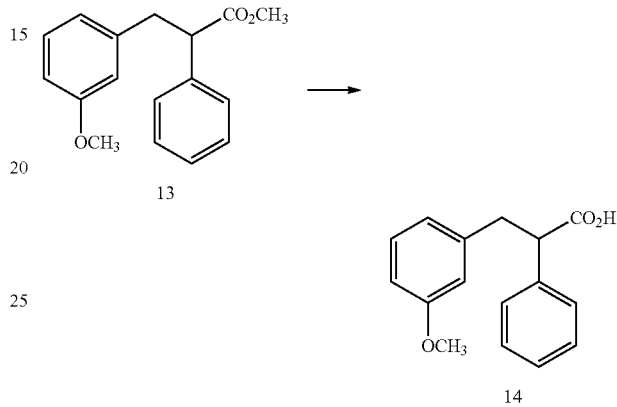

Reagents and conditions: (a) methyl 2-(2-methoxyphenyl)acetate, LDA, THF; 0° C. to rt 18 hr.

Reagents and conditions: (b)

Example 4

2-(2-Methoxyphenyl)-3-phenylpropanoic acid (14)

Preparation of methyl 2-(2-methoxyphenyl)-3-phenylpropanoate (13): A 500 mL round-bottom flask is charged with methyl 2-(2-methoxyphenyl)acetate (8.496 g, 47 mmol, 1 eq) and THF (200 mL). The homogeneous mixture is cooled to 0° C. in an ice bath. Lithium diisopropyl amide (23.5 mL of a 2.0M solution in heptane/THF) is added, maintaining a temperature less than 3° C. The reaction is stirred 45 minutes at this reduced temperature. Benzyl bromide (5.6 mL, 47 mmol, 1 eq) is added dropwise. The reaction is allowed to gradually warm to room temperature and is stirred for 18 hours. The reaction is quenched with 1N HCl and extracted 3 times with equal portions of EtOAc. The combined extracts are washed with H$_2$O and brine, dried over Na$_2$SO$_4$, filtered, and concentrated. The residue is purified over silica to afford 4.433 g (35%) of the desired compound. ESI+MS 293 (M+Na).

Preparation of 2-(2-methoxyphenyl)-3-phenylpropanoic acid (14): Methyl 2-(2-methoxyphenyl)-3-phenylpropanoate (4.433 g, 16 mmol, 1 eq) is dissolved in 100 mL of a 1:1 (v:v) mixture of THF and methanol. Sodium hydroxide (3.28 g, 82 mmol, 5 eq) is added and the reaction mixture is stirred 18 hours at room temperature. The reaction is then poured into H$_2$O and the pH is adjusted to 2 via addition of 1N HCl. A white precipitate forms which is removed by filtration. The resulting solution is extracted with 3 portion of diethyl ether. The extracts are pooled, washed with H$_2$O and brine, dried over Na$_2$SO$_4$, filtered, and concentrated in vacuo. The resulting residue is purified over silica to afford 2.107 g (51%) of the desired compound. ESI- MS 255 (M-1), 211 (M—CO$_2$H).

Intermediate 14 can be carried forward according to the procedure outlined in Scheme III and described in Example 3 to produce the following compound according to the third aspect of Category I.

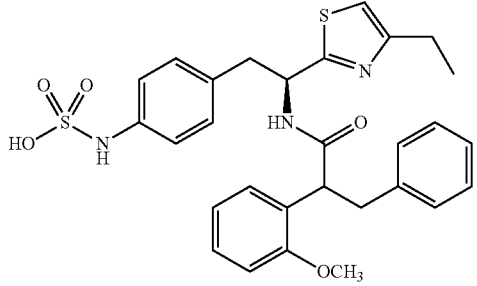

(S)-4-{2-(4-Ethylthiazol-2-yl)-2-[2-(2-methoxyphenyl)-3-phenylpropanamido]-ethyl}phenylsulfamic acid: $^1$H NMR (CD3OD) δ 7.32-7.12 (m, 7H), 7.05-7.02 (m, 1H), 6.99-6.83 (m, 4H), 6.80-6.75 (m, 2H), 5.35-5.31 (m, 1H), 4.31-4.26 (m, 1H), 3.75 (s, 3H), 3.20-2.90 (m, 4H), 2.79-2.74 (m, 2H), 1.32-1.25 (m, 3H).

The following are further non-limiting examples of compounds according to the third aspect of Category I of the present disclosure.

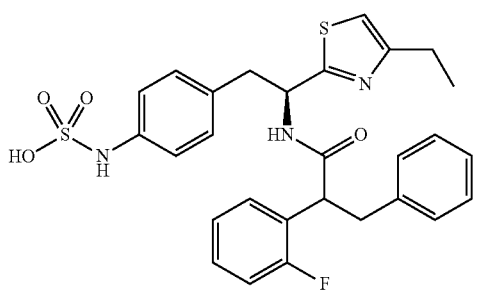

(S)-4-{2-(4-Ethylthiazol-2-yl)-2-[2-(3-fluorophenyl)-3-phenylpropanamido]-ethyl}phenylsulfamic acid: $^1$H NMR (CD3OD) δ 7.33-6.87 (m, 14H), 5.39-5.25 (m, 1H), 3.95-3.83 (m, 1H), 3.31-3.10 (m, 1H), 3.05-2.88 (m, 2H), 2.80-2.70 (m, 2H), 1.32-1.23 (m, 3H). $^{19}$F NMR δ 47.59.

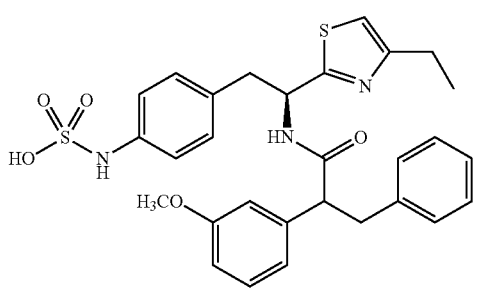

(S)-4-{2-(4-Ethylthiazol-2-yl)-2-[2-(3-methoxyphenyl)-3-phenylpropanamido]-ethyl}phenylsulfamic acid: $^1$H NMR (CD3OD) δ 7.85 (d, 1H, J=8.4 Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

The fourth aspect of Category I of the present disclosure relates to compounds having the formula:

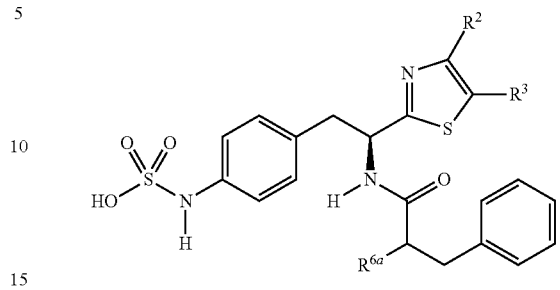

wherein the linking unit L comprises a phenyl unit, said linking group having the formula:

—C(O)[(CR$^{6a}$H)][(CH$_2$)]

R$^{5a}$ is substituted or unsubstituted heteroaryl and the units R$^2$, R$^3$, and R$^{5a}$ are further exemplified herein below in Table IV.

TABLE IV

| No. | R$^2$ | R$^3$ | R$^{6a}$ |
|---|---|---|---|
| 225 | methyl | hydrogen | 3-methyl-1,2,4-oxadiazol-5-yl |
| 226 | methyl | hydrogen | thiophene-2-yl |
| 227 | methyl | hydrogen | thiazol-2-yl |
| 228 | methyl | hydrogen | oxazol-2-yl |
| 229 | methyl | hydrogen | isoxazol-3-yl |
| 230 | ethyl | hydrogen | 3-methyl-1,2,4-oxadiazol-5-yl |
| 231 | ethyl | hydrogen | thiophene-2-yl |
| 232 | ethyl | hydrogen | thiazol-2-yl |
| 233 | ethyl | hydrogen | oxazol-2-yl |
| 234 | ethyl | hydrogen | isoxazol-3-yl |
| 235 | ethyl | methyl | 3-methyl-1,2,4-oxadiazol-5-yl |
| 236 | ethyl | methyl | thiophene-2-yl |
| 237 | ethyl | methyl | thiazol-2-yl |
| 238 | ethyl | methyl | oxazol-2-yl |
| 239 | ethyl | methyl | isoxazol-3-yl |
| 240 | thiophene-2-yl | hydrogen | 3-methyl-1,2,4-oxadiazol-5-yl |
| 241 | thiophene-2-yl | hydrogen | thiophene-2-yl |
| 242 | thiophene-2-yl | hydrogen | thiazol-2-yl |
| 243 | thiophene-2-yl | hydrogen | oxazol-2-yl |
| 244 | thiophene-2-yl | hydrogen | isoxazol-3-yl |
| 245 | isoxazol-3-yl | hydrogen | 3-methyl-1,2,4-oxadiazol-5-yl |
| 246 | isoxazol-3-yl | hydrogen | thiophene-2-yl |
| 247 | isoxazol-3-yl | hydrogen | thiazol-2-yl |
| 248 | isoxazol-3-yl | hydrogen | oxazol-2-yl |
| 249 | isoxazol-3-yl | hydrogen | isoxazol-3-yl |

The compounds encompassed within the fourth aspect of Category I of the present disclosure can be prepared by the procedure outlined in Scheme V and described in Example 5 herein below.

Scheme V

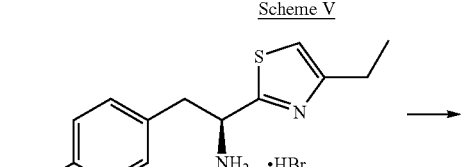

-continued

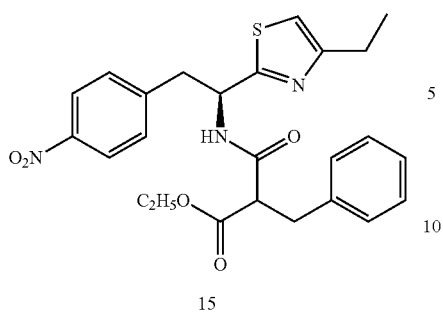

15

Reagents and conditions: (a) 2-benzyl-3-ethoxy-3-oxopropanoic acid, EDCI, HOBt, DIPEA, DMF; rt, 18 hr.

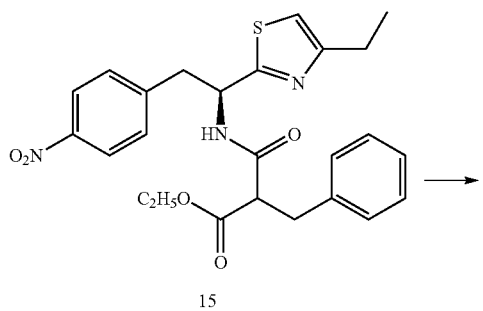

15

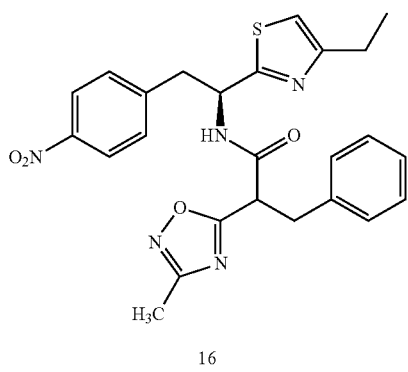

16

Reagents and conditions: (b) CH₃C(=NOH)NH₂, K₂CO₃, toluene; reflux, 18 hr

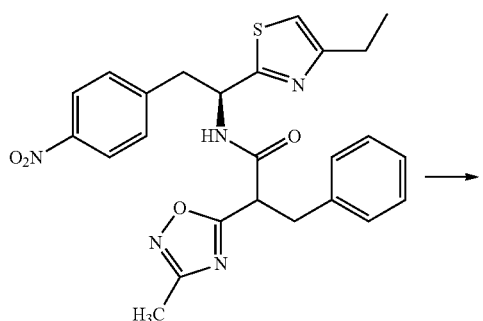

16

-continued

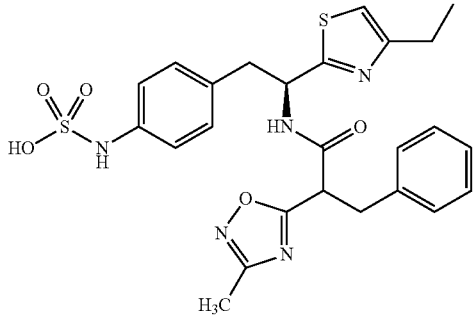

17

Reagents and conditions: (c) (i) H₂:Pd/C, MeOH; (ii) SO₃-pyridine, NH₄OH; rt, 18 hr.

Example 5

4-{(S)-2-(4-Ethylthiazol-2-yl)-2-[2-(3-methyl-1,2,4-oxadiazol-5-yl)-3-phenylpropanamido]ethyl}phenylsulfamic acid (17)

Preparation of ethyl-2-benzyl-3-[(S)-1-(4-ethylthiazol-2-yl)-2-(4-nitrophenyl)-ethylamino]-3-oxopropanoate (15): To a solution of 1-(S)-(4-ethylthiazol-2-yl)-2-(4-nitrophenyl) ethyl amine hydrobromide, 3, (0.406 g, 1.13 mmol), 2-benzyl-3-ethoxy-3-oxopropanoic acid (0.277 g) and 1-hydroxybenzotriazole (HOBt) (0.191 g, 1.41 mmol) in DMF (10 mL) at 0°, is added 1-(3-dimethylaminopropyl)-3-ethylcarbodiimide (EDCI) (0.240 g, 1.25 mmol) followed by diisopropylethylamine (DIPEA) (0.306 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.169 g (31% yield) of the desired product which is used without further purification.

Preparation of N-[(S)-1-(4-ethylthiazol-2-yl)-2-(4-nitrophenyl)ethyl]-2-(3-methyl-1,2,4-oxadiazol-5-yl)-3-phenylpropanamide (16): Ethyl 2-benzyl-3-((S)-1-(4-ethylthiazol-2-yl)-2-(4-nitrophenyl)ethylamino)-3-oxopropanoate is dissolved in toluene (5 mL) and heated to reflux. Potassium carbonate (80 mg) and acetamide oxime (43 mg) are added and treated with 80 mg potassium carbonate and 43 mg acetamide oxime at reflux. The reaction mixture is cooled to room temperature, filtered and concentrated. The residue is chromatographed over silica to afford 0.221 g (94%) of the desired product as a yellow oil.

Preparation of 4-{(S)-2-(4-ethylthiazol-2-yl)-2-[2-(3-methyl-1,2,4-oxadiazol-5-yl)-3-phenylpropanamido]ethyl}phenylsulfamic acid (17): N-[(S)-1-(4-ethylthiazol-2-yl)-2-(4-nitrophenyl)ethyl]-2-(3-methyl-1,2,4-oxadiazol-5-yl)-3-phenylpropanamide, 16, (0.221 g) and tin (II) chloride (507 mg, 2.2 mmol) are dissolved in EtOH (25 mL) and the solution is brought to reflux 4 hours. The solvent is removed in vacuo and the resulting residue is dissolved in EtOAc. A saturated solution of NaHCO₃ (50 mL) is added and the solution is stirred 1 hour. The organic layer is separated and the aqueous layer extracted twice with EtOAc. The combined organic layers are dried (Na₂SO₄), filtered and concentrated to a residue which is dissolved in pyridine (0.143 g) and treated with SO₃-pyridine (0.143 g). The reaction is stirred at room temperature for 5 minutes after which a 7% solution of NH$_4$OH is added. The mixture is then concentrated and the resulting residue is purified by reverse phase chromatography to afford 0.071 g of the desired product as the ammonium salt. $^1$H(CD$_3$OD): δ 7.29-6.87 (m, 10H), 5.38-5.30 (m, 1H), 4.37-4.30 (m, 1H), 3.42-2.74 (m, 6H), 2.38-2.33 (m, 3H), 1.34-1.28 (m, 3H).

Category II of the present disclosure relates to 2-(thiazol-2-yl) compounds having the formula:

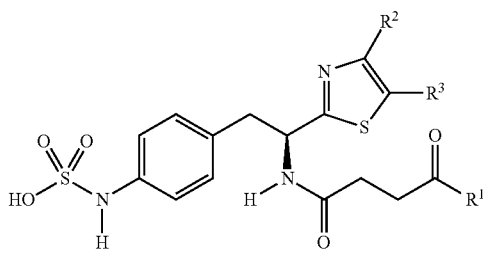

wherein R$^1$, R$^2$, R$^3$, and L are further defined herein in Table V herein below.

TABLE V

| No. | R$^2$ | R$^3$ | R$^1$ |
|---|---|---|---|
| 250 | ethyl | hydrogen | thiophene-2-yl |
| 251 | ethyl | hydrogen | thiazol-2-yl |
| 252 | ethyl | hydrogen | oxazol-2-yl |
| 253 | ethyl | hydrogen | isoxazol-3-yl |
| 254 | ethyl | hydrogen | thiophene-2-yl |
| 255 | ethyl | hydrogen | thiazol-2-yl |
| 256 | ethyl | hydrogen | oxazol-2-yl |
| 257 | ethyl | hydrogen | isoxazol-3-yl |
| 258 | ethyl | hydrogen | thiophene-2-yl |
| 259 | ethyl | hydrogen | thiazol-2-yl |
| 260 | ethyl | methyl | methyl |
| 261 | ethyl | methyl | ethyl |
| 262 | ethyl | methyl | propyl |
| 263 | ethyl | methyl | iso-propyl |
| 264 | ethyl | methyl | butyl |
| 265 | ethyl | methyl | phenyl |
| 266 | ethyl | methyl | benzyl |
| 267 | ethyl | methyl | 2-fluorophenyl |
| 268 | ethyl | methyl | 3-fluorophenyl |
| 269 | ethyl | methyl | 4-fluorophenyl |
| 270 | phenyl | hydrogen | methyl |
| 271 | phenyl | hydrogen | ethyl |
| 272 | phenyl | hydrogen | propyl |
| 273 | phenyl | hydrogen | iso-propyl |
| 274 | phenyl | hydrogen | butyl |
| 275 | phenyl | hydrogen | phenyl |
| 276 | phenyl | hydrogen | benzyl |
| 277 | phenyl | hydrogen | 2-fluorophenyl |
| 278 | phenyl | hydrogen | 3-fluorophenyl |
| 279 | phenyl | hydrogen | 4-fluorophenyl |
| 280 | thiophene-2-yl | hydrogen | methyl |
| 281 | thiophene-2-yl | hydrogen | ethyl |
| 282 | thiophene-2-yl | hydrogen | propyl |
| 283 | thiophene-2-yl | hydrogen | iso-propyl |
| 284 | thiophene-2-yl | hydrogen | butyl |
| 285 | thiophene-2-yl | hydrogen | phenyl |
| 286 | thiophene-2-yl | hydrogen | benzyl |
| 287 | thiophene-2-yl | hydrogen | 2-fluorophenyl |
| 288 | thiophene-2-yl | hydrogen | 3-fluorophenyl |
| 289 | thiophene-2-yl | hydrogen | 4-fluorophenyl |

The compounds encompassed within Category II of the present disclosure can be prepared by the procedure outlined in Scheme VI and described in Example 6 herein below.

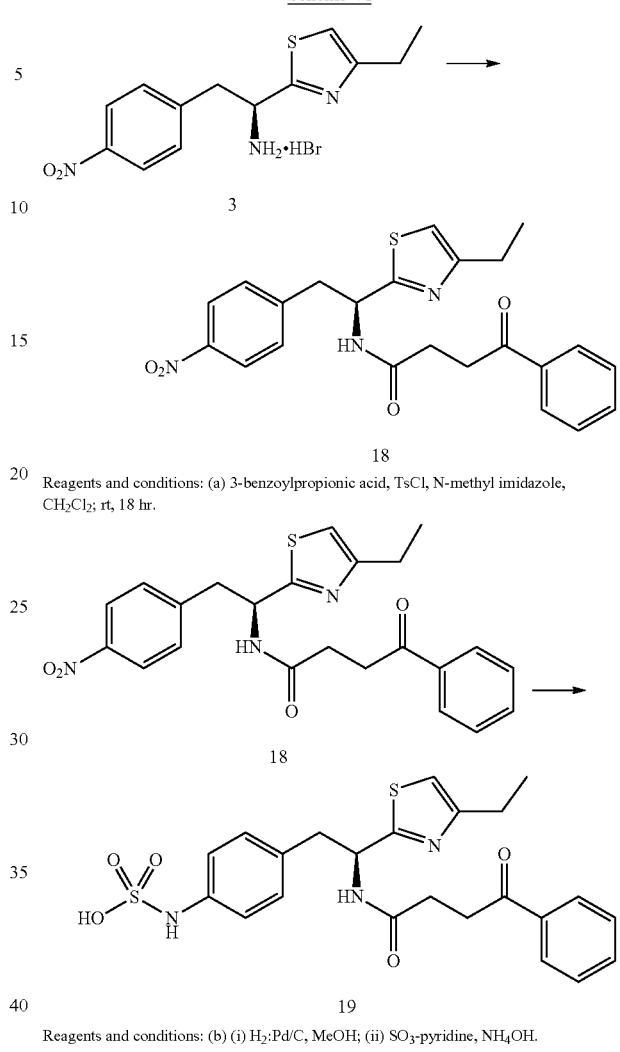

Scheme VI

Reagents and conditions: (a) 3-benzoylpropionic acid, TsCl, N-methyl imidazole, CH$_2$Cl$_2$; rt, 18 hr.

Reagents and conditions: (b) (i) H$_2$:Pd/C, MeOH; (ii) SO$_3$-pyridine, NH$_4$OH.

Example 6

(S)-4-[2-(4-Ethylthiazol-2-yl)-2-(4-oxo-4-phenylbutanamido)ethyl]-phenylsulfamic acid (19)

Preparation of (S)-N-[1-(4-ethylthiazol-2-yl)-2-(4-nitrophenyl)ethyl]-4-oxo-4-phenylbutanamide (18): 3-Benzoylpropionic acid (0.250 g) is dissolved in CH$_2$Cl$_2$ (5 mL), N-methyl imidazole (0.333 mL) is added and the resulting solution is cooled to 0° C. after which a solution of p-toluenesulfonyl chloride (0.320 g) in CH$_2$Cl$_2$ (2 mL) is added dropwise. After 0.5 hours (S)-1-(4-ethylthiazol-2-yl)-2-(4-nitrophenyl)ethanamine, 3, (0.388 g) is added. The reaction is stirred for 18 hours at room temperature and then concentrated in vacuo. The resulting residue is dissolved in EtOAc and washed with 1N HCl and brine. The solution is dried over Na$_2$SO$_4$, filtered, and concentrated and the crude material purified over silica to afford 0.415 g of the desired product.

Preparation of (S)-4-[2-(4-ethylthiazol-2-yl)-2-(4-oxo-4-phenylbutanamido)-ethyl]phenylsulfamic acid (19): (S)—N-[1-(4-ethylthiazol-2-yl)-2-(4-nitrophenyl)ethyl]-2,3-diphenyl-propanamide, 18, (0.2 g) is dissolved in MeOH (15 mL).

A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (5 mL) and treated with SO$_3$-pyridine (0.153 g). The reaction is stirred at room temperature for 5 minutes after which a 7% solution of NH$_4$OH is added. The mixture is then concentrated and the resulting residue is purified by reverse phase chromatography to afford 0.090 g of the desired product as the ammonium salt. $^1$H NMR (CD$_3$OD) δ 8.68 (d, 1H, J=8.2 Hz), 8.00 (d, 2H, J=7.2 Hz), 7.80-7.50 (m, 3H), 7.12 (s, 4H), 7.03 (s, 1H), 5.46-5.38 (m, 1H), 3.29-3.14 (m, 2H), 3.06-2.99 (m, 2H), 2.83 (q, 2H, J=7.5 Hz), 2.69-2.54 (m, 2H), 1.33 (t, 3H, J=7.5 Hz).

The following are non-limiting examples of compounds encompassed within Category II of the present disclosure. The intermediate nitro compounds of the following can be prepared by coupling the appropriate 4-oxo-carboxylic acid with intermediate 3 under the conditions described herein above for the formation of intermediate 4 of scheme I.

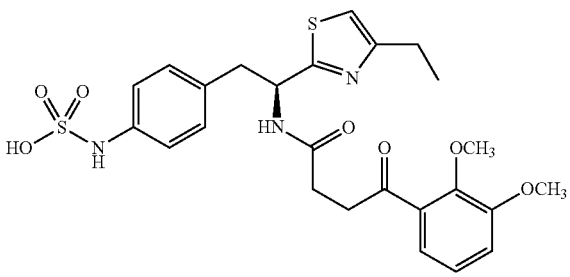

(S)-4-{2-[4-(2,3-Dimethoxyphenyl)-4-oxobutanamido]-2-(4-ethylthiazol-2-yl)ethyl}phenylsulfamic acid: $^1$H NMR (CD$_3$OD), δ 8.64 (d, 1H, J=8.1 Hz), 7.21-7.11 (m, 7H), 7.02 (s, 1H), 5.42 (q, 1H, J=5.9 Hz), 3.90 (d, 3H, J=3.3 Hz), 3.88 (d, 3H, J=2.9 Hz), 3.22-3.18 (m, 2H), 3.07-2.99 (m, 2H), 2.83 (q, 2H, J=7.3 Hz), 2.63-2.54 (m, 2H), 1.34 (t, 3H, J=7.69 Hz).

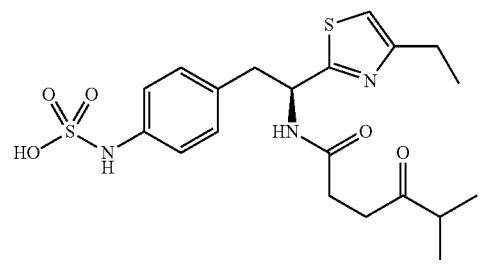

(S)-4-(2-(4-Ethylthiazol-2-yl)-2-(5-methyl-4-oxohexanamido)ethyl)phenyl-sulfamic acid: $^1$H NMR (CD$_3$OD) δ 8.59 (d, 1H, J=8.1 Hz), 7.14 (s, 4H), 7.08 (t, 1H, J=13.0 Hz), 5.40-5.35 (m, 1H), 3.37-3.27 (m, 2H), 3.04-2.97 (m, 1H), 2.83-2.61 (m, 4H), 2.54-2.36 (m, 3H), 1.33 (t, 2H, J=7.3 Hz), 1.09 (dd, 6H, J=7.0, 2.2 Hz).

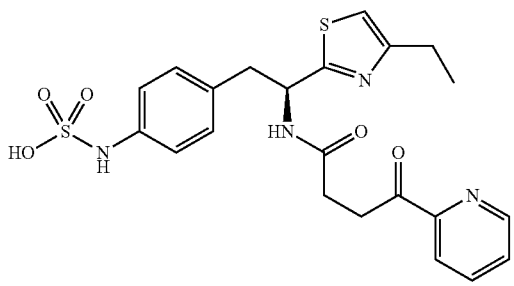

(S)-4-{2-(4-Ethylthiazol-2-yl)-2-[4-oxo-4-(pyridin-2-yl)butanamido]ethyl}-phenylsulfamic acid: $^1$H NMR (CD$_3$OD) δ 8.60 (d, 1H, J=12.8 Hz), 7.91-7.81 (m, 2H), 7.48-7.44 (m, 1H), 7.22-7.21 (m, 1H), 6.99 (s, 3H), 6.91 (s, 1H), 5.30 (q, 1H, J=5.4 Hz), 3.36 (q, 2H, J=7.0 Hz), 3.21-3.15 (m, 1H), 2.91-2.85 (m, 1H), 2.74 (q, 2H, J=10.4 Hz), 2.57-2.50 (m, 2H), 1.20 (t, 3H, J=7.5 Hz).

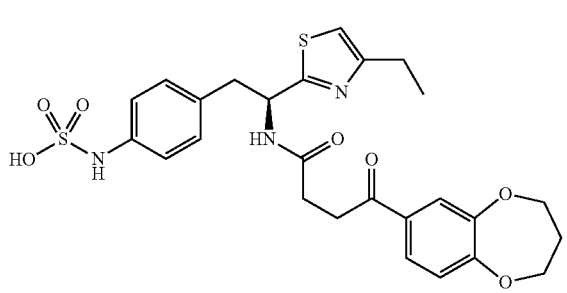

(S)-4-{2-[4-(3,4-Dihydro-2H-benzo[b][1,4]dioxepin-7-yl)-4-oxobutanamido]-2-(4-ethylthiazol-2-yl)ethyl}phenylsulfamic acid: $^1$H NMR (CD$_3$OD) δ 8.64 (d, 1H, J=8.4 Hz), 7.60 (d, 2H, J=10.6 Hz), 7.11 (s, 3H), 7.04 (d, 2H, J=5.5 Hz), 5.42-5.40 (m, 1H), 4.30-4.22 (m, 4H), 3.20-2.98 (m, 4H), 2.82 (q, 2H, J=7.3 Hz), 2.67-2.48 (m, 2H), 2.23 (t, 2H, J=5.5 Hz), 1.32 (t, 3H, J=7.3 Hz).

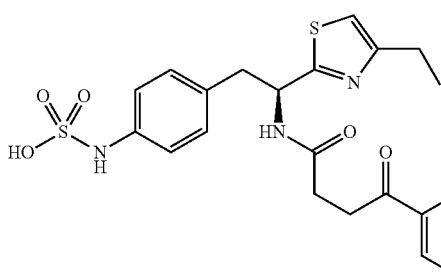

(S)-4-{2-[4-(2,3-dihydrobenzo[b][1,4]dioxin-6-yl)-4-oxobutanamido]-2-(4-ethylthiazol-2-yl)ethyl}phenylsulfamic acid: $^1$H NMR (CD$_3$OD) δ 7.52-7.47 (m, 2H), 7.11 (s, 4H), 7.03 (s, 1H), 6.95 (d, 1H, J=8.4 Hz), 5.41 (q, 1H, J=3.7 Hz), 4.31 (d, 4H, J=5.5 Hz), 3.24-3.12 (m, 2H), 3.06-2.98 (m, 2H), 2.83 (q, 2H, J=7.3 Hz), 2.62-2.53 (m, 2H), 1.33 (t, 3H, J=7.3 Hz).

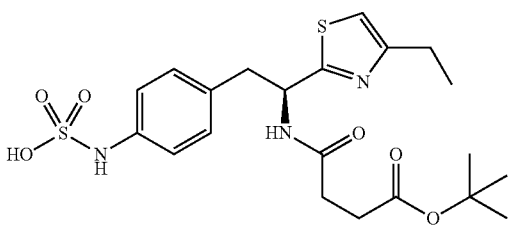

(S)-4-[2-(4-tert-butoxy-4-oxobutanamido)-2-(4-ethylthiazol-2-yl)ethyl]phenyl-sulfamic acid: $^1$H NMR (CD$_3$OD), δ 7.10 (s 4H), 7.02 (s, 1H), 5.41 (q, 1H, J=3.7 Hz), 3.30-3.25 (m, 1H), 3.06-2.99 (m, 1H), 2.83 (q, 2H, J=7.3 Hz), 2.52-2.40 (m, 4H), 1.42 (s, 9H), 1.33 (t, 3H, J=7.3 Hz).

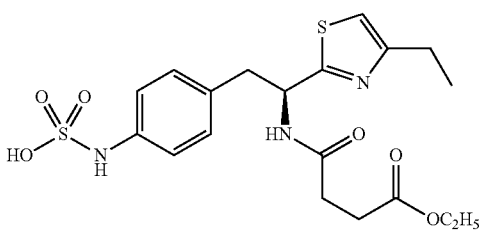

(S)-4-[2-(4-ethoxy-4-oxobutanamido)-2-(4-ethylthiazol-2-yl)ethyl]phenylsulfamic acid: $^1$H NMR (CD3OD) δ 8.62 (d, 1H, J=8.4 Hz), 7.10 (s, 4H), 7.02 (s, 1H), 5.40 (q, 1H, 3.7 Hz), 4.15 (q, 2H, J=7.3 Hz), 3.28-3.25 (m, 1H), 3.05-3.02 (m, 1H), 2.82 (q, 2H, J=4.4 Hz), 2.54-2.48 (m, 2H), 1.33 (t, 3H, J=7.3 Hz), 1.24 (t, 3H, J=7.0 Hz).

The first aspect of Category III of the present disclosure relates to 2-(thiazol-2-yl) compounds having the formula:

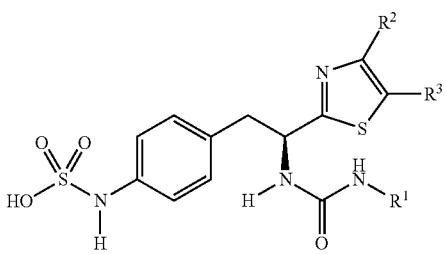

wherein non-limiting examples of R$^1$, R$^2$, and R$^3$ are further described herein below in Table VI.

TABLE VI

| No. | R$^2$ | R$^3$ | R$^1$ |
| --- | --- | --- | --- |
| 290 | methyl | hydrogen | phenyl |
| 291 | methyl | hydrogen | benzyl |
| 292 | methyl | hydrogen | 2-fluorophenyl |
| 293 | methyl | hydrogen | 3-fluorophenyl |
| 294 | methyl | hydrogen | 4-fluorophenyl |
| 295 | methyl | hydrogen | 2-chlorophenyl |
| 296 | methyl | hydrogen | 3-chlorophenyl |
| 297 | methyl | hydrogen | 4-chlorophenyl |
| 298 | ethyl | hydrogen | phenyl |
| 299 | ethyl | hydrogen | benzyl |
| 300 | ethyl | hydrogen | 2-fluorophenyl |
| 301 | ethyl | hydrogen | 3-fluorophenyl |
| 302 | ethyl | hydrogen | 4-fluorophenyl |
| 303 | ethyl | hydrogen | 2-chlorophenyl |

TABLE VI-continued

| No. | R$^2$ | R$^3$ | R$^1$ |
| --- | --- | --- | --- |
| 304 | ethyl | hydrogen | 3-chlorophenyl |
| 305 | ethyl | hydrogen | 4-chlorophenyl |
| 306 | thiene-2-yl | hydrogen | phenyl |
| 307 | thiene-2-yl | hydrogen | benzyl |
| 308 | thiene-2-yl | hydrogen | 2-fluorophenyl |
| 309 | thiene-2-yl | hydrogen | 3-fluorophenyl |
| 310 | thiene-2-yl | hydrogen | 4-fluorophenyl |
| 311 | thiene-2-yl | hydrogen | 2-chlorophenyl |
| 312 | thiene-2-yl | hydrogen | 3-chlorophenyl |
| 313 | thiene-2-yl | hydrogen | 4-chlorophenyl |

The compounds encompassed within Category III of the present disclosure can be prepared by the procedure outlined in Scheme VIII and described in Example 7 herein below.

Scheme VII

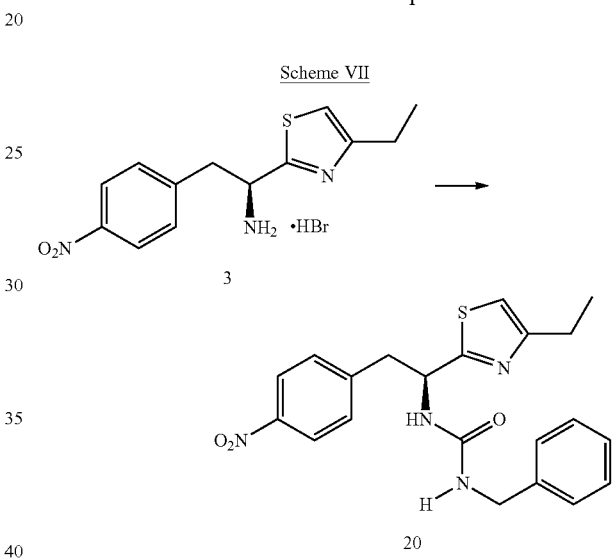

Reagents and conditions: (a) benzyl isocyanate, TEA, CH$_2$Cl$_2$; rt, 18 hr.

Reagents and conditions: (b) (i) H$_2$:Pd/C, MeOH; (ii) SO$_3$-pyridine, NH$_4$OH.

Example 7

(S)-4-(2-(3-Benzylureido)-2-(4-ethylthiazol-2-yl)ethyl)phenylsulfamic acid (21)

Preparation of (S)-1-benzyl-3-[1-(4-ethylthiazol-2-yl)-2-(4-nitrophenyl)ethyl]urea (20): To a solution of 1-(S)-(4-ethylthiazol-2-yl)-2-(4-nitrophenyl)ethyl amine hydrobromide, 3, (0.360 g, 1 mmol) and $Et_3N$ (0.42 mL, 3 mmol) in 10 mL $CH_2Cl_2$ is added benzyl isocyanate (0.12 mL, 1 mmol). The mixture is stirred at room temperature for 18 hours. The product is isolated by filtration to afford 0.425 g (96% yield) of the desired product which is used without further purification.

Preparation of (S)-4-(2-(3-benzylureido)-2-(4-ethylthiazol-2-yl)ethyl)phenyl-sulfamic acid (21): (S)-1-benzyl-3-[1-(4-ethylthiazol-2-yl)-2-(4-nitrophenyl)ethyl]urea, 20, (0.425 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with $SO_3$-pyridine (0.220 g). The reaction is stirred at room temperature for 5 minutes after which a 7% solution of $NH_4OH$ is added. The mixture is then concentrated and the resulting residue is purified by reverse phase chromatography to afford 0.143 g of the desired product as the ammonium salt. $^1H$ NMR ($CD_3OD$) δ 7.32-7.30 (m, 2H), 7.29-7.22 (m, 3H), 7.12-7.00 (m, 4H), 6.84 (d, 1H, J=8.1 Hz), 5.35-5.30 (m, 1H), 4.29 (s, 2H), 3.27-3.22 (m, 3H), 3.11-3.04 (m, 3H), 2.81 (q, 2H, J=10.2, 13.0 Hz), 1.31 (t, 3H, J=4.5 Hz).

The following is a non-limiting examples of compounds encompassed within the first aspect of Category III of the present disclosure.

4-{[(S)-2-(2-Ethylthiazol-4-yl)-2-(3-(R)-methoxy-1-oxo-3-phenylpropan-2-yl)ureido]ethyl}phenylsulfamic acid: $^1H$ NMR (CD3OD) δ 7.36-7.26 (m, 3H), 7.19-7.17 (m, 2H), 7.10-7.06 (m, 2H), 6.90-6.86 (m, 3H), 5.12-5.06 (m, 1H), 4.60-4.55 (m, 1H), 3.69 (s, 3H) 3.12-2.98 (m, 6H), 1.44-1.38 (m, 3H).

The second aspect of Category III of the present disclosure relates to 2-(thiazol-4-yl) compounds having the formula:

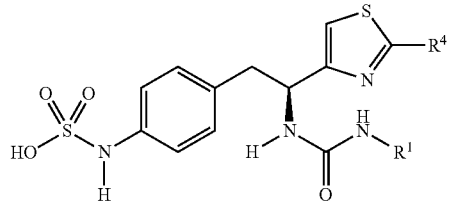

wherein non-limiting examples of $R^1$ and $R^4$ are further described herein below in Table VII.

TABLE VII

| No. | $R^1$ | $R^4$ |
|---|---|---|
| 314 | methyl | methyl |
| 315 | ethyl | methyl |
| 316 | n-propyl | methyl |
| 317 | iso-propyl | methyl |
| 318 | phenyl | methyl |
| 319 | benzyl | methyl |

TABLE VII-continued

| No. | $R^1$ | $R^4$ |
|---|---|---|
| 320 | 2-fluorophenyl | methyl |
| 321 | 2-chlorophenyl | methyl |
| 322 | thiophene-2-yl | methyl |
| 323 | thiazol-2-yl | methyl |
| 324 | oxazol-2-yl | methyl |
| 325 | isoxazol-3-yl | methyl |
| 326 | methyl | ethyl |
| 327 | ethyl | ethyl |
| 328 | n-propyl | ethyl |
| 329 | iso-propyl | ethyl |
| 330 | phenyl | ethyl |
| 331 | benzyl | ethyl |
| 332 | 2-fluorophenyl | ethyl |
| 333 | 2-chlorophenyl | ethyl |
| 334 | thiophene-2-yl | ethyl |
| 335 | thiazol-2-yl | ethyl |
| 336 | oxazol-2-yl | ethyl |
| 337 | isoxazol-3-yl | ethyl |
| 338 | methyl | thiophene-2-yl |
| 339 | ethyl | thiophene-2-yl |
| 340 | n-propyl | thiophene-2-yl |
| 341 | iso-propyl | thiophene-2-yl |
| 342 | phenyl | thiophene-2-yl |
| 343 | benzyl | thiophene-2-yl |
| 344 | 2-fluorophenyl | thiophene-2-yl |
| 345 | 2-chlorophenyl | thiophene-2-yl |
| 346 | thiophene-2-yl | thiophene-2-yl |
| 347 | thiazol-2-yl | thiophene-2-yl |
| 348 | oxazol-2-yl | thiophene-2-yl |
| 349 | isoxazol-3-yl | thiophene-2-yl |
| 350 | methyl | thiazol-2-yl |
| 351 | ethyl | thiazol-2-yl |
| 352 | n-propyl | thiazol-2-yl |
| 353 | iso-propyl | thiazol-2-yl |
| 354 | phenyl | thiazol-2-yl |
| 355 | benzyl | thiazol-2-yl |
| 356 | 2-fluorophenyl | thiazol-2-yl |
| 357 | 2-chlorophenyl | thiazol-2-yl |
| 358 | thiophene-2-yl | thiazol-2-yl |
| 359 | thiazol-2-yl | thiazol-2-yl |
| 360 | oxazol-2-yl | thiazol-2-yl |
| 361 | isoxazol-3-yl | thiazol-2-yl |
| 362 | methyl | oxazol-2-yl |
| 363 | ethyl | oxazol-2-yl |
| 364 | n-propyl | oxazol-2-yl |
| 365 | iso-propyl | oxazol-2-yl |
| 366 | phenyl | oxazol-2-yl |
| 367 | benzyl | oxazol-2-yl |
| 368 | 2-fluorophenyl | oxazol-2-yl |
| 369 | 2-chlorophenyl | oxazol-2-yl |
| 370 | thiophene-2-yl | oxazol-2-yl |
| 371 | thiazol-2-yl | oxazol-2-yl |
| 372 | oxazol-2-yl | oxazol-2-yl |
| 373 | isoxazol-3-yl | oxazol-2-yl |

The compounds encompassed within the second aspect of Category III of the present disclosure can be prepared by the procedure outlined in Scheme VIII and described in Example 8 herein below.

Scheme VIII

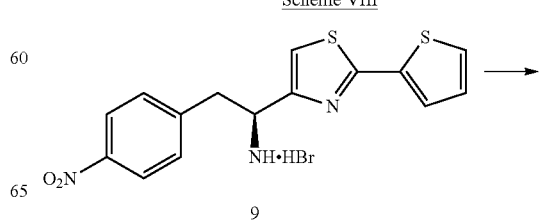

9

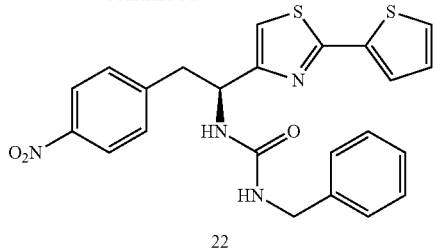

22

Reagents and conditions: (a) benzyl isocyanate, TEA, CH₂Cl₂; rt, 18 hr.

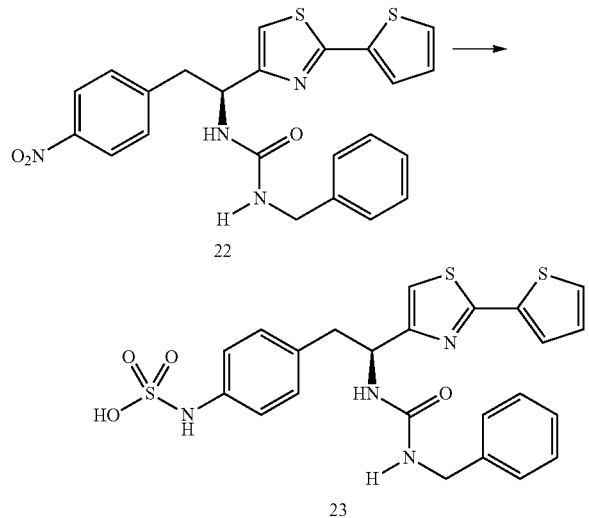

Reagents and conditions: (b) (i) H₂:Pd/C, MeOH; (ii) SO₃-pyridine, NH₄OH.

Example 8

4-{(S)-2-(3-Benzylureido)-2-[2-(thiophen-2-yl)thiazol-4-yl]ethyl}-phenylsulfamic acid (23)

Preparation of 1-benzyl-3-{(S)-2-(4-nitrophenyl)-1-[2-(thiophen-2-yl)thiazol-4-yl]ethyl}urea (22): To a solution of (S)-2-(4-nitrophenyl)-1-[(2-thiophene-2-yl)thiazol-4-yl)ethan-amine hydrobromide salt, 8, and Et₃N (0.42 mL, 3 mmol) in 10 mL DCM is added benzyl isocyanate (0.12 mL, 1 mmol). The mixture is stirred at room temperature for 18 hours. The product is isolated by filtration to afford 0.445 g (96% yield) of the desired product which is used without further purification.

Preparation of 4-{(S)-2-(3-benzylureido)-2-[2-(thiophen-2-yl)thiazol-4-yl]ethyl}phenyl-sulfamic acid (23): 1-Benzyl-3-{(S)-2-(4-nitrophenyl)-1-[2-(thiophen-2-yl)thiazol-4-yl]ethyl}urea, 22, (0.445 g) is dissolved in MeOH (10 mL) and CH₂Cl₂ (5 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.110 g). The reaction is stirred at room temperature for 5 minutes after which a 7% solution of NH₄OH is added. The mixture is then concentrated and the resulting residue is purified by reverse phase chromatography to afford 0.080 g of the desired product as the ammonium salt. $^1$H NMR (CD3OD) δ 7.61 (d, 1H, J=2.1 Hz), 7.58 (d, 1H, J=6 Hz), 7.33-7.22 (m, 4H), 7.17-7.14 (m, 1H), 7.09-6.94 (m, 6H), 5.16 (t, 1H, J=6.6 Hz), 4.13 (s, 2H), 3.14-3.11 (m, 2H).

Category IV of the present disclosure relates to 2-(thiazol-4-yl) compounds having the formula:

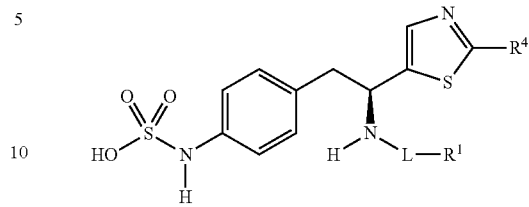

wherein $R^1$, $R^4$, and L are further defined herein in Table VIII herein below.

TABLE VIII

| No. | $R^4$ | L | $R^1$ |
|---|---|---|---|
| 374 | methyl | —SO₂— | methyl |
| 375 | ethyl | —SO₂— | methyl |
| 376 | phenyl | —SO₂— | methyl |
| 377 | thiophene-2-yl | —SO₂— | methyl |
| 378 | methyl | —SO₂— | trifluoromethyl |
| 379 | ethyl | —SO₂— | trifluoromethyl |
| 380 | phenyl | —SO₂— | trifluoromethyl |
| 381 | thiophene-2-yl | —SO₂— | trifluoromethyl |
| 382 | methyl | —SO₂— | ethyl |
| 383 | ethyl | —SO₂— | ethyl |
| 384 | phenyl | —SO₂— | ethyl |
| 385 | thiophene-2-yl | —SO₂— | ethyl |
| 386 | methyl | —SO₂— | 2,2,2-trifluoroethyl |
| 387 | ethyl | —SO₂— | 2,2,2-trifluoroethyl |
| 388 | phenyl | —SO₂— | 2,2,2-trifluoroethyl |
| 389 | thiophene-2-yl | —SO₂— | 2,2,2-trifluoroethyl |
| 390 | methyl | —SO₂— | phenyl |
| 391 | ethyl | —SO₂— | phenyl |
| 392 | phenyl | —SO₂— | phenyl |
| 393 | thiophene-2-yl | —SO₂— | phenyl |
| 394 | methyl | —SO₂— | 4-fluorophenyl |
| 395 | ethyl | —SO₂— | 4-fluorophenyl |
| 396 | phenyl | —SO₂— | 4-fluorophenyl |
| 397 | thiophene-2-yl | —SO₂— | 4-fluorophenyl |
| 398 | methyl | —SO₂— | 3,4-dihydro-2H-benzo[b][1,4]oxazin-7-yl |
| 399 | ethyl | —SO₂— | 3,4-dihydro-2H-benzo[b][1,4]oxazin-7-yl |
| 400 | phenyl | —SO₂— | 3,4-dihydro-2H-benzo[b][1,4]oxazin-7-yl |
| 401 | thiophene-2-yl | —SO₂— | 3,4-dihydro-2H-benzo[b][1,4]oxazin-7-yl |
| 402 | methyl | —SO₂— | 1-methyl-1H-imidazol-4-yl |
| 403 | ethyl | —SO₂— | 1-methyl-1H-imidazol-4-yl |
| 404 | phenyl | —SO₂— | 1-methyl-1H-imidazol-4-yl |
| 405 | thiophene-2-yl | —SO₂— | 1-methyl-1H-imidazol-4-yl |
| 406 | methyl | —SO₂— | 4-acetamidophenyl |
| 407 | ethyl | —SO₂— | 4-acetamidophenyl |
| 408 | phenyl | —SO₂— | 4-acetamidophenyl |
| 409 | thiophene-2-yl | —SO₂— | 4-acetamidophenyl |
| 410 | methyl | —SO₂CH₂— | phenyl |
| 411 | ethyl | —SO₂CH₂— | phenyl |
| 412 | phenyl | —SO₂CH₂— | phenyl |
| 413 | thiophene-2-yl | —SO₂CH₂— | phenyl |
| 414 | methyl | —SO₂CH₂— | (4-methylcarboxyphenyl)methyl |
| 415 | ethyl | —SO₂CH₂— | (4-methylcarboxyphenyl)methyl |
| 416 | phenyl | —SO₂CH₂— | (4-methylcarboxyphenyl)methyl |
| 417 | thiophene-2-yl | —SO₂CH₂— | (4-methylcarboxyphenyl)methyl |
| 418 | methyl | —SO₂CH₂— | (2-methylthiazol-4-yl)methyl |
| 419 | ethyl | —SO₂CH₂— | (2-methylthiazol-4-yl)methyl |
| 420 | phenyl | —SO₂CH₂— | (2-methylthiazol-4-yl)methyl |
| 421 | thiophene-2-yl | —SO₂CH₂— | (2-methylthiazol-4-yl)methyl |
| 422 | methyl | —SO₂CH₂CH₂— | phenyl |
| 423 | ethyl | —SO₂CH₂CH₂— | phenyl |

TABLE VIII-continued

| No. | R⁴ | L | R¹ |
|---|---|---|---|
| 424 | phenyl | —SO₂CH₂CH₂— | phenyl |
| 425 | thiophene-2-yl | —SO₂CH₂CH₂— | phenyl |

The compounds encompassed within Category IV of the present disclosure can be prepared by the procedure outlined in Scheme IX and described in Example 9 herein below.

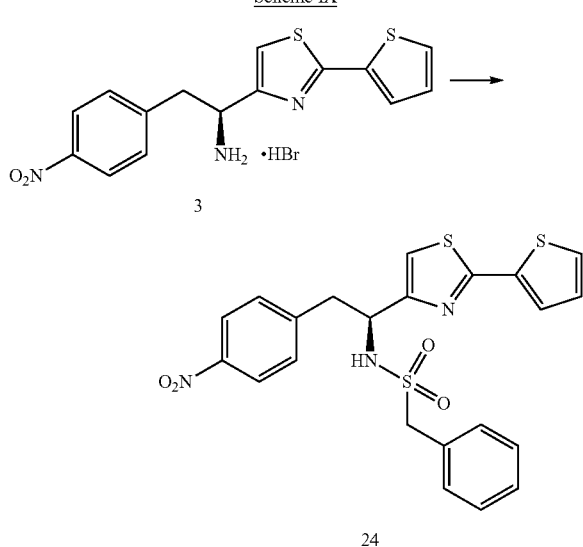

Reagents and conditions: (a) C₆H₄CH₂SO₂Cl, DIPEA, CH₂Cl₂; 0° C. to rt, 14 hr.

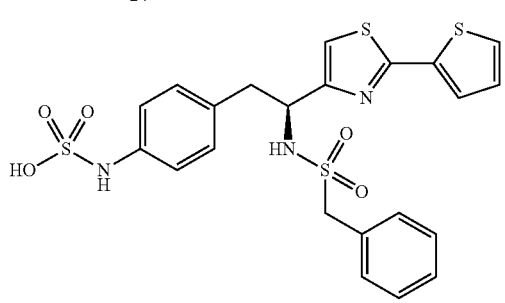

Reagents and conditions: (b) (i) H₂:Pd/C, MeOH; (ii) SO₃-pyridine, NH₄OH.

Example 9

{4-(S)-[2-Phenylmethanesulfonylamino-2-(2-thiophen-2-ylthiazol-4-yl)ethyl]phenyl}sulfamic acid (25)

Preparation of (S)—N-{2-(4-nitrophenyl)-1-[2-(thiophen-2-yl)thiazol-4-yl]ethyl}-1-phenylmethanesulfonamide (24): To a suspension of 2-(4-nitrophenyl)-1-(2-thiophene2-ylthiazol-4-yl)ethylamine, 8, (330 mg, 0.80 mmol) in CH₂Cl₂ (6 mL) at 0° C. is added diisopropylethylamine (0.30 mL, 1.6 mmol) followed by phenylmethanesulfonyl chloride (167 mg, 0.88 mmol). The reaction mixture is stirred at room temperature for 14 hours. The mixture is diluted with CH₂Cl₂ and washed with sat. NaHCO₃ followed by brine, dried (Na₂SO₄), filtered and concentrated in vacuo. The resulting residue is purified over silica to afford 210 mg of the desired product as a white solid.

Preparation of {4-(S)-[2-phenylmethanesulfonylamino-2-(2-thiophen-2-ylthiazol-4-yl)ethyl]phenyl}sulfamic acid (25): (S)—N-{2-(4-nitrophenyl)-1-[2-(thiophen-2-yl)thiazol-4-yl]ethyl}-1-phenylmethanesulfonamide, 24, (210 mg, 0.41 mmol) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (197 mg, 1.23 mmol). The reaction is stirred at room temperature for 5 minutes after which a 7% solution of NH₄OH is added. The mixture is then concentrated and the resulting residue is purified by reverse phase chromatography to afford 0.060 g of the desired product as the ammonium salt. ¹H NMR (300 MHz, MeOH-d₄) δ 7.52-7.63 (m, 6.70-7.28 (m, 11H), 4.75 (t, J=7.2 Hz, 1H), 3.95-4.09 (m, 2H), 3.20 (dd, J=13.5 and 7.8 Hz, 1H), 3.05 (dd, J=13.5 and 7.8 Hz, 1H). 1013770

Intermediates for use in Step (a) of Scheme IX can be conveniently prepared by the procedure outlined herein below in Scheme X and described in Example 10.

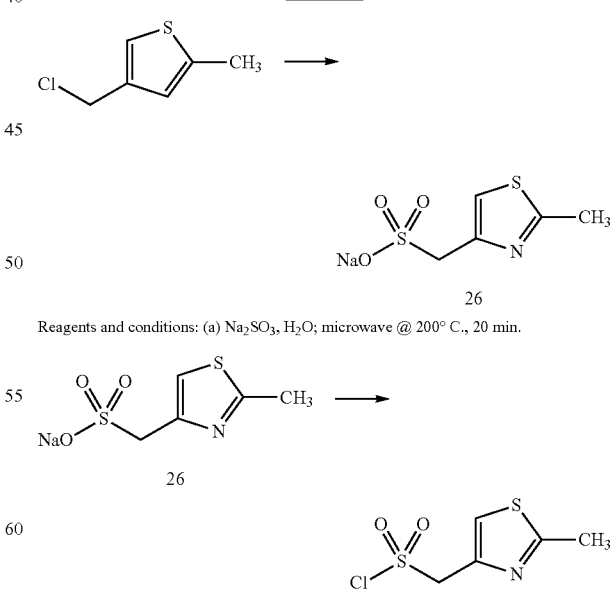

Reagents and conditions: (a) Na₂SO₃, H₂O; microwave @ 200° C., 20 min.

Reagents and conditions: (b) PCl₅, POCl₃; 50° C., 3 hrs.

Example 10

(2-Methylthiazol-4-yl)methanesulfonyl chloride (27)

Preparation of sodium (2-methylthiazol-4-yl)methane-sulfonate (26): 4-Chloromethyl-2-methylthiazole (250 mg, 1.69 mmol) is dissolved in H$_2$O (2 mL) and treated with sodium sulfite (224 mg, 1.78 mmol). The reaction mixture is subjected to microwave irradiation for 20 minutes at 200° C. The reaction mixture is diluted with H$_2$O (30 mL) and washed with EtOAc (2×25 mL). The aqueous layer is concentrated to afford 0.368 g of the desired product as a yellow solid. LC/MS ESI+194 (M+1, free acid).

Preparation of (2-methylthiazol-4-yl)methanesulfonyl chloride (27): Sodium (2-methylthiazol-4-yl)methane-sulfonate (357 mg, 1.66 mmol) is dissolved in phosphorous oxychloride (6 mL) and is treated with phosphorous pentachloride (345 mg, 1.66 mmol). The reaction mixture is stirred at 50° C. for 3 hours, then allowed to cool to room temperature. The solvent is removed under reduced pressure and the residue is re-dissolved in CH$_2$Cl$_2$ (40 mL) and is washed with sat. NaHCO$_3$ and brine. The organic layer is dried over MgSO$_4$, filtered, and the solvent removed in vacuo to afford 0.095 g of the desired product as a brown oil. LC/MS ESI+211 (M+1). Intermediates are obtained in sufficient purity to be carried forward according to Scheme IX without the need for further purification.

4-{(S)-2-[(2-methylthiazol-4-yl)methylsulfonamido]-2-[2-(thiophen-2-yl)thiazol-4-yl]ethyl}phenylsulfamic acid: $^1$H(CD$_3$OD): δ 7.71-7.66 (m, 2H), 7.27-7.10 (m, 7H), 4.87 (t, 1H, J=7.3 Hz), 4.30-4.16 (q, 2H, J=13.2 Hz), 3.34-3.13 (m, 2H), 2.70 (s, 3H).

The following are non-limiting examples of compounds encompassed within Category IV of the present disclosure.

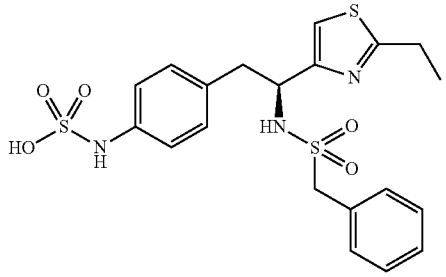

{4-(S)-[2-Phenylmethanesulfonylamino-2-(2-ethylthiazol-4-yl)ethyl]phenyl}-sulfamic acid: $^1$H NMR (300 MHz, MeOH-d$_4$) δ 7.27-7.32 (m, 3H), 7.16-7.20 (m, 3H), 7.05-7.6 (m, 2H), 6.96 (d, J=8.4 Hz, 2H), 4.70 (t, J=9.0 Hz, 1H), 3.91-4.02 (m, 2H), 2.95-3.18 (m, 4H), 1.41 (t, J=7.5 Hz, 3H).

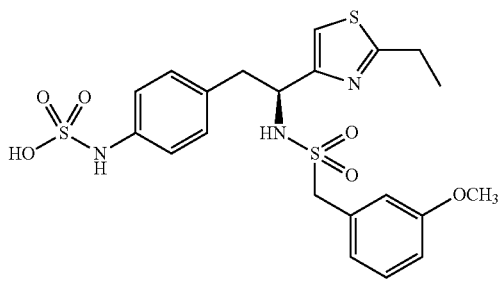

{4-(S)-[2-(3-Methoxyphenyl)methanesulfonylamino-2-(2-ethylthiazol-4-yl)ethyl]phenyl}sulfamic acid: $^1$H NMR (300 MHz, MeOH-d$_4$) δ 7.20 (t, J=8.1 Hz. 1H), 6.94-7.08 (m, 4H), 6.88-6.94 (m, 3H), 6.75-6.80 (m, 1H), 4.67 (t, J=7.2 Hz, 1H), 3.90-4.0 (m, 2H), 3.76 (s, 3H), 2.95-3.16 (m, 4H), 1.40 (t, J=7.5 HZ, 3H).

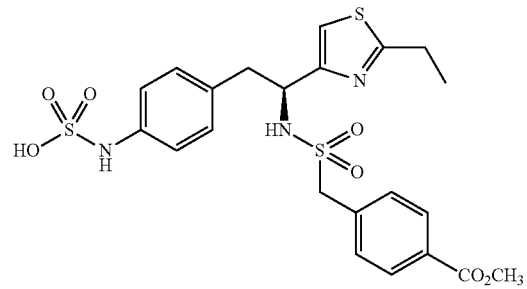

(S)-4-{[1-(2-Ethylthiazol-4-yl)-2-(4-sulfoaminophenyl)ethylsulfamoyl]methyl}-benzoic acid methyl ester: $^1$H NMR (300 MHz, MeOH-d$_4$) δ 7.90-7.94 (m, 2H), 7.27-7.30 (m, 2H), 7.06-7.11 (m, 3H), 6.97-7.00 (m, 2H), 4.71 (t, J=7.2 Hz, 1H), 3.95-4.08 (4, 2H), 3.92 (s, 3H), 2.80-3.50 (m, 4H), 1.38-1.44 (m, 3H).

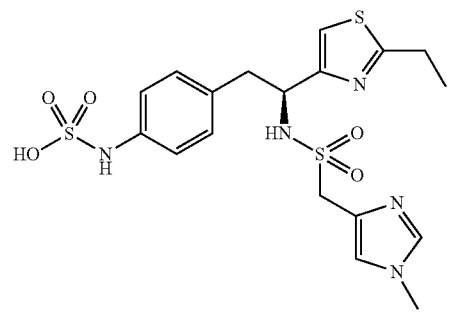

(S)-4-[2-(2-Ethylthiazol-4-yl)-2-(1-methyl-1H-imidazol-4-sulfonamido)ethyl]-phenylsulfamic acid: $^1$H NMR (300 MHz, MeOH-d$_4$) δ 7.54 (s, 1H, 7.20 (s, 1H), 7.09 (s, 1H), 6.92-7.00 (m, 4H), 4.62 (t, J=5.4 Hz, 1H), 3.70 (s, 3H), 2.98-3.14 (m, 3H), 2.79 (dd, J=9.3 and 15.0 Hz, 1H), 1.39 (q, J=7.5 Hz, 3H).

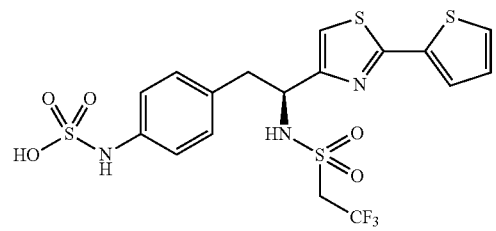

4-{(S)-2-[2-(Thiophen-2-yl)thiazol-4-yl]-2-(2,2,2-trifluoroethylsulfonamido)-ethyl}phenylsulfamic acid: $^1$H(CD$_3$OD): δ 7.62-7.56 (m, 2H), 7.22 (s, 1H), 7.16-7.06 (m, 5H), 4.84 (t, 1H, J=7.6 Hz), 3.71-3.62 (m, 2H), 3.32-3.03 (m, 2H).

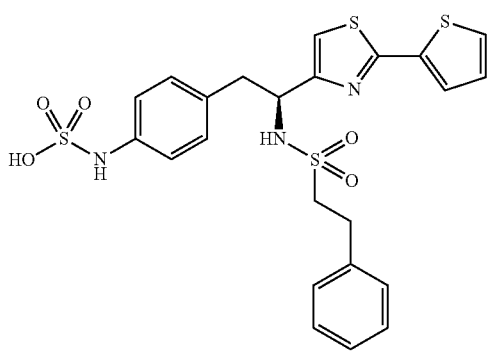

{4-(S)-[2-(Phenylethanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 7.04-7.19 (m, 9H), 6.94-6.97 (m, 2H), 4.78 (t, J=7.8 Hz, 1H), 3.22-3.30 (m, 2H)), 3.11 (dd, J=13.5 and 7.8 Hz, 1H), 2.78-2.87 (m, 4H).

{4-(S)-[3-(Phenylpropanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 6.99-7.17 (m, 10H), 4.72 (t, J=7.8 Hz, 1H), 3.21 (dd, J=13.5 and 7.2 Hz, 1H), 3.02 (dd, J=13.5 and 7.2 Hz, 1H), 2.39-2.64 (m, 4H), 1.65-1.86 (m, 2H).

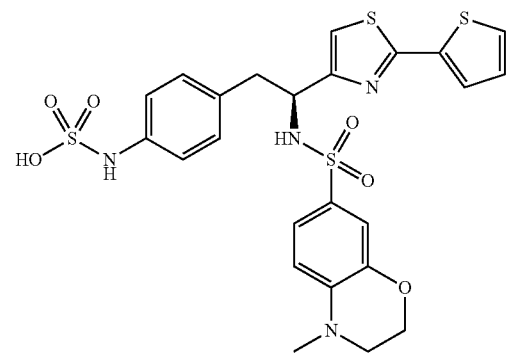

(S)-{4-[2-(4-Methyl-3,4-dihydro-2H-benzo[1,4]oxazine-7-sulfonylamino)-2-(2-thiophen-2-ylthiazol-4-yl)ethyl]phenyl}sulfamic acid: $^1$H NMR (300 MHz, MeOH-d$_4$) δ 7.53 (d, J=5.1 Hz, 1H) 7.48 (d, J=5.1 Hz, 1H), 7.13-7.10 (m, 1H), 7.04 (d, J=8.4 Hz, 2H), 6.93-6.88 (m, 3H), 6.75 (d, J=8.1 Hz, 1H), 6.54 (d, J=8.1 Hz, 1H), 4.61 (t, J=7.5 Hz, 1H), 4.20-4.08 (m, 2H), 3.14-3.00 (m, 4H), 2.69 (s, 3H).

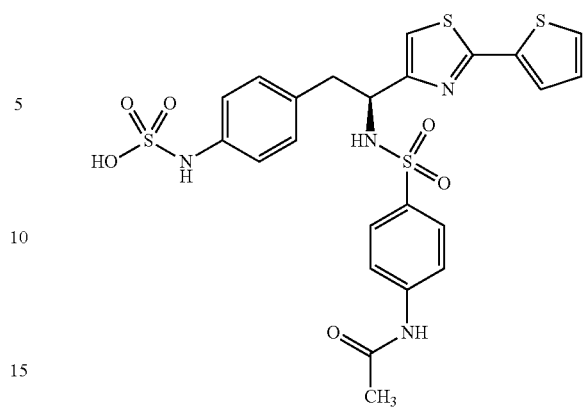

4-{(S)-2-(4-acetamidophenylsulfonamido)-2-[2-(thiophen-2-yl)thiazol-4-yl]ethyl}phenylsulfamic acid: $^1$H(CD$_3$OD): δ 7.67-7.52 (m, 6H), 7.24-7.23 (m, 1H), 7.12-7.09 (m, 3H), 7.02-6.99 (m, 2H), 4.70 (t, 1H, J=7.3 Hz), 3.25-3.00 (m, 2H), 2.24 (s, 3H).

The first aspect of Category V of the present disclosure relates to compounds having the formula:

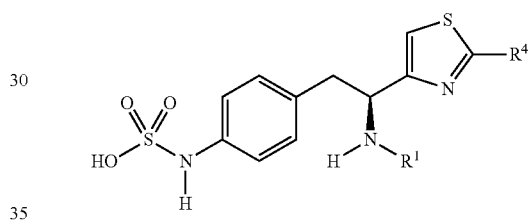

wherein R$^1$ is a substituted or unsubstituted heteroaryl and R$^4$ is C$_1$-C$_6$ linear, branched, or cyclic alkyl as further described herein below in Table IX.

TABLE IX

| No. | R$^4$ | R$^1$ |
|---|---|---|
| 426 | —CH$_3$ | 4-(methoxycarbonyl)thiazol-5-yl |
| 427 | —CH$_3$ | 4-[(2-methoxy-2-oxoethyl)carbamoyl]thiazol-5-yl |
| 428 | —CH$_3$ | 5-[1-N-(2-methoxy-2-oxoethyl)-1-H-indol-3-yl]oxazol-2-yl |
| 429 | —CH$_3$ | 5-(2-methoxyphenyl)oxazol-2-yl |
| 430 | —CH$_3$ | 5-[(S)-1-(tert-butoxycarbonyl)-2-phenylethyl]oxazol-2-yl |
| 431 | —CH$_3$ | 5-[4-(methylcarboxy)phenyl]oxazol-2-yl |
| 432 | —CH$_3$ | 5-(3-methoxybenzyl)oxazol-2-yl |
| 433 | —CH$_3$ | 5-(4-phenyl)oxazol-2-yl |
| 434 | —CH$_3$ | 5-(2-methoxyphenyl)thiazol-2-yl |
| 435 | —CH$_3$ | 5-(3-methoxyphenyl)thiazol-2-yl |
| 436 | —CH$_3$ | 5-(4-fluorophenyl)thiazol-2-yl |
| 437 | —CH$_3$ | 5-(2,4-difluorophenyl)thiazol-2-yl |
| 438 | —CH$_3$ | 5-(3-methoxybenzyl)thiazol-2-yl |
| 439 | —CH$_3$ | 4-(3-methoxyphenyl)thiazol-2-yl |
| 440 | —CH$_3$ | 4-(4-fluorophenyl)thiazol-2-yl |
| 441 | —CH$_2$CH$_3$ | 4-(methoxycarbonyl)thiazol-5-yl |
| 442 | —CH$_2$CH$_3$ | 4-[(2-methoxy-2-oxoethyl)carbamoyl]thiazol-5-yl |
| 443 | —CH$_2$CH$_3$ | 5-[1-N-(2-methoxy-2-oxoethyl)-1-H-indol-3-yl]oxazol-2-yl |
| 444 | —CH$_2$CH$_3$ | 5-(2-methoxyphenyl)oxazol-2-yl |
| 445 | —CH$_2$CH$_3$ | 5-[(S)-1-(tert-butoxycarbonyl)-2-phenylethyl]oxazol-2-yl |
| 446 | —CH$_2$CH$_3$ | 5-[4-(methylcarboxy)phenyl]oxazol-2-yl |
| 447 | —CH$_2$CH$_3$ | 5-(3-methoxybenzyl)oxazol-2-yl |
| 448 | —CH$_2$CH$_3$ | 5-(4-phenyl)oxazol-2-yl |
| 449 | —CH$_2$CH$_3$ | 5-(2-methoxyphenyl)thiazol-2-yl |

TABLE IX-continued

| No. | R⁴ | R¹ |
|---|---|---|
| 450 | —CH₂CH₃ | 5-(3-methoxyphenyl)thiazol-2-yl |
| 451 | —CH₂CH₃ | 5-(4-fluorophenyl)thiazol-2-yl |
| 452 | —CH₂CH₃ | 5-(2,4-difluorophenyl)thiazol-2-yl |
| 453 | —CH₂CH₃ | 5-(3-methoxybenzyl)thiazol-2-yl |
| 454 | —CH₂CH₃ | 4-(3-methoxyphenyl)thiazol-2-yl |
| 455 | —CH₂CH₃ | 4-(4-fluorophenyl)thiazol-2-yl |
| 456 | cyclopropyl | 4-(methoxycarbonyl)thiazol-5-yl |
| 457 | cyclopropyl | 4-[(2-methoxy-2-oxoethyl)carbamoyl]thiazol-5-yl |
| 458 | cyclopropyl | 5-[1-N-(2-methoxy-2-oxoethyl)-1-H-indol-3-yl]oxazol-2-yl |
| 459 | cyclopropyl | 5-(2-methoxyphenyl)oxazol-2-yl |
| 460 | cyclopropyl | 5-[(S)-1-(tert-butoxycarbonyl)-2-phenylethyl]oxazol-2-yl |
| 461 | cyclopropyl | 5-[4-(methylcarboxy)phenyl]oxazol-2-yl |
| 462 | cyclopropyl | 5-(3-methoxybenzyl)oxazol-2-yl |
| 463 | cyclopropyl | 5-(4-phenyl)oxazol-2-yl |
| 464 | cyclopropyl | 5-(2-methoxyphenyl)thiazol-2-yl |
| 465 | cyclopropyl | 5-(3-methoxyphenyl)thiazol-2-yl |
| 466 | cyclopropyl | 5-(4-fluorophenyl)thiazol-2-yl |
| 467 | cyclopropyl | 5-(2,4-difluorophenyl)thiazol-2-yl |
| 468 | cyclopropyl | 5-(3-methoxybenzyl)thiazol-2-yl |
| 469 | cyclopropyl | 4-(3-methoxyphenyl)thiazol-2-yl |
| 470 | cyclopropyl | 4-(4-fluorophenyl)thiazol-2-yl |

Compounds according to the first aspect of Category V which comprise a substituted or unsubstituted thiazol-4-yl unit for R¹ can be prepared by the procedure outlined in Scheme XI and described herein below in Example 11.

Scheme XI

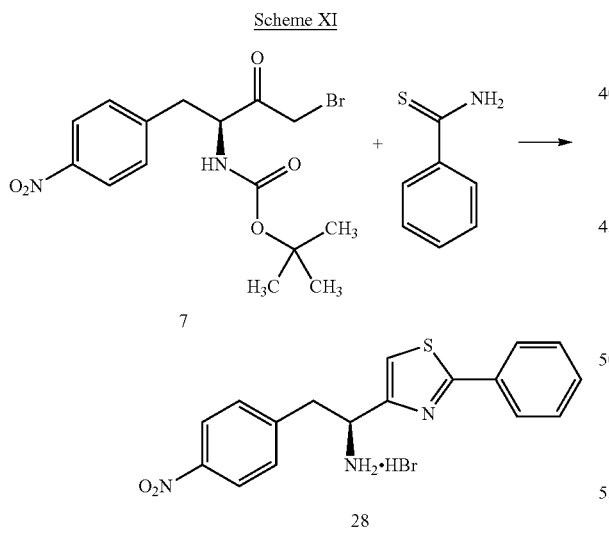

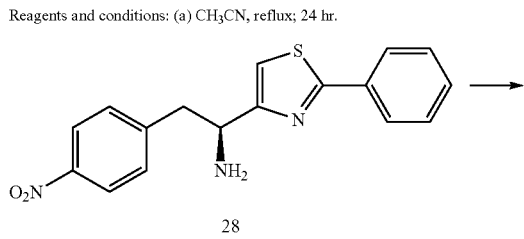

Reagents and conditions: (a) CH₃CN, reflux; 24 hr.

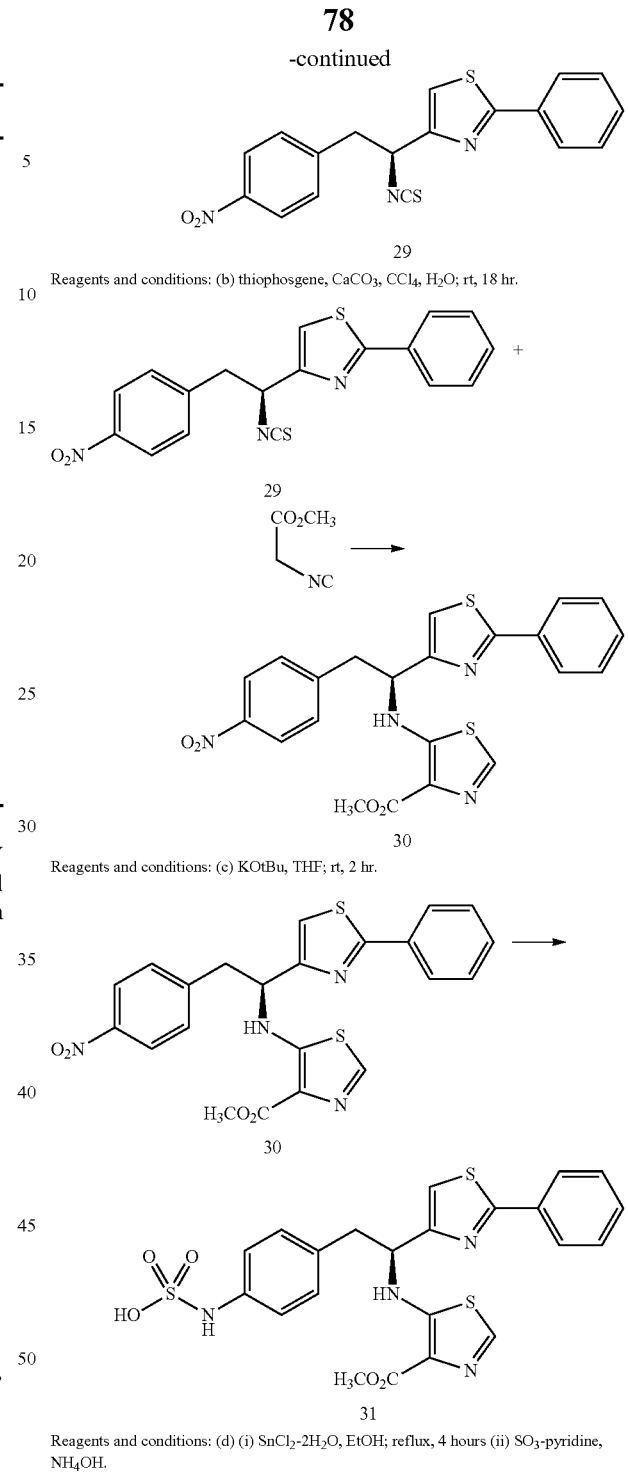

Reagents and conditions: (b) thiophosgene, CaCO₃, CCl₄, H₂O; rt, 18 hr.

Reagents and conditions: (c) KOtBu, THF; rt, 2 hr.

Reagents and conditions: (d) (i) SnCl₂·2H₂O, EtOH; reflux, 4 hours (ii) SO₃-pyridine, NH₄OH.

Example 11

(S)-4-(2-(2-Phenylthiazol-4-yl)-2-(4-(methoxycarbonyl)thiazole-5-ylamino)ethyl)phenylsulfamic acid (31)

Preparation of (S)-2-(4-nitrophenyl)-1-(2-phenylthiazol-4-yl)ethanamine hydrobromide salt (28): A mixture of (S)-tert-butyl 4-bromo-1-(4-nitrophenyl)-3-oxobutan-2-ylcarbamate, 7, (1.62 g, 4.17 mmol) and thiobenzamide (0.63 g, 4.60 mmol) in CH₃CN (5 mL) is refluxed for 24 hours. The reaction mixture is cooled to room temperature and diethyl ether (50 mL) is added to the solution. The precipitate which forms is collected by filtration. The solid is dried under vacuum to afford 1.2 g (67% yield) of the desired product. LC/MS ESI+326 (M+1).

Preparation of (S)-4-(1-isothiocyanato-2-(4-nitrophenyl) ethyl)-2-phenylthiazole (29): To a solution of (S)-2-(4-nitrophenyl)-1-(2-phenylthiazol-4-yl)ethanamine hydrobromide salt, 29, (726 mg, 1.79 mmol) and CaCO$_3$ (716 mg, 7.16 mmol) in H$_2$O (2 mL) is added CCl$_4$ (3 mL) followed by thiophosgene (0.28 mL, 3.58 mmol). The reaction is stirred at room temperature for 18 hours then diluted with CH$_2$Cl$_2$ and water. The layers are separated and the aqueous layer extracted with CH$_2$Cl$_2$. The combined organic layers are washed with brine, dried (Na$_2$SO$_4$) and concentrated in vacuo to a residue which is purified over silica (CH$_2$Cl$_2$) to afford 480 mg (73%) of the desired product as a yellow solid. $^1$H NMR (300 MHz, CDCl$_3$) δ 8.15 (d, J=8.7 Hz, 2H), 7.97-7.99 (m, 2H), 7.43-7.50 (m, 3H), 7.34 (d, J=8.7 Hz, 2H), 7.15 (d, J=0.9 Hz, 1H), 5.40-5.95 (m, 1H), 3.60 (dd, J=13.8 and 6.0 Hz, 1H), 3.46 (dd, J=13.8 and 6.0 Hz).

Preparation of (S)-methyl 5-[1-(2-phenylthiazol-4-yl)-2-(4-nitrophenyl)-ethylamino]thiazole-4-carboxylate (30): To a suspension of potassium tert-butoxide (89 mg, 0.75 mmol) in THF (3 mL) is added methyl isocyanoacetate (65 µL, 0.68 mmol) followed by (S)-2-phenyl-4-(1-isothiocyanato-2-(4-nitrophenyl)ethyl)thiazole, 29, (250 mg, 0.68 mmol). The reaction mixture is stirred at room temperature for 2 hours then poured into sat. NaHCO$_3$. The mixture is extracted with EtOAc (3×25 mL) and the combined organic layers are washed with brine and dried (Na$_2$SO$_4$) and concentrated in vacuo. The crude residue is purified over silica to afford 323 mg (~100% yield) of the desired product as a slightly yellow solid. $^1$H NMR (300 MHz, CDCl$_3$) δ 8.09-8.13 (m, 2H), 7.95-7.98 (m, 3H), 7.84 (d, J=1.2 Hz, 1H), 7.44-7.50 (m, 3H), 7.28-7.31 (m, 2H), 7.96 (d, J=0.6 Hz, 1H), 4.71-4.78 (m, 1H), 3.92 (s, 3H), 3.60 (dd, J=13.8 and 6.0 Hz, 1H), 3.45 (dd, J=13.8 and 6.0 Hz, 1H).

Preparation of (S)-4-(2-(2-phenylthiazol-4-yl)-2-(4-(methoxycarbonyl)thiazole-5-ylamino)ethyl)phenylsulfamic acid (31): (S)-methyl 5-[1-(2-phenylthiazol-4-yl)-2-(4-nitrophenyl)-ethylamino]thiazole-4-carboxylate, 30, (323 mg, 0.68 mmol) and tin (II) chloride (612 mg, 2.72 mmol) are dissolved in EtOH and the solution is brought to reflux. The solvent is removed in vacuo and the resulting residue is dissolved in EtOAc. A saturated solution of NaHCO$_3$ is added and the solution is stirred 1 hour. The organic layer is separated and the aqueous layer extracted twice with EtOAc. The combined organic layers are dried (Na$_2$SO$_4$), filtered and concentrated to a residue which is dissolved in pyridine (10 mL) and treated with SO$_3$-pyridine (130 mg, 0.82 mmol). The reaction is stirred at room temperature for 5 minutes after which a 7% solution of NH$_4$OH is added. The mixture is then concentrated and the resulting residue is purified by reverse phase chromatography to afford 0.071 g of the desired product as the ammonium salt $^1$H NMR (300 MHz, MeOH-d$_4$) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

Compounds according to the first aspect of Category V which comprise a substituted or unsubstituted thiazol-2-yl unit for R$^1$ can be prepared by the procedure outlined in Scheme XII and described herein below in Example 12. Intermediate 32 can be prepared according to Scheme II and Example 2 by substituting cyclopropane-carbothioic acid amide for thiophene-2-carbothioic acid amide.

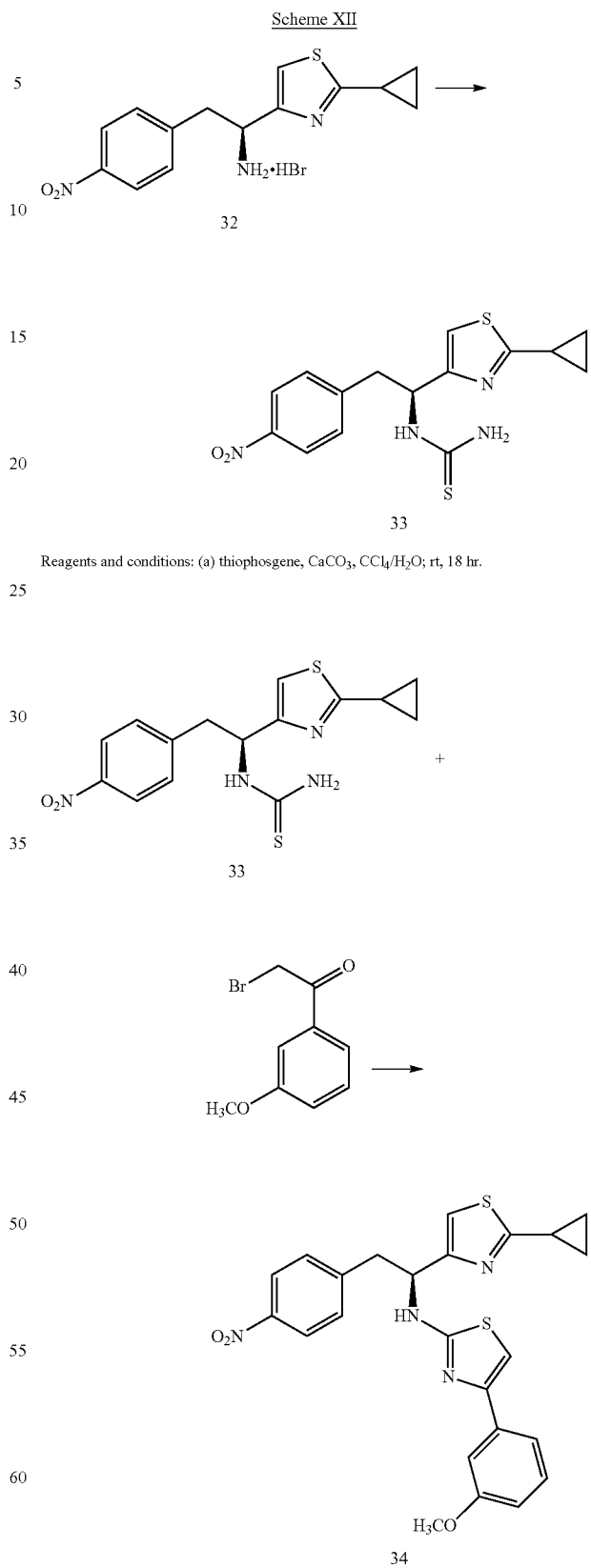

Scheme XII

Reagents and conditions: (a) thiophosgene, CaCO$_3$, CCl$_4$/H$_2$O; rt, 18 hr.

Reagents and conditions: (b)

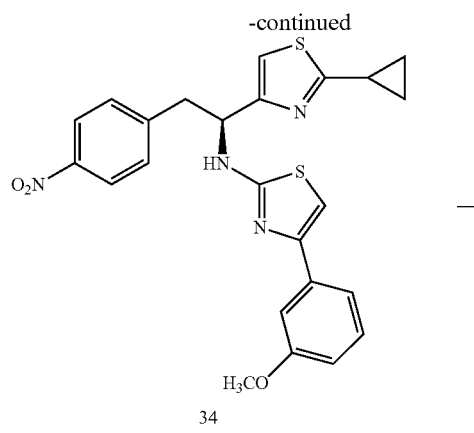

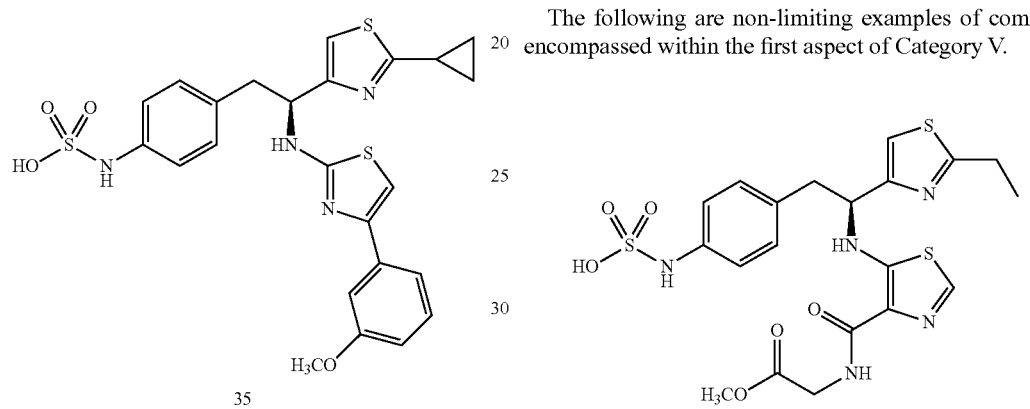

Reagents and conditions: (c) (i) H₂:Pd/C, MeOH; (ii) SO₃-pyridine, NH₄OH.

Example 12

4-{(S)-2-(2-Cyclopropylthiazol-4-yl)-2-[4-(3-methoxyphenyl)thiazol-2-ylamino]ethyl}phenylsulfamic acid (35)

Preparation of (S)-1-(1-(2-cyclopropylthiazol-4-yl)-2-(4-nitrophenyl)ethyl)-thiourea (33): To a solution of (S)-1-(2-cyclopropylthiazol-4-yl)-2-(4-nitrophenyl)ethan-amine hydrobromide hydrobromide salt, 32, (4.04 g, 10.9 mmol) and CaCO₃ (2.18 g, 21.8 mmol) in CCl₄/water (25 mL/20 mL) is added thiophosgene (1.5 g, 13.1 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is subsequently treated with ammonia (0.5M in 1,4-dioxane, 120 mL) which is purified over silica to afford 2.90 g of the desired product as a red-brown solid. LC/MS ESI-347 (M−1).

Preparation of (S)-4-(3-methoxybenzyl)-N-(1-(2-cyclopropylthiazol-4-yl)-2-(4-nitrophenyl)ethyl)thiazol-2-amine (34): (S)-1-(1-(2-Cyclopropylthiazol-4-yl)-2-(4-nitrophenyl)ethyl)-thiourea, 32, (350 mg, 1.00 mmol) and 2-bromo-3′-methoxy-acetophenone (253 mg, 1.10 mmol) are combined in 3 mL CH₃CN and heated to reflux for 24 hours. The mixture is concentrated and chromatographed to afford 0.172 g of the product as a yellow solid. LC/MS ESI+479 (M+1).

Preparation of 4-{(S)-2-(2-cyclopropylthiazol-4-yl)-2-[4-(3-methoxyphenyl)-thiazol-2-ylamino] ethyl}phenylsulfamic acid: (35): (S)-4-(3-methoxybenzyl)-N-(1-(2-cyclopropylthiazol-4-yl)-2-(4-nitrophenyl)ethyl) thiazol-2-amine, 34, (0.172 g) is dissolved in 10 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 5 mL pyridine and treated with SO₃-pyridine (114 mg). The reaction is stirred at room temperature for 5 minutes after which 10 mL of a 7% solution of NH₄OH is added. The mixture is then concentrated and the resulting residue is purified by reverse-phase chromatography to afford 0.033 g of the desired product as the ammonium salt. ¹H (CD₃OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

The following are non-limiting examples of compounds encompassed within the first aspect of Category V.

(S)-4-(2-(4-((2-Methoxy-2-oxoethyl)carbamoyl)thiazole-5-ylamino)-2-(2-ethylthiazole-4-yl)ethyl)phenylsulfamic acid: ¹H NMR (300 MHz, MeOH-d₄) δ 7.91 (s, 1H), 7.08-7.10 (m, 3H), 6.99 (d, J=8.7 Hz, 2H), 4.58 (t, J=6.9 Hz, 1H), 4.11 (d, J=2.7 Hz, 2H), 3.78 (s, 3H), 3.14-3.28 (m, 2H), 3.06 (q, J=7.5 Hz, 2H), 1.41 (t, J=7.5 Hz, 3H).

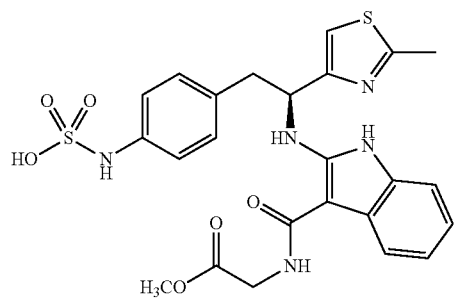

(S)-4-(2-{5-[1-N-(2-Methoxy-2-oxoethylcarbamoyl)-1-H-indol-3-yl]oxazol-2-ylamino}-2-(2-methylthiazol-4-yl)ethyl)phenylsulfamic acid: ¹H NMR (300 MHz, MeOH-d₄) δ 7.63 (d, J=7.8 Hz, 1H), 7.37 (s, 1H), 7.18-7.29 (m, 4H), 7.02-7.16 (m, 4H), 6.85 (s, 1H), 5.04-5.09 (m, 1H), 4.85 (s, 3H), 3.27 (dd, J=13.5 and 8.1 Hz, 1H), 3.10 (m, J=13.5 and 8.1 Hz, 1H), 2.69 (s, 3H).

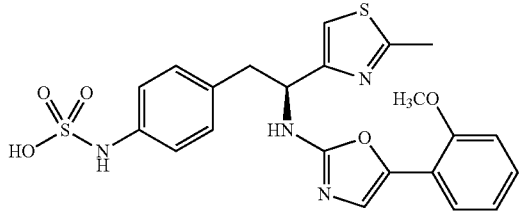

4-((S)-2-(5-(2-Methoxyphenyl)oxazol-2-ylamino)-2-(2-methylthiazol-4-yl)ethyl)phenylsulfamic acid: ¹H NMR (300 MHz, MeOH-d₄) δ 7.52 (dd, J=7.5 and 1.2 Hz, 1H), 6.95-7.24 (m, 10H), 5.04-5.09 (m, 1H), 3.92 (s, 3H), 3.26 (dd, J=13.8 and 8.4 Hz, 1H), 3.10 (dd, J=13.8 and 8.4 Hz, 1H), 2.72 (s, 3H).

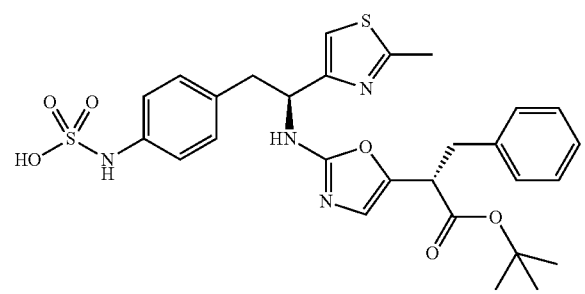

4-((S)-2-(5-((S)-1-(tert-Butoxycarbonyl)-2-phenylethyl)oxazole-2-ylamino)-2-(2-methylthiazole-4-yl)ethyl)phenyl-sulfamic acid: ¹H NMR (300 MHz, MeOH-d₄) δ 7.03-7.27 (m, 10H), 6.50 (s, 1H), 4.95-5.00 (m, 1H), 4.76 (t, J=6.9 Hz, 1H), 3.22 (dd, J=14.1 and 6.9 Hz, 1H), 3.00-3.10 (m, 2H), 2.90 (dd, J=14.1 and 6.9 Hz, 1H), 2.72 (s, 3H), 1.37 (s, 9H).

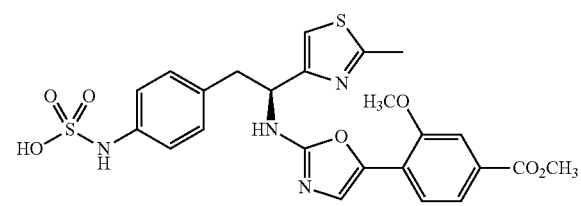

(S)-{4-{2-[5-(4-Methoxycarbonyl)phenyl]oxazol-2-ylamino}-2-(2-methylthiazol-4-yl)ethyl}phenylsulfamic acid: ¹H NMR (300 MHz, MeOH-d₄) δ 7.99 (d, J=7.5 Hz, 2H), 7.56-7.59 (m, 2H), 7.23-7.24 (m, 1H), 7.08-7.14 (m, 4H), 6.83 (d, J=10.2 Hz, 1H), 5.08 (t, J=6.0 Hz, 1H), 3.91 (s, 3H), 3.25-3.35 (m, 1H), 3.09-3.13 (m, 1H), 2.73 (s, 3H).

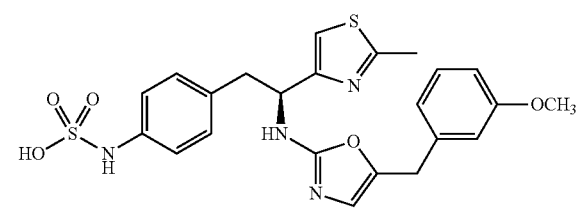

(S)-4-(2-(5-(3-Methoxybenzyl)oxazole-2-ylamino)-2-(2-methylthiazole-4-yl)ethyl)phenylsulfamic acid: ¹H NMR (300 MHz, MeOH-d₄) δ 7.03-7.28 (m, 8H), 6.79-6.83 (m, 1H), 5.70 (s, 1H), 4.99-5.06 (m, 2H), 4.41 (d, J=2.1 Hz, 2H), 3.80 (s, 3H), 3.27-3.37 (m, 1H), 3.03-3.15 (m, 1H), 2.71 (s, 3H).

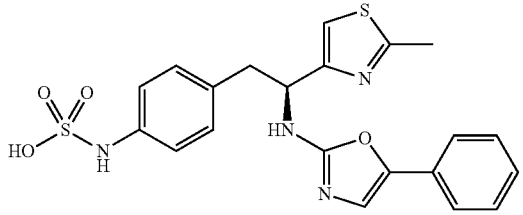

(S)-4-(2-(2-Methylthiazole-4-yl)-2-(5-phenyloxazole-2-ylamino)ethyl)phenyl-sulfamic acid: ¹H NMR (300 MHz, MeOH-d₄) δ 7.45 (d, J=8.7 Hz, 2H), 7.33 (t, J=7.8 Hz, 2H), 7.18-7.22 (m, 1H), 7.10-7.14 (m, 6H), 7.04 (s, 1H), 5.04-5.09 (m, 1H), 3.26 (dd, J=13.8 and 6.3 Hz, 1H), 3.10 (dd, J=13.8 and 6.3 Hz, 1H), 2.70 (s, 3H).

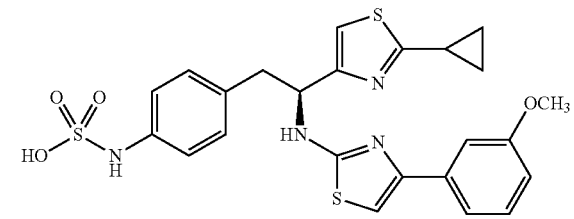

4-((S)-2-(2-Cyclopropylthiazol-4-yl)-2-(4-(3-methoxyphenyl)thiazol-2-ylamino)ethyl)phenylsulfamic acid: ¹H(CD₃OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

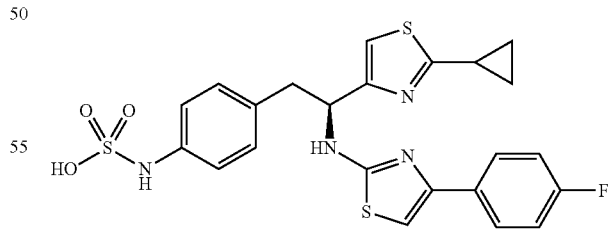

(S)-4-(2-(2-cyclopropylthiazol-4-yl)-2-(4-(4-fluorophenyl)thiazol-2-ylamino)ethyl)phenylsulfamic acid: ¹H(CD₃OD): δ 7.79-7.74 (m, 2H), 7.14-7.03 (m, 7H), 7.21 (s, 1H), 6.79 (s, 1H), 5.08 (t, 1H, J=6.6 Hz), 3.29-3.12 (m, 2H), 2.40 (q, 2.40, J=5.1 Hz), 1.23-1.18 (m, 2H), 1.08-1.02 (m, 2H).

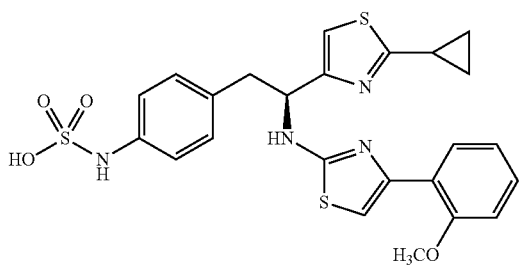

4-((S)-2-(2-cyclopropylthiazol-4-yl)-2-(4-(2-methoxyphenyl)thiazol-2-ylamino)ethyl)phenylsulfamic acid: $^1$H(CD$_3$OD): δ 7.89-7.87 (d, 1H, J=7.6 Hz), 7.28 (t, 1H, J=7.0 Hz), 7.10-6.96 (m, 8H), 5.03 (t, 1H, J=6.9 Hz), 3.90 (s, 1H), 3.19 (q, 2H, J=6.6 Hz), 2.38 (q, 1H, J=4.8 Hz), 1.21-1.14 (m, 2H), 1.06-1.00 (m, 2H).

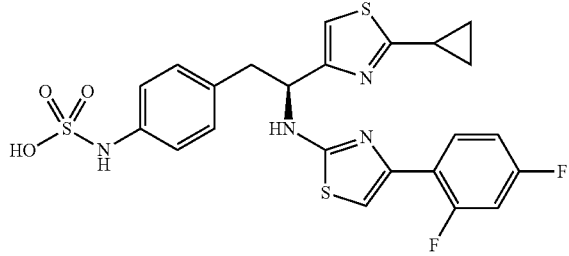

4-((S)-2-(2-cyclopropylthiazol-4-yl)-2-(4-(2,4-difluorophenyl)thiazol-2-ylamino)ethyl)phenylsulfamic acid: $^1$H(CD$_3$OD): δ 8.06-8.02 (q, 2H, J=6.9 Hz), 7.12-6.95 (m, 7H), 6.88 (s, 1H), 5.11 (t, 1H, J=6.9 Hz), 3.22-3.15 (m, 2H), 2.38 (q, 1H, J=4.8 Hz), 1.22-1.15 (m, 2H), 1.06-1.02 (m, 2H).

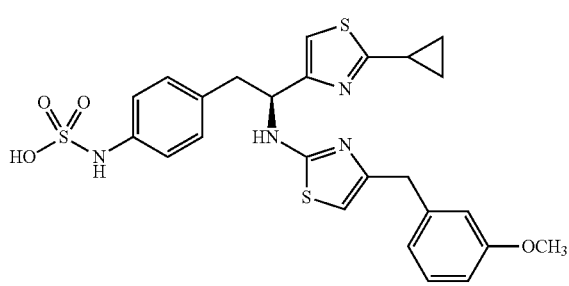

(S)-4-(2-(4-(3-methoxybenzyl)thiazol-2-ylamino)-2-(2-cyclopropylthiazol-4-yl)ethyl)phenylsulfamic acid: $^1$H(CD$_3$OD): δ 7.22-7.17 (m, 3H), 7.09-6.97 (m, 5H), 6.78-6.66 (m, 3H), 3.77 (s, 2H), 3.75 (s, 3H), 3.20-3.07 (m, 2H), 2.35 (q, 1H, J=4.8 Hz), 1.19-1.13 (m, 2H), 1.03-1.00 (m, 2H).

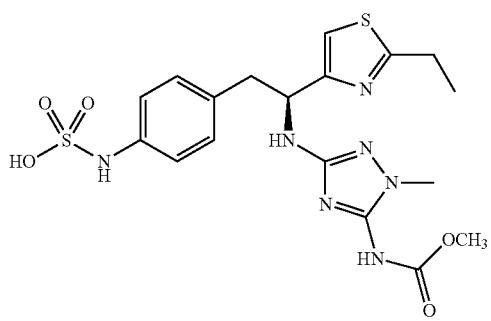

(S)-{5-[1-(2-Ethylthiazol-4-yl)-2-(4-sulfoaminophenyl)ethylamino]-2-methyl-2H-[1,2,4]triazole-3-yl}carbamic acid methyl ester: $^1$H NMR (300 MHz, MeOH-d$_4$) δ 6.97-7.08 (m, 5H), 3.71 (s, 3H), 3.51 (s, 3H), 3.15 (dd, J=13.5 and 6.3 Hz, 1H), 3.02-3.07 (m, 3H), 1.40 (t, J=6.6 Hz, 3H).

The second aspect of Category V of the present disclosure relates to compounds having the formula:

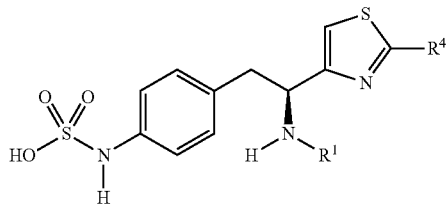

wherein R$^1$ is a substituted or unsubstituted heteroaryl and R$^4$ is substituted or unsubstituted phenyl and substituted or unsubstituted heteroaryl as further described herein below in Table X.

TABLE X

| No. | R$^4$ | R$^1$ |
|---|---|---|
| 471 | phenyl | 4-(methoxycarbonyl)thiazol-5-yl |
| 472 | phenyl | 4-[(2-methoxy-2-oxoethyl)carbamoyl]thiazol-5-yl |
| 473 | phenyl | 5-[1-N-(2-methoxy-2-oxoethyl)-1-H-indol-3-yl]oxazol-2-yl |
| 474 | phenyl | 5-(2-methoxyphenyl)oxazol-2-yl |
| 475 | phenyl | 5-[(S)-1-(tert-butoxycarbonyl)-2-phenylethyl]oxazol-2-yl |
| 476 | phenyl | 5-[4-(methylcarboxy)phenyl]oxazol-2-yl |
| 477 | phenyl | 5-(3-methoxybenzyl)oxazol-2-yl |
| 478 | phenyl | 5-(4-phenyl)oxazol-2-yl |
| 479 | phenyl | 5-(2-methoxyphenyl)thiazol-2-yl |
| 480 | phenyl | 5-(3-methoxyphenyl)thiazol-2-yl |
| 481 | phenyl | 5-(4-fluorophenyl)thiazol-2-yl |
| 482 | phenyl | 5-(2,4-difluorophenyl)thiazol-2-yl |
| 483 | phenyl | 5-(3-methoxybenzyl)thiazol-2-yl |
| 484 | phenyl | 4-(3-methoxyphenyl)thiazol-2-yl |
| 485 | phenyl | 4-(4-fluorophenyl)thiazol-2-yl |
| 486 | thiophene-2-yl | 4-(methoxycarbonyl)thiazol-5-yl |
| 487 | thiophene-2-yl | 4-[(2-methoxy-2-oxoethyl)carbamoyl]thiazol-5-yl |
| 488 | thiophene-2-yl | 5-[1-N-(2-methoxy-2-oxoethyl)-1-H-indol-3-yl]oxazol-2-yl |
| 489 | thiophene-2-yl | 5-(2-methoxyphenyl)oxazol-2-yl |
| 490 | thiophene-2-yl | 5-[(S)-1-(tert-butoxycarbonyl)-2-phenylethyl]oxazol-2-yl |
| 491 | thiophene-2-yl | 5-[4-(methylcarboxy)phenyl]oxazol-2-yl |
| 492 | thiophene-2-yl | 5-(3-methoxybenzyl)oxazol-2-yl |
| 493 | thiophene-2-yl | 5-(4-phenyl)oxazol-2-yl |
| 494 | thiophene-2-yl | 5-(2-methoxyphenyl)thiazol-2-yl |
| 495 | thiophene-2-yl | 5-(3-methoxyphenyl)thiazol-2-yl |
| 496 | thiophene-2-yl | 5-(4-fluorophenyl)thiazol-2-yl |
| 497 | thiophene-2-yl | 5-(2,4-difluorophenyl)thiazol-2-yl |

TABLE X-continued

| No. | R⁴ | R¹ |
|---|---|---|
| 498 | thiophene-2-yl | 5-(3-methoxybenzyl)thiazol-2-yl |
| 499 | thiophene-2-yl | 4-(3-methoxyphenyl)thiazol-2-yl |
| 500 | thiophene-2-yl | 4-(4-fluorophenyl)thiazol-2-yl |
| 501 | cyclopropyl | 4-(methoxycarbonyl)thiazol-5-yl |
| 502 | cyclopropyl | 4-[(2-methoxy-2-oxoethyl)carbamoyl]thiazol-5-yl |
| 503 | cyclopropyl | 5-[1-N-(2-methoxy-2-oxoethyl)-1-H-indol-3-yl]oxazol-2-yl |
| 504 | cyclopropyl | 5-(2-methoxyphenyl)oxazol-2-yl |
| 505 | cyclopropyl | 5-[(S)-1-(tert-butoxycarbonyl)-2-phenylethyl]oxazol-2-yl |
| 506 | cyclopropyl | 5-[4-(methylcarboxy)phenyl]oxazol-2-yl |
| 507 | cyclopropyl | 5-(3-methoxybenzyl)oxazol-2-yl |
| 508 | cyclopropyl | 5-(4-phenyl)oxazol-2-yl |
| 509 | cyclopropyl | 5-(2-methoxyphenyl)thiazol-2-yl |
| 510 | cyclopropyl | 5-(3-methoxyphenyl)thiazol-2-yl |
| 511 | cyclopropyl | 5-(4-fluorophenyl)thiazol-2-yl |
| 512 | cyclopropyl | 5-(2,4-difluorophenyl)thiazol-2-yl |
| 513 | cyclopropyl | 5-(3-methoxybenzyl)thiazol-2-yl |
| 514 | cyclopropyl | 4-(3-methoxyphenyl)thiazol-2-yl |
| 515 | cyclopropyl | 4-(4-fluorophenyl)thiazol-2-yl |

Compounds according to the second aspect of Category V which comprise a substituted or unsubstituted thiazol-4-yl unit for R¹ can be prepared by the procedure outlined in Schemes XIII, XIV, and XV and described herein below in Examples 13, 14, and 15.

Scheme XIII

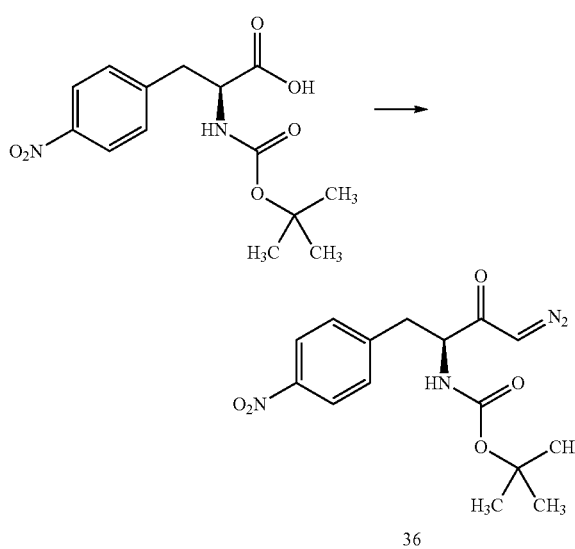

36

Reagents and conditions: (a) (i) (iso-butyl)OCOCl, Et₃N, THF; 0° C., 20 min. (ii) CH₂N₂; 0° C. to room temp for 3 hours.

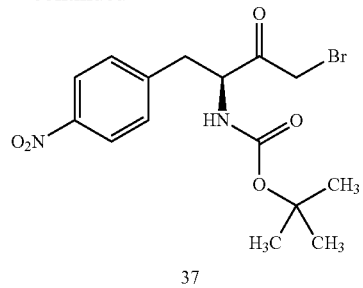

37

Reagents and conditions: (b) 48% HBr, THF; 0° C., 1.5 hr.

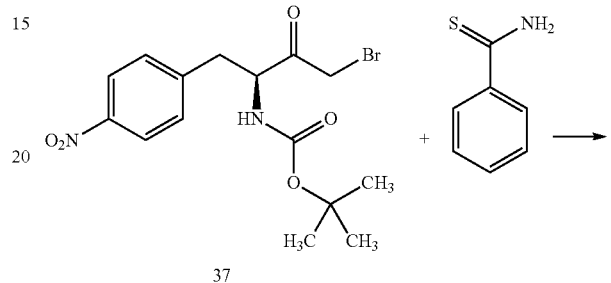

37

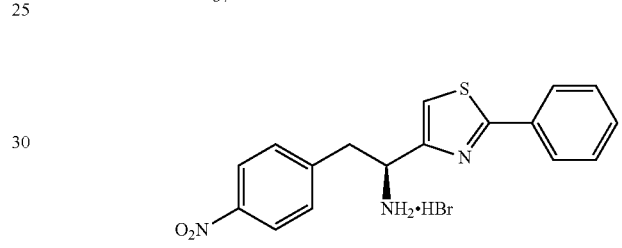

38

Reagents and conditions: (c) CH₃CN; reflux 2 hr.

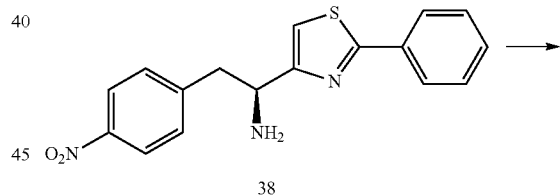

38

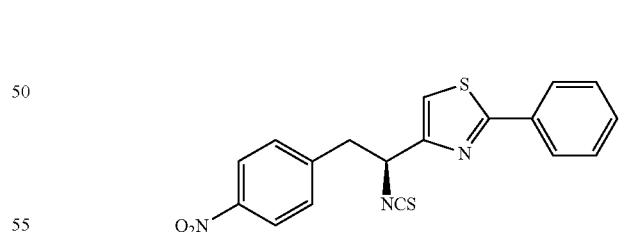

39

Reagents and conditions: (d) thiophosgene, CaCO₃, CCl₄, H₂O; rt, 18 hr.

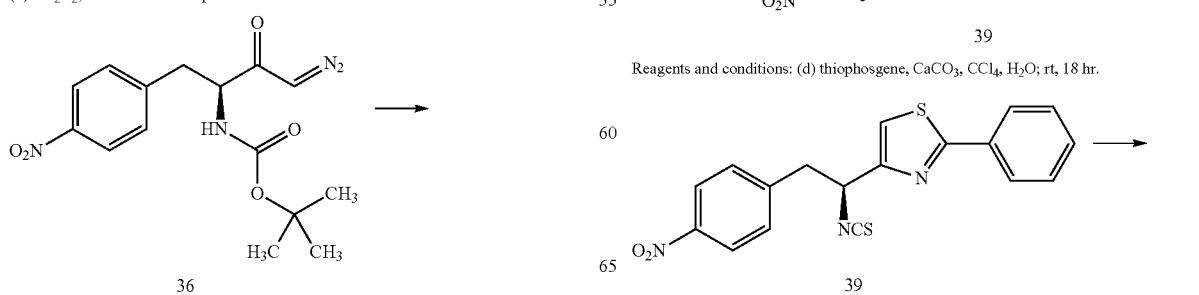

39

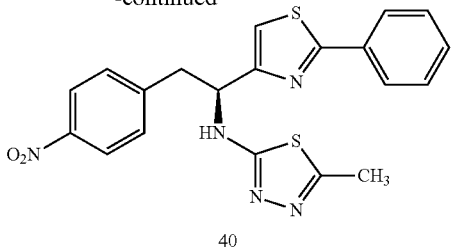

Reagents and conditions: (e) (i) CH₃C(O)NHNH₂, EtOH; reflux, 2 hr. (ii) POCl₃, rt 18 hr; 50° C. 2 hr.

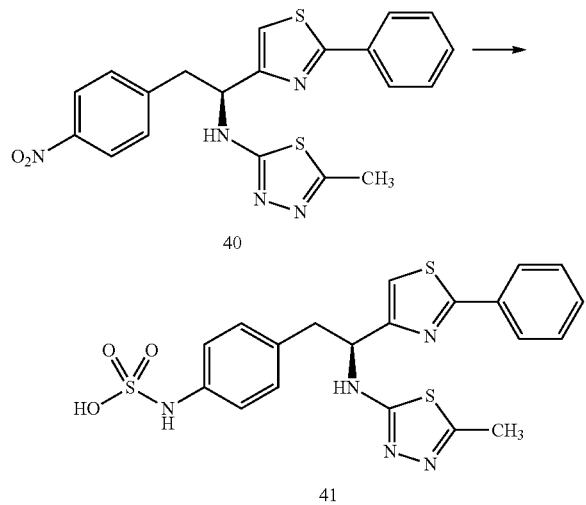

Reagents and conditions: (f) (i) H₂:Pd/C, MeOH; (ii) SO₃-pyridine, NH₄OH.

Example 13

(S)-4-(2-(5-Methyl-1,3,4-thiadiazol-2-ylamino)-2-(2-phenylthiazol-4-yl)ethyl)phenylsulfamic acid (41)

Preparation of [3-diazo-1-(4-nitrobenzyl)-2-oxo-propyl]-carbamic acid tert-butyl ester (36): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by isobutyl chloroformate (0.57 mL, 4.4 mmol). The reaction mixture is stirred at 0° C. for 20 minutes then filtered. The filtrate is treated with an ether solution of diazomethane (~16 mmol) at 0° C. The reaction mixture is stirred at room temperature for 3 hours and concentrated. The residue is dissolved in EtOAc and washed successively with water and brine, dried (Na₂SO₄), filtered and concentrated in vacuo. The resulting residue is purified over silica (hexane/EtOAc 2:1) to afford 1.1 g (82% yield) of the desired product as a slightly yellow solid. ¹H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of [3-bromo-1-(4-nitro-benzyl)-2-oxo-propyl]-carbamic acid tert-butyl ester (37): To a 0° C. solution of [3-diazo-1-(4-nitrobenzyl)-2-oxo-propyl]-carbamic acid tert-butyl ester, 36, (0.350 g, 1.04 mmol) in THF (5 mL) is added dropwise 48% aq. HBr (0.14 mL, 1.25 mmol). The reaction mixture is stirred at 0° C. for 1.5 hours and quenched at 0° C. with saturated aqueous Na₂CO₃. The mixture is extracted with EtOAc (3×25 mL) and the combined organic extracts are washed with brine, dried (Na₂SO₄), filtered and concentrated in vacuo to afford 0.400 g of the desired product that is used in the next step without further purification. ¹H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of (S)-2-(4-nitrophenyl)-1-(2-phenylthiazol-4-yl)ethanamine hydrobromide salt (38): A mixture of [3-bromo-1-(4-nitro-benzyl)-2-oxo-propyl]-carbamic acid tert-butyl ester, 37, (1.62 g, 4.17 mmol) and benzothioamide (0.630 g, 4.59 mmol), in CH₃CN (5 mL) is refluxed for 24 hours. The reaction mixture is cooled to room temperature and diethyl ether (50 mL) is added to the solution and the precipitate that forms is collected by filtration. The solid is dried under vacuum to afford 1.059 g (63%) of the desired product. ESI+MS 326 (M+1).

Preparation of (S)-4-[1-isothiocyanato-2-(4-nitrophenyl)-ethyl]-2-phenylthiazole (39): To a solution of (S)-2-(4-nitrophenyl)-1-(2-phenylthiazol-4-yl)ethanamine hydrobromide salt, 38, (2.03 g, 5 mmol) and CaCO₃ (1 g, 10 mmol) in CCl₄/water (10:7.5 mL) is added thiophosgene (0.46 mL, 6 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue that is purified over silica (CH₂Cl₂) to afford 1.71 g (93% yield) of the desired product. ESI+MS 368 (M+1).

Preparation of (S)-5-methyl-N-[2-(4-nitrophenyl)-1-(2-phenylthiazol-4-yl)ethyl]-1,3,4-thiadiazol-2-amine (40): A solution of (S)-4-[1-isothiocyanato-2-(4-nitrophenyl)-ethyl]-2-phenylthiazole, 39, (332 mg, 0.876 mmol) and acetic hydrazide (65 mg, 0.876 mmol) in EtOH (5 mL) is refluxed for 2 hours. The solvent is removed under reduced pressure, the residue is dissolved in POCl₃ (3 mL) and the resulting solution is stirred at room temperature for 18 hours after which the solution is heated to 50° C. for 2 hours. The solvent is removed in vacuo and the residue is dissolved in EtOAc (40 mL) and the resulting solution is treated with 1N NaOH until the pH remains approximately 8. The solution is extracted with EtOAc. The combined aqueous layers are washed with EtOAc, the organic layers combined, washed with brine, dried over MgSO₄, filtered, and concentrated in vacuo to afford 0.345 g (93% yield) of the desired product as a yellow solid. ¹H NMR (CDCl₃) 8.09 (d, J=8.4 Hz, 2H), 7.91 (m, 2H), 7.46 (m, 4H), 7.44 (s, 1H), 5.23 (m, 1H), 3.59 (m, 2H), 2.49 (s, 3H). ESI+MS 424 (M+1).

Preparation of (S)-4-[2-(5-methyl-1,3,4-thiadiazol-2-ylamino)-2-(2-phenylthiazol-4-yl)ethyl]phenylsulfamic acid (41): (S)-5-Methyl-N-[2-(4-nitrophenyl)-1-(2-phenylthiazol-4-yl)ethyl]-1,3,4-thiadiazol-2-amine, 40, (0.404 g, 0.954 mmol) is dissolved in MeOH (5 mL). Pd/C (50 mg, 10% w/w) is added and the mixture is stirred under a hydrogen atmosphere until the reaction is judged to be complete. The reaction mixture is filtered through a bed of CELITE™ and the solvent removed under reduced pressure. The crude product is dissolved in pyridine (4 mL) and treated with SO₃-pyridine (0.304 g, 1.91 mmol). The reaction is stirred at room temperature for 5 minutes after which a 7% solution of NH₄OH (50 mL) is added. The mixture is then concentrated and the resulting residue is purified by reverse phase preparative HPLC to afford 0.052 g (11% yield) of the desired product as the ammonium salt. ¹H(CD₃OD): δ 8.00-7.97 (m, 2H), 7.51-7.47 (m, 3H), 7.23 (s, 1H), 7.11-7.04 (q, 4H, J=9.0 Hz), 5.18 (t, 1H, J=7.2 Hz), 3.34-3.22 (m, 2H), 2.50 (s, 3H). ESI–MS 472 (M−1).

Scheme XIV

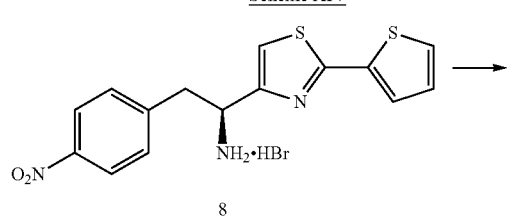

8

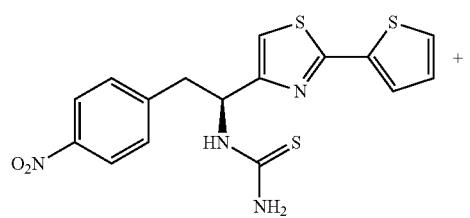

42

Reagents and conditions: (a) thiophosgene, CaCO₃, CCl₄/H₂O; rt, 18 hr.

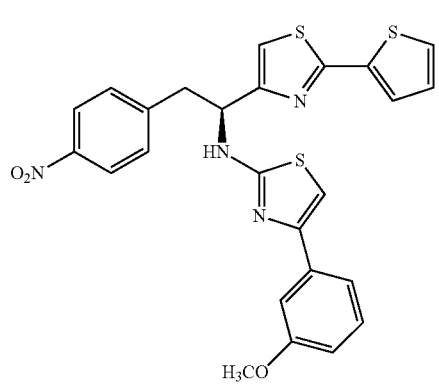

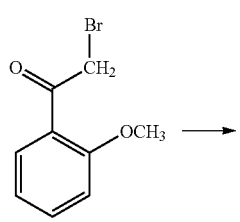

Reagents and conditions: (b) CH₃CN, reflux, 5 hours

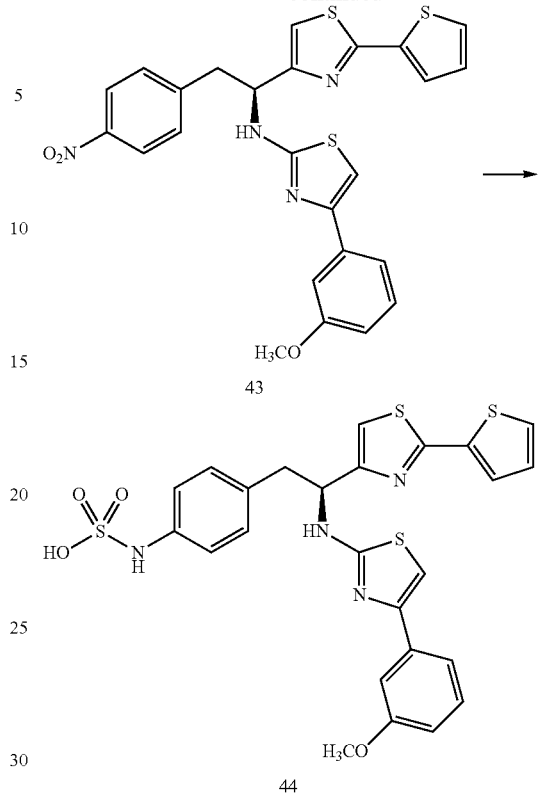

Reagents and conditions: (c) (i) H₂:Pd/C, MeOH; (ii) SO₃-pyridine, NH₄OH; rt, 18 hr.

Example 14

4-{(S)-2-[4-(2-Methoxyphenyl)thiazol-2-ylamino)-2-[2-(thiophen-2-yl)thiazol-4-yl]ethyl}phenylsulfamic acid (44)

Preparation of (S)-1-[1-(thiophen-2-ylthiazol-4-yl)-2-(4-nitrophenyl)ethyl]-thiourea (42): To a solution of (S)-2-(4-nitrophenyl)-1-(thiophen-2-ylthiazol-4-yl)ethanamine hydrobromide salt, 8, (1.23 g, 2.98 mmol) and CaCO₃ (0.597 g, 5.96 mmol) in CCl₄/water (10 mL/5 mL) is added thiophosgene (0.412 g, 3.58 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is subsequently treated with ammonia (0.5M in 1,4-dioxane, 29.4 mL, 14.7 mmol) which is purified over silica to afford 0.490 g of the desired product as a red-brown solid. ESI+MS 399 (M+1).

Preparation of 4-(2-methoxyphenyl)-N-{(S)-2-(4-nitrophenyl)-1-[2-(thiophen-2-yl)thiazol-4-yl]ethyl}thiazol-2-amine (43): (S)-1-[1-(thiophen-2-ylthiazol-4-yl)-2-(4-nitrophenyl)ethyl]-thiourea, 42, (265 mg, 0.679 mmol) is treated with bromo-2'-methoxyacetophenone (171 mg, 0.746 mmol) to afford 0.221 g of the product as a yellow solid. ESI+MS 521 (M+1).

Preparation on 4-{(S)-2-[4-(2-methoxyphenyl)thiazol-2-ylamino)-2-[2-(thiophen-2-yl)thiazol-4-yl]ethyl}phenylsulfamic acid (44): 4-(2-methoxyphenyl)-N-{(S)-2-(4-nitrophenyl)-1-[2-(thiophen-2-yl)thiazol-4-yl]ethyl}thiazol-2-amine, 43, (0.229 g) is dissolved in 12 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 6 mL pyridine and treated with SO$_3$-pyridine (140 mg). The reaction is stirred at room temperature for 5 minutes after which 10 mL of a 7% solution of NH$_4$OH is added. The mixture is then concentrated and the resulting residue is purified by reverse-phase chromatography to afford 0.033 g of the desired product as the ammonium salt. $^1$H(CD$_3$OD): δ 7.96-7.93 (m, 1H), 7.60-7.55 (m, 2H), 7.29-7.23 (m, 1H), 7.18-6.95 (m, 9H), 5.15 (t, 1H, J=6.9 Hz), 3.90 (s, 3H), 3.35-3.24 (m, 2H).

Compounds according to the second aspect of Category V which comprise a substituted or unsubstituted oxazol-2-yl unit for R$^1$ can be prepared by the procedure outlined in Scheme XV and described herein below in Example 15. Intermediate 39 can be prepared according to Scheme XIII and Example 13.

Scheme XV

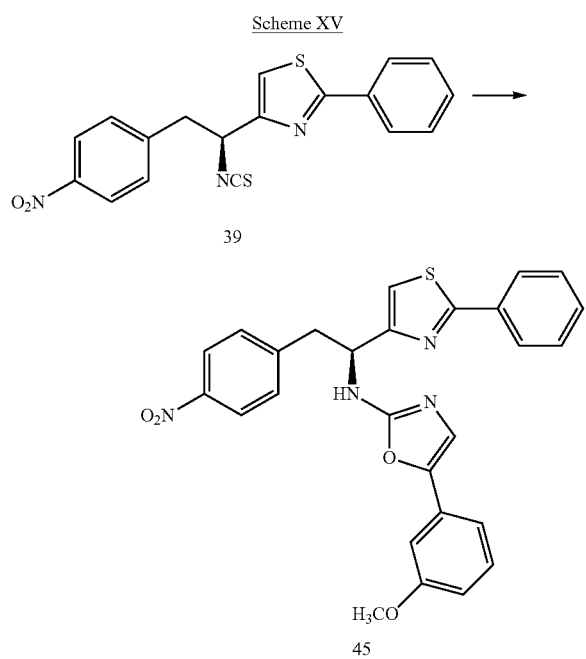

Reagents and conditions: (a) 1-azido-1-(3-methoxyphenyl)ethanone, PPh$_3$, dioxane, 90° C. 20 minutes.

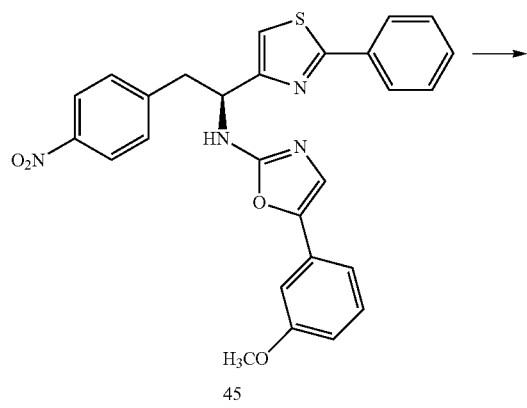

Reagents and conditions: (b) (i) H$_2$:Pd/C, MeOH; (ii) SO$_3$-pyridine, NH$_4$OH; rt, 18 hr.

Example 15

4-{(S)-2-[5-(3-Methoxyphenyl)oxazole-2-ylamino]-2-(2-phenylthiazole-4-yl)ethyl}phenylsulfamic acid (46)

Preparation of [5-(3-methoxyphenyl)oxazol-2-yl]-[2-(4-nitrophenyl)-1-(2-phenylthiazole-4-yl)ethyl]amine (45): A mixture of (S)-4-(isothiocyanato-2-(4-nitrophenyl)ethyl)-2-phenylthiazole, 39, (300 mg, 0.81 mmol), 1-azido-1-(3-methoxyphenyl)ethanone (382 mg, 2.0 mmol) and PPh$_3$ (0.8 g, polymer bound, ~3 mmol/g) in dioxane (6 mL) is heated at 90° C. for 20 minutes. The reaction solution is cooled to room temperature and the solvent removed in vacuo and the resulting residue is purified over silica to afford 300 mg (74% yield) of the desired product as a yellow solid. $^1$H NMR (300 MHz, MeOH-d$_4$) δ 8.02 (d, J=7.2 Hz, 2H), 7.92-7.99 (m, 2H), 7.42-7.47 (m, 3H), 7.22-7.27 (m, 3H), 6.69-7.03 (m, 4H), 6.75-6.78 (m, 1H), 5.26 (t, J=6.3 Hz, 1H), 3.83 (s, 4H), 3.42-3.45 (m, 2H).

Preparation of 4-{(S)-2-[5-(3-methoxyphenyl)oxazole-2-ylamino]-2-(2-phenylthiazole-4-yl)ethyl}phenylsulfamic acid (46): [5-(3-methoxyphenyl)oxazol-2-yl]-[2-(4-nitrophenyl)-1-(2-phenylthiazole-4-yl)ethyl]amine, 45, (300 mg, 0.60 mmol) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (10 mL) and treated with SO$_3$-pyridine (190 mg, 1.2 mmol). The reaction is stirred at room temperature for 5 minutes after which a 7% solution of NH$_4$OH is added. The mixture is then concentrated and the resulting residue is purified by reverse-phase chromatography to afford 0.042 g of the desired product as the ammonium salt. $^1$H NMR (300 MHz, MeOH-d$_4$) δ 7.99 (d, J=7.5 Hz, 2H), 7.46-7.50 (m, 3H), 7.23-7.29 (m, 3H), 7.04-7.12 (m, 6H), 6.78 (dd, J=8.4 and 2.4 Hz, 1H), 5.16 (t, J=6.6 Hz, 1H), 3.81 (s, 3H), 3.29-3.39 (m, 1H), 3.17 (dd, J=13.8 and 8.1 Hz, 1H).

Further to the preparation of compounds which encompass Category V of the present disclosure, compounds of the present disclosure comprising R$^1$ units having non-exemplified units can be prepared by modifying the procedures described herein above. For example, compounds of Category V comprising substituted or unsubstituted [1,2,4]triazole-3-yl units can be prepared by s The following are non-limiting examples of the second aspect of Category V of the present disclosure.

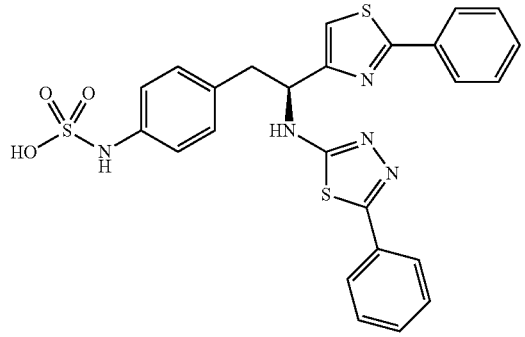

(S)-4-(2-(5-Phenyl-1,3,4-thiadiazol-2-ylamino)-2-(2-phenylthiazol-4-yl)ethyl)-phenylsulfamic acid: $^1$H(CD$_3$OD): δ 7.97-7.94 (m, 2H), 7.73-7.70 (m, 2H), 7.44-7.39 (m, 6H), 7.25 (s, 1H), 7.12 (s, 4H), 5.29 (t, 1H, J=6.9 Hz), 3.35-3.26 (m, 2H).

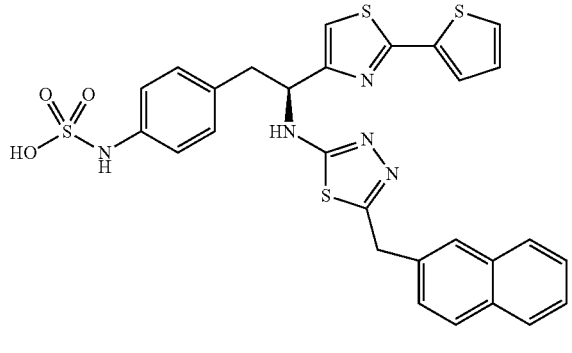

4-((S)-2-(5-(Naphthalen-1-ylmethyl)-1,3,4-thiadiazol-2-ylamino)-2-(2-(thiophen-2-yl)thiazol-4-yl)ethyl)phenylsulfamic acid: $^1$H(CD$_3$OD): δ 8.08-8.05 (m, 1H), 7.89-7.80 (m, 2H), 7.55-7.43 (m, 6H), 7.11-7.00 (m, 6H), 5.08 (t, 1H, J=7.1 Hz), 4.63 (s, 2H), 3.26-3.08 (m, 2H).

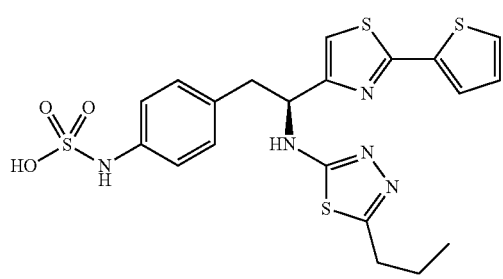

4-((S)-2-(5-Propyl-1,3,4-thiadiazol-2-ylamino)-2-(2-(thiophen-2-yl)thiazol-4-yl)ethyl)phenylsulfamic acid: $^1$H(CD$_3$OD): δ 7.59-7.54 (m, 2H), 7.17-7.03 (m, 6H), 5.13 (t, 1H, J=7.2 Hz), 3.32-3.13 (m, 2H), 2.81 (t, 2H, J=7.4 Hz), 1.76-1.63 (h, 6H, J=7.4 Hz), 0.97 (t, 3H, J=7.3 Hz).

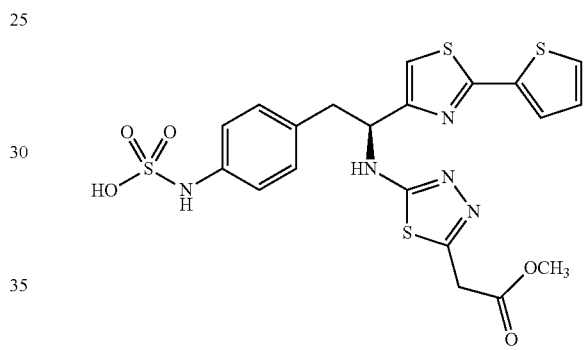

4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid: $^1$H(CD$_3$OD): δ 7.48-7.44 (m, 2H), 7.03-6.92 (m, 6H), 5.02 (t, 1H, J=7.2 Hz), 4.30 (s, 2H), 3.55 (s, 3H), 3.22-3.02 (m, 2H).

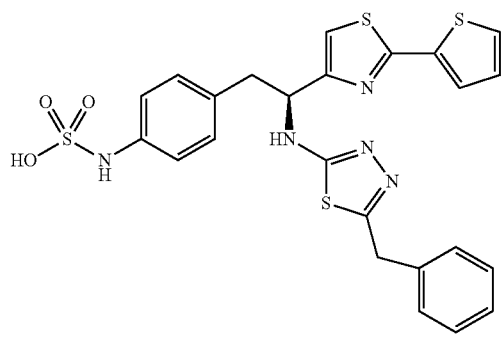

4-((S)-2-(5-Benzyl-1,3,4-thiadiazol-2-ylamino)-2-(2-(thiophen-2-yl)thiazol-4-yl)ethyl)phenylsulfamic acid: $^1$H(CD$_3$OD): 6 (m, 2H), 7.49-7.45 (m, 2H), 7.26-7.16 (m, 5H), 7.05-6.94 (m, 6H), 5.04 (t, 1H, J=7.1 Hz), 4.07 (s, 2H), 3.22-3.04 (m, 2H).

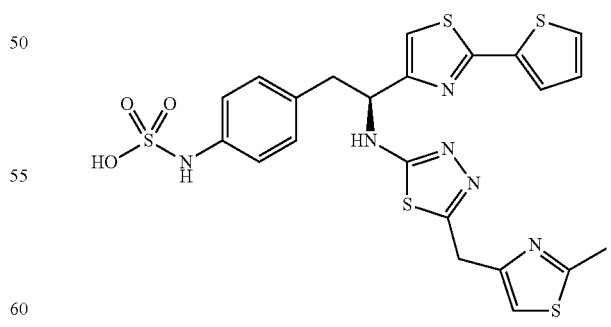

4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid: $^1$H(CD$_3$OD): δ 7.60-7.56 (m, 2H), 7.19 (s, 1H), 7.15-7.12 (m, 2H), 7.09-7.03 (q, 4H, J=8.7 Hz), 5.14 (t, 1H, J=7.2 Hz), 4.28 (s, 2H), 3.33-3.14 (m, 2H), 2.67 (s, 3H).

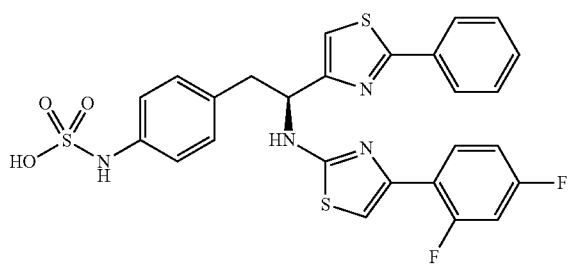

4-{(S)-2-[4-(2,4-Difluorophenyl)thiazol-2-ylamino]-2-[2-(thiophen-2-yl)thiazol-4-yl]ethyl}phenylsulfamic acid: ¹H(CD₃OD): δ 8.06-8.02 (q, 1H, J=6.8 Hz), 7.59-7.54 (m, 2H), 7.16-7.08 (m, 6H), 7.01-6.88 (m, 4H), 5.20 (t, 1H, J=7.0 Hz), 3.36-3.17 (m, 2H).

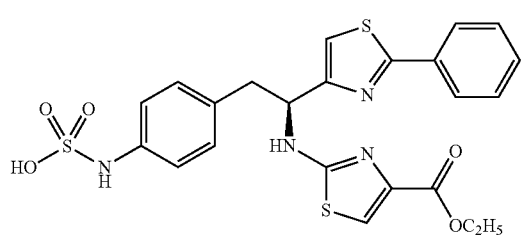

(S)-4-{2-[4-(Ethoxycarbonyl)thiazol-2-ylamino]-2-(2-phenylthiazol-4-yl)ethyl}phenylsulfamic acid: ¹H(CD₃OD): δ 8.02-7.99 (m, 2H), 7.54-7.45 (m, 4H), 7.26 (s, 1H), 7.08 (s, 4H), 5.26 (t, 1H, J=6.9 Hz), 4.35-4.28 (q, 2H, J=6.9 Hz), 3.38-3.18 (m, 2H), 1.36 (t, 3H, J=7.2 Hz).

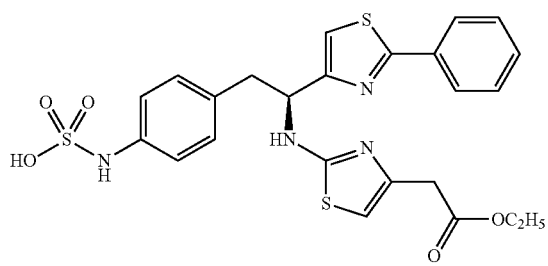

(S)-4-{2-[4-(2-Ethoxy-2-oxoethyl)thiazol-2-ylamino]-2-(2-phenylthiazol-4-yl)ethyl}phenylsulfamic acid: ¹H(CD₃OD): δ 7.96 (m, 2H), 7.50-7.46 (m, 3H), 7.21 (s, 1H), 7.10-7.04 (m, 4H), 6.37 (s, 1H), 5.09 (t, 1H, J=6.9 Hz), 4.17-4.10 (q, 2H, J=7.1 Hz), 3.54 (s, 2H), 3.35-3.14 (m, 2H), 1.22 (t, 3H, J=7.1 Hz).

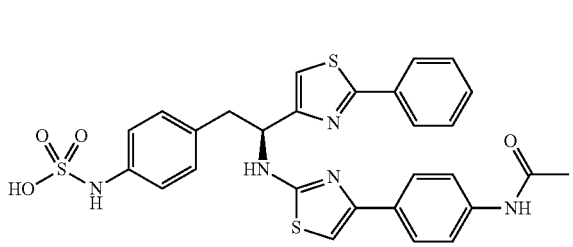

(S)-4-{2-[4-(4-acetamidophenyl)thiazol-2-ylamino]-2-(2-phenylthiazol-4-yl)ethyl}phenylsulfamic acid: ¹H(CD₃OD): δ 8.11 (m, 2H), 7.82-7.80 (m, 2H), 7.71-7.61 (m, 6H), 7.40 (s, 1H), 7.23 (s, 4H), 5.32 (t, 1H, J=7.0 Hz), 3.51-3.35 (m, 2H), 2.28 (s, 3H).

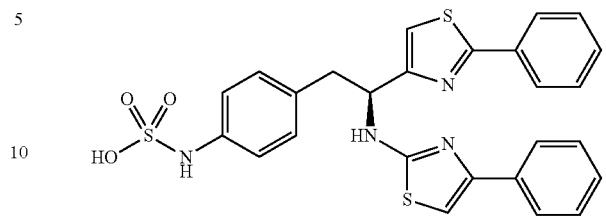

(S)-4-[2-(4-phenylthiazol-2-ylamino)-2-(2-phenylthiazol-4-yl)ethyl]phenyl-sulfamic acid: ¹H(CD₃OD): δ 8.03-7.99 (m, 2H), 7.75-7.72 (d, 2H, J=8.4 Hz), 7.53-7.48 (m, 3H), 7.42 (m, 4H), 7.12 (s, 4H), 6.86 (s, 1H), 5.23 (t, 1H, J=7.2 Hz), 3.40-3.27 (m, 2H).

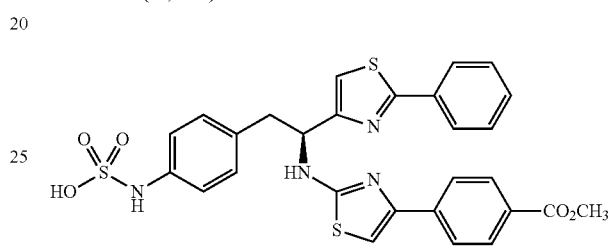

(S)-4-{2-[4-(4-(methoxycarbonyl)phenyl)thiazol-2-ylamino]-2-(2-phenylthiazol-4-yl)ethyl}phenylsulfamic acid: ¹H(CD₃OD): δ 8.04-8.00 (m, 4H), 7.92-7.89 (d, 2H, J=9.0 Hz), 7.53-7.49 (m, 3H), 7.30 (s, 1H), 7.15 (s, 4H), 7.05 (s, 1H), 5.28 (t, 1H, J=6.9 Hz), 3.93 (s, 3H), 3.35-3.24 (m, 2H).

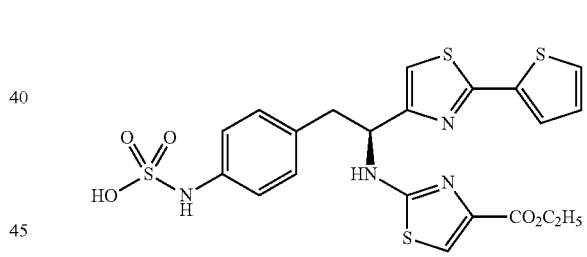

4-{(S)-2-[4-(Ethoxycarbonyl)thiazol-2-ylamino]-2-[2-(thiophen-2-yl)thiazol-4-yl]ethyl}phenylsulfamic acid: ¹H(CD₃OD): δ 7.43-7.38 (m, 2H), 7.26 (s, 1H), 7.00-6.94 (m, 3H), 6.89 (s, 4H), 5.02 (t, 1H, J=7.0 Hz), 4.16-4.09 (q, 2H, J=7.1 Hz), 3.14-2.94 (m, 2H), 1.17 (t, 3H, J=7.1 Hz).

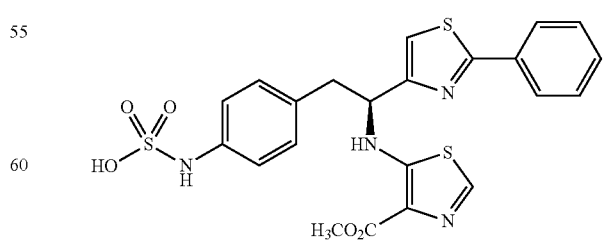

(S)-4-[2-(4-(Methoxycarbonyl)thiazol-5-ylamino)-2-(2-phenylthiazole-4-yl)ethyl]phenylsulfamic acid: ¹H NMR (300 MHz, MeOH-d₄) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

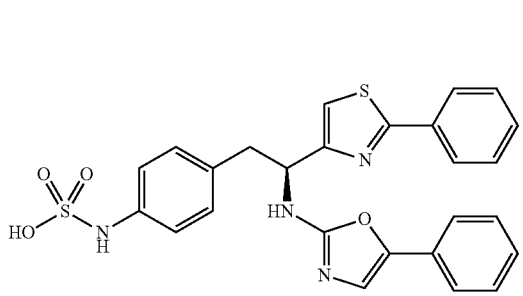

(S)-4-[2-(5-Phenyl oxazol-2-ylamino)-2-(2-phenylthiazol-4-yl)ethyl]-phenylsulfamic acid: ¹H NMR (300 MHz, MeOH-d₄) δ 7.94-7.96 (m, 2H), 7.45-7.49 (m, 5H), 7.32 (t, J=7.8 Hz, 2H), 7.12 (s, 1H), 7.19 (t, J=7.2 Hz, 1H), 7.12 (s, 4H), 7.05 (s, 1H), 5.15 (t, J=6.4 Hz, 1H), 3.34 (dd, J=14.1 and 8.4 Hz, 1H), 3.18 (dd, J=14.1 and 8.4 Hz, 1H).

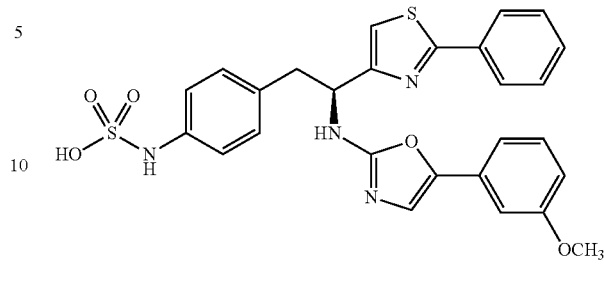

4-{(S)-2-[5-(3-Methoxyphenyl)oxazol-2-ylamino]-2-[(2-thiophen-2-yl)thiazole-4-yl]ethyl}phenylsulfamic acid: ¹H NMR (300 MHz, MeOH-d₄) δ 7.55-7.60 (m, 2H), 7.26 (t, J=8.1 Hz, 1H), 7.21 (s, 1H), 7.04-7.15 (m, 8H), 6.77-6.81 (m, 1H), 5.10 (t, J=6.3 Hz, 1H), 3.81 (s, 3H), 3.29-3.36 (m, 1H), 3.15 (dd, J=14.1 and 8.4 Hz, 1H).

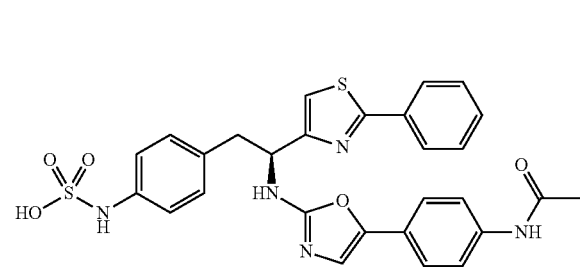

(S)-4-{2-[5-(4-Acetamidophenyl)oxazol-2-ylamino]-2-(2-phenylthiazol-4-yl)ethyl}phenylsulfamic acid: ¹H NMR (300 MHz, MeOH-d₄) δ 7.92-7.94 (m, 2H), 7.55-7.58 (m, 2H), 7.39-7.50 (m, 5H), 7.26 (s, 1H), 7.12 (s, 4H), 7.02 (s, 1H0), 5.14 (t, J=7.8 Hz, 1H), 3.13-3.38 (m, 2H), 2.11 (s, 3H).

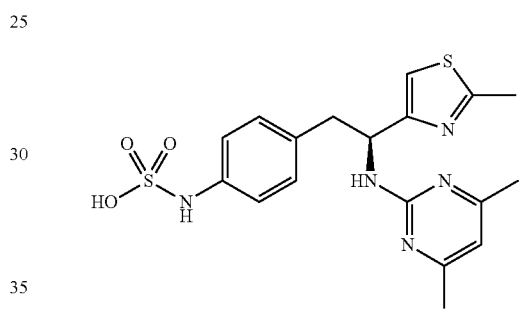

(S)-4-[2-(4,6-Dimethylpyrimidin-2-ylamino)-2-(2-methylthiazole-4-yl)ethyl]phenylsulfamic acid: ¹H NMR (300 MHz, MeOH-d₄) δ 7.00-7.10 (m, 5H), 6.44 (s, 1H), 5.50 (t, J=7.2 Hz, 1H), 3.04-3.22 (m, 2H), 2.73 (s, 3H), 2.27 (s, 6H).

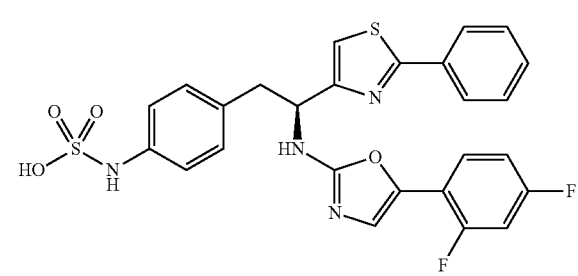

4-((S)-2-(5-(2,4-Difluorophenyl)oxazole-2-ylamino)-2-(2-phenylthiazol-4-yl)ethyl)phenylsulfamic acid: ¹H NMR (300 MHz, MeOH-d₄) δ 7.97-7.99 (m, 2H), 7.54-7.62 (m, 1H), 7.45-7.50 (m, 3H), 7.28 (s, 1H), 7.12 (s, 4H), 6.97-7.06 (m, 3H), 5.15-5.20 (m, 1H), 3.28-3.40 (m, 1H), 3.20 (dd, J=13.8 and 8.4 Hz, 1H).

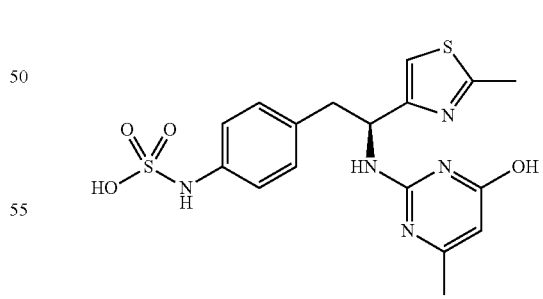

(S)-4-[2-(4-Hydroxy-6-methylpyrimidine-2-ylamino)-2-(2-methylthiazole-4-yl)ethyl]phenylsulfamic acid: ¹H NMR (300 MHz, MeOH-d₄) δ 7.44 (d, J=8.4 Hz, 2H), 6.97-7.10 (m, 4H), 5.61 (s, 1H), 5.40-5.49 (m, 1H), 3.10-3.22 (m, 2H), 2.73 (s, 3H), 2.13 (s, 3H).

The first aspect of Category VI of the present disclosure relates to compounds having the formula:

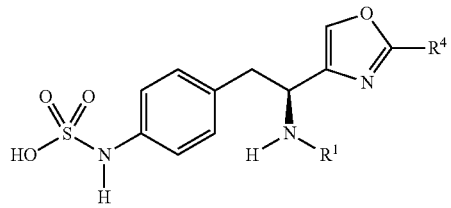

wherein $R^1$ is heteroaryl and $R^4$ is further described herein below in Table XI.

TABLE XI

| No. | $R^4$ | $R^1$ |
|---|---|---|
| 516 | phenyl | 4-(methoxycarbonyl)thiazol-5-yl |
| 517 | phenyl | 4-[(2-methoxy-2-oxoethyl)carbamoyl]thiazol-5-yl |
| 518 | phenyl | 5-[1-N-(2-methoxy-2-oxoethyl)-1-H-indol-3-yl]oxazol-2-yl |
| 519 | phenyl | 5-(2-methoxyphenyl)oxazol-2-yl |
| 520 | phenyl | 5-[(S)-1-(tert-butoxycarbonyl)-2-phenylethyl]oxazol-2-yl |
| 521 | phenyl | 5-[4-(methylcarboxy)phenyl]oxazol-2-yl |
| 522 | phenyl | 5-(3-methoxybenzyl)oxazol-2-yl |
| 523 | phenyl | 5-(4-phenyl)oxazol-2-yl |
| 524 | phenyl | 5-(2-methoxyphenyl)thiazol-2-yl |
| 525 | phenyl | 5-(3-methoxyphenyl)thiazol-2-yl |
| 526 | phenyl | 5-(4-fluorophenyl)thiazol-2-yl |
| 527 | phenyl | 5-(2,4-difluorophenyl)thiazol-2-yl |
| 528 | phenyl | 5-(3-methoxybenzyl)thiazol-2-yl |
| 529 | phenyl | 4-(3-methoxyphenyl)thiazol-2-yl |
| 530 | phenyl | 4-(4-fluorophenyl)thiazol-2-yl |
| 531 | thiophene-2-yl | 4-(methoxycarbonyl)thiazol-5-yl |
| 532 | thiophene-2-yl | 4-[(2-methoxy-2-oxoethyl)carbamoyl]thiazol-5-yl |
| 533 | thiophene-2-yl | 5-[1-N-(2-methoxy-2-oxoethyl)-1-H-indol-3-yl]oxazol-2-yl |
| 534 | thiophene-2-yl | 5-(2-methoxyphenyl)oxazol-2-yl |
| 535 | thiophene-2-yl | 5-[(S)-1-(tert-butoxycarbonyl)-2-phenylethyl]oxazol-2-yl |
| 536 | thiophene-2-yl | 5-[4-(methylcarboxy)phenyl]oxazol-2-yl |
| 537 | thiophene-2-yl | 5-(3-methoxybenzyl)oxazol-2-yl |
| 538 | thiophene-2-yl | 5-(4-phenyl)oxazol-2-yl |
| 539 | thiophene-2-yl | 5-(2-methoxyphenyl)thiazol-2-yl |
| 540 | thiophene-2-yl | 5-(3-methoxyphenyl)thiazol-2-yl |
| 541 | thiophene-2-yl | 5-(4-fluorophenyl)thiazol-2-yl |
| 542 | thiophene-2-yl | 5-(2,4-difluorophenyl)thiazol-2-yl |
| 543 | thiophene-2-yl | 5-(3-methoxybenzyl)thiazol-2-yl |
| 544 | thiophene-2-yl | 4-(3-methoxyphenyl)thiazol-2-yl |
| 545 | thiophene-2-yl | 4-(4-fluorophenyl)thiazol-2-yl |
| 546 | cyclopropyl | 4-(methoxycarbonyl)thiazol-5-yl |
| 547 | cyclopropyl | 4-[(2-methoxy-2-oxoethyl)carbamoyl]thiazol-5-yl |
| 548 | cyclopropyl | 5-[1-N-(2-methoxy-2-oxoethyl)-1-H-indol-3-yl]oxazol-2-yl |
| 549 | cyclopropyl | 5-(2-methoxyphenyl)oxazol-2-yl |
| 550 | cyclopropyl | 5-[(S)-1-(tert-butoxycarbonyl)-2-phenylethyl]oxazol-2-yl |
| 551 | cyclopropyl | 5-[4-(methylcarboxy)phenyl]oxazol-2-yl |
| 552 | cyclopropyl | 5-(3-methoxybenzyl)oxazol-2-yl |
| 553 | cyclopropyl | 5-(4-phenyl)oxazol-2-yl |
| 554 | cyclopropyl | 5-(2-methoxyphenyl)thiazol-2-yl |
| 555 | cyclopropyl | 5-(3-methoxyphenyl)thiazol-2-yl |
| 556 | cyclopropyl | 5-(4-fluorophenyl)thiazol-2-yl |
| 557 | cyclopropyl | 5-(2,4-difluorophenyl)thiazol-2-yl |
| 558 | cyclopropyl | 5-(3-methoxybenzyl)thiazol-2-yl |
| 559 | cyclopropyl | 4-(3-methoxyphenyl)thiazol-2-yl |
| 560 | cyclopropyl | 4-(4-fluorophenyl)thiazol-2-yl |

Compounds according to the first aspect of Category VI can be prepared by the procedure outlined in Scheme XVI and described herein below in Example 16.

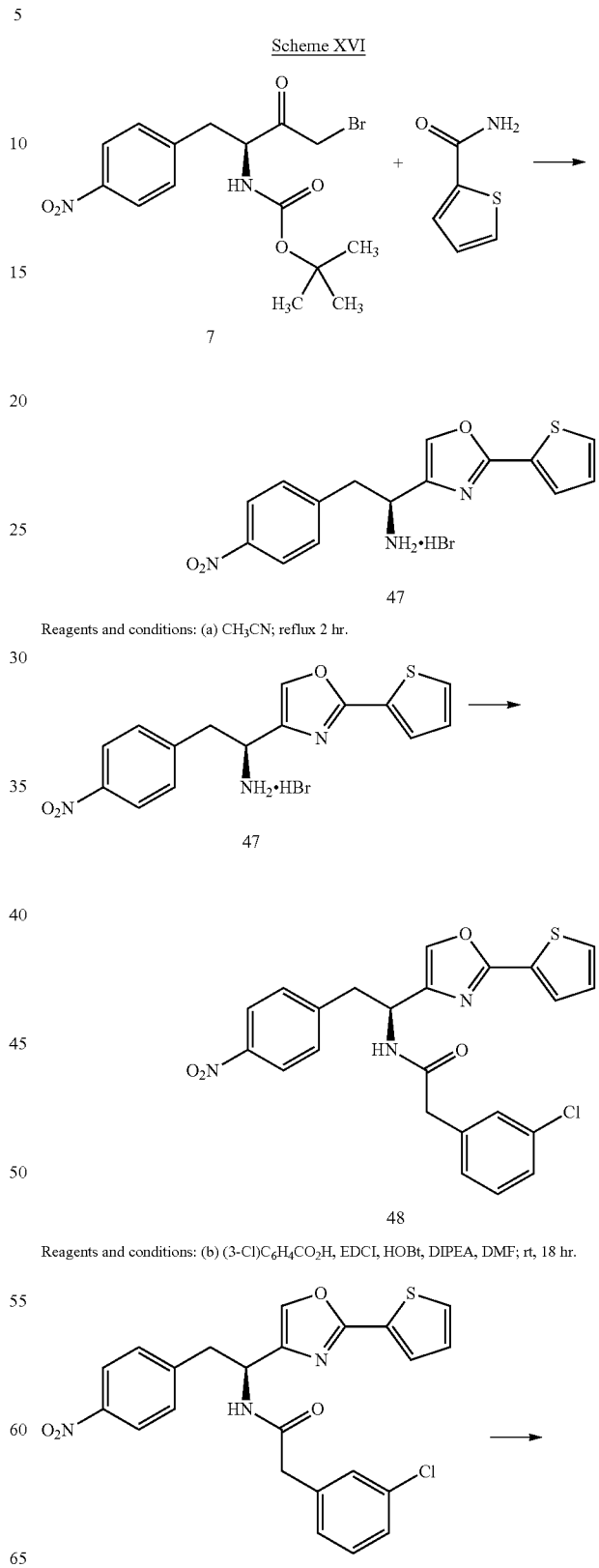

Scheme XVI

Reagents and conditions: (a) $CH_3CN$; reflux 2 hr.

Reagents and conditions: (b) $(3\text{-}Cl)C_6H_4CO_2H$, EDCI, HOBt, DIPEA, DMF; rt, 18 hr.

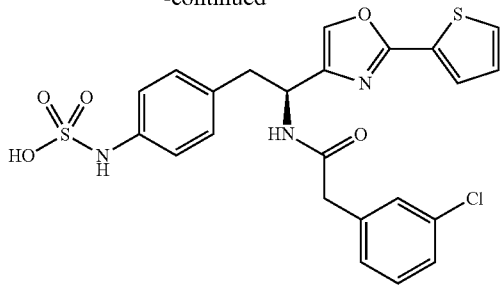

49

Reagents and conditions: (c) (i) H₂:Pd/C, MeOH; (ii) SO₃-pyridine, NH₄OH, rt, 18 hr.

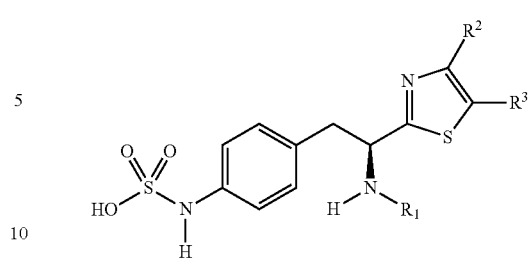

wherein $R^1$ is aryl and $R^2$ and $R^3$ are further described herein below in Table XII.

Example 16

4-((S)-2-(2-(3-Chlorophenyl)acetamido)-2-(2-(thiophene-2-yl)oxazol-4-yl)ethyl)phenylsulfamic acid (49)

Preparation of (S)-2-(4-nitrophenyl)-1-[(thiophene-2-yl)oxazol-4-yl]ethanamine hydrobromide salt (47): A mixture of (S)-tert-butyl 4-bromo-1-(4-nitrophenyl)-3-oxobutan-2-ylcarbamate, 7, (38.7 g, 100 mmol), and thiophene-2-carboxamide (14 g, 110 mmol) (available from Alfa Aesar) in CH₃CN (500 mL) is refluxed for 5 hours. The reaction mixture is cooled to room temperature and diethyl ether (200 mL) is added to the solution. The precipitate which forms is collected by filtration. The solid is dried under vacuum to afford the desired product which can be used for the next step without purification.

Preparation of 2-(3-chlorophenyl)-N-{(S)-2-(4-nitrophenyl)-1-[2-(thiophene-2-yl)oxazol-4-yl]ethyl}acetamide (48): To a solution of (S)-2-(4-nitrophenyl)-1-[(thiophene-2-yl)oxazol-4-yl]ethanamine HBr, 47, (3.15 g, 10 mmol) 3-chlorophenyl-acetic acid (1.70 g, 10 mmol) and 1-hydroxybenzotriazole (HOBt) (0.70 g, 5.0 mmol) in DMF (50 mL) at 0° C., is added 1-(3-dimethylaminopropyl)-3-ethylcarbodiimide (EDCI) (1.90 g, 10 mmol) followed by triethylamine (4.2 mL, 30 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of -((S)-2-(2-(3-chlorophenyl)acetamido)-2-(2-(thiophene-2-yl)oxazol-4-yl)ethyl)phenylsulfamic acid (49): 2-(3-chlorophenyl)-N-{(S)-2-(4-nitrophenyl)-1-[2-(thiophene-2-yl)oxazol-4-yl]ethyl}acetamide, 48, (3 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue can be purified by reverse phase chromatography to afford the desired product as the ammonium salt.

The second aspect of Category VI of the present disclosure relates to compounds having the formula:

TABLE XII

| No. | $R^2$ | $R^3$ | $R^1$ |
|---|---|---|---|
| 561 | methyl | hydrogen | phenyl |
| 562 | methyl | hydrogen | benzyl |
| 563 | methyl | hydrogen | 2-fluorophenyl |
| 564 | methyl | hydrogen | 3-fluorophenyl |
| 565 | methyl | hydrogen | 4-fluorophenyl |
| 566 | methyl | hydrogen | 2-chlorophenyl |
| 567 | methyl | hydrogen | 3-chlorophenyl |
| 568 | methyl | hydrogen | 4-chlorophenyl |
| 569 | ethyl | hydrogen | phenyl |
| 570 | ethyl | hydrogen | benzyl |
| 571 | ethyl | hydrogen | 2-fluorophenyl |
| 572 | ethyl | hydrogen | 3-fluorophenyl |
| 573 | ethyl | hydrogen | 4-fluorophenyl |
| 574 | ethyl | hydrogen | 2-chlorophenyl |
| 575 | ethyl | hydrogen | 3-chlorophenyl |
| 576 | ethyl | hydrogen | 4-chlorophenyl |
| 577 | thiene-2-yl | hydrogen | phenyl |
| 578 | thiene-2-yl | hydrogen | benzyl |
| 579 | thiene-2-yl | hydrogen | 2-fluorophenyl |
| 580 | thiene-2-yl | hydrogen | 3-fluorophenyl |
| 581 | thiene-2-yl | hydrogen | 4-fluorophenyl |
| 582 | thiene-2-yl | hydrogen | 2-chlorophenyl |
| 583 | thiene-2-yl | hydrogen | 3-chlorophenyl |
| 584 | thiene-2-yl | hydrogen | 4-chlorophenyl |

Compounds according to the second aspect of Category VI can be prepared by the procedure outlined in Scheme XVII and described herein below in Example 17.

Scheme XVII

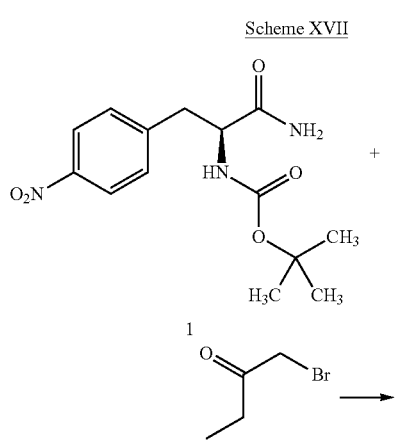

105
-continued

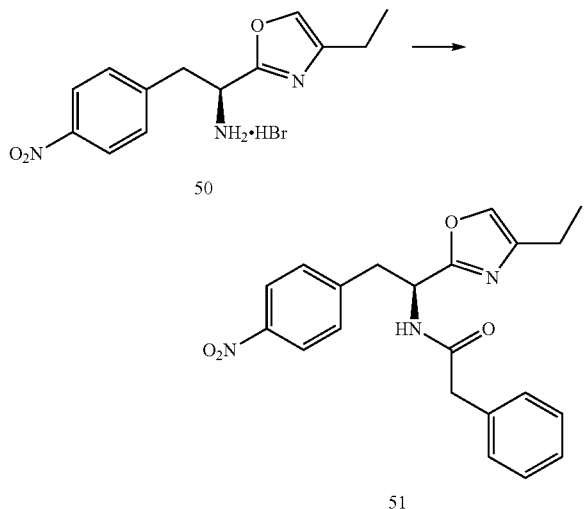

Reagents and conditions: (a) CH₃CN; reflux, 2 hr.

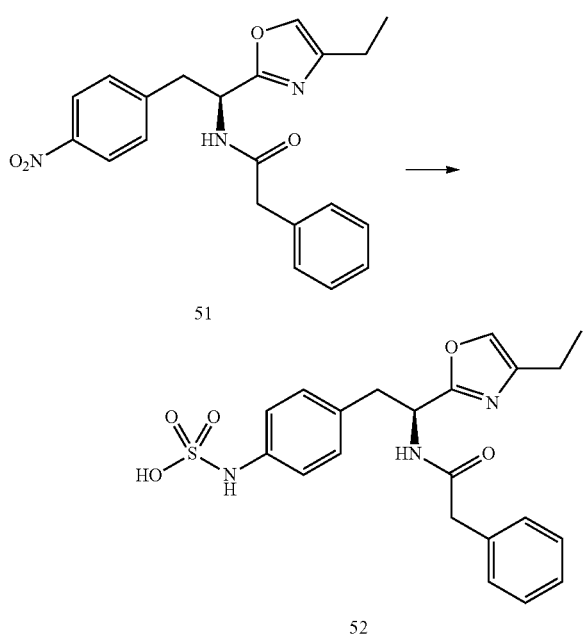

Reagents and conditions: (b) C₆H₄CO₂H, EDCI, HOBt, DIPEA, DMF; rt, 18 hr.

Reagents and conditions: (c) (i) H₂:Pd/C, MeOH; (ii) SO₃-pyridine, NH₄OH, rt, 18 hr.

Example 17

{4-[2-(S)-(4-Ethyloxazol-2-yl)-2-phenylacetylaminoethyl]-phenyl}sulfamic acid (52)

Preparation of (S)-1-(4-ethyloxazol-2-yl)-2-(4-nitrophenyl)ethanamine (50): A mixture of [1-(S)-carbamoyl-2-(4-nitrophenyl)ethyl-carbamic acid tert-butyl ester, 1, (10 g, 32.3 mmol) and 1-bromo-2-butanone (90%, 4.1 mL, 36 mmol) in CH₃CN (500 mL) is refluxed for 18 hours. The reaction mixture is cooled to room temperature and diethyl ether is added to the solution and the precipitate which forms is removed by filtration and is used without further purification.

Preparation of N-[1-(4-ethyloxazol-2-yl)-2-(4-nitrophenyl)ethyl]-2-phenyl-acetamide (51): To a solution of (S)-1-(4-ethyloxazol-2-yl)-2-(4-nitrophenyl)ethanamine, 50, (2.9 g, 11 mmol), phenylacetic acid (1.90 g, 14 mmol) and 1-hydroxybenzotriazole (HOBt) (0.94 g, 7.0 mmol) in DMF (100 mL) at 0° C., is added 1-(3-dimethylamino-propyl)-3-ethyl-carbodiimide (EDCI) (2.68 g, 14 mmol) followed by triethylamine (6.0 mL, 42 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of {4-[2-(S)-(4-ethyloxazol-2-yl)-2-phenylacetylaminoethyl]-phenyl}sulfamic acid (52): N-[1-(4-ethyloxazol-2-yl)-2-(4-nitrophenyl)ethyl]-2-phenyl-acetamide, 51, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.177 g, 1.23). The reaction is stirred at room temperature for 5 minutes after which a 7% solution of NH₄OH (10 mL) is added. The mixture is then concentrated and the resulting residue is purified by reverse phase chromatography to afford the desired product as the ammonium salt.

Regulation of HPTP-β provides a method for modulating the activity of angiopoietin receptor-type tyrosine kinase Tie-2, and thereby mediate, affect, or otherwise control disease states related to angiogenesis wherein angiogenesis is improperly regulated by the human body. The compounds of the present disclosure serve as a method for providing regulation of angiogenesis. As such the present disclosure addresses several unmet medical needs, inter alia;

1) Providing compositions effective as human protein tyrosine phosphatase beta (HPTP-β) inhibitors; and thereby providing a method for regulating angiogenesis in a disorder wherein angiogenesis is elevated;
2) Providing compositions effective as human protein tyrosine phosphatase beta (HPTP-β) inhibitors; and thereby providing a method for regulating angiogenesis in a disorder; and
3) Providing compositions effective human protein tyrosine phosphatase beta (HPTP-β) inhibitors; and thereby providing a method for regulating angiogenesis in a disorder wherein angiogenesis is decreased.

For purposes of the present disclosure the term "regulate" is defined as including, but is not limited to, up-regulate or down-regulate, to fix, to bring order or uniformity, to govern, or to direct by various means. In one aspect, an antibody may be used in a method for the treatment of an "angiogenesis elevated disorder" or "angiogenesis reduced disorder". As used herein, an "angiogenesis elevated disorder" is one that involves unwanted or elevated angiogenesis in the biological manifestation of the disease, disorder, and/or condition; in the biological cascade leading to the disorder; or as a symptom of the disorder. Similarly, the "angiogenesis reduced disorder" is one that involves wanted or reduced angiogenesis in the biological manifestations. This "involvement" of angiogenesis in an angiogenesis elevated/reduced disorder includes, but is not limited to, the following:
1. The angiogenesis as a "cause" of the disorder or biological manifestation, whether the level of angiogenesis is elevated or reduced genetically, by infection, by autoimmunity, trauma, biomechanical causes, lifestyle, or by some other causes.
2. The angiogenesis as part of the observable manifestation of the disease or disorder. That is, the disease or disorder is measurable in terms of the increased or reduced angiogenesis. From a clinical standpoint, angiogenesis indicates the disease; however, angiogenesis need not be the "hallmark" of the disease or disorder.
3. The angiogenesis is part of the biochemical or cellular cascade that results in the disease or disorder. In this respect, regulation of angiogenesis may interrupt the cascade, and may control the disease. Non-limiting examples of angiogenesis regulated disorders that may be treated by the present disclosure are herein described below.

Formulations

The present disclosure also relates to compositions or formulations that comprise one or more human protein tyrosine phosphatase beta (HPTP-β) inhibitors as disclosed herein. In general, the disclosed compositions comprise:
a) an effective amount of one or more phenylsufamic acids or salts thereof according to the present disclosure that are effective as human protein tyrosine phosphatase beta (HPTP-β) inhibitors; and
b) one or more excipients.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

Non-limiting examples of disclosed compositions include:
a) from about 0.001 mg to about 1000 mg of one or more phenylsulfamic acids or salts thereof according to the present disclosure; and
b) one or more excipients.

Another example of disclosed compositions includes:
a) from about 0.01 mg to about 100 mg of one or more phenylsulfamic acids or salts thereof according to the present disclosure; and
b) one or more excipients.

A further example of disclosed compositions includes:
a) from about 0.1 mg to about 10 mg of one or more phenylsulfamic acids or salts thereof according to the present disclosure; and
b) one or more excipients.

The term "effective amount" as used herein means "an amount of one or more phenylsulfamic acids, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. Thus, it is not possible to specify an exact "effective amount." For example, several divided doses may be administered daily or the dose may be proportionally reduced as indicated by the exigencies of the therapeutic situation. In addition, the compositions of the present disclosure can be administered as frequently as necessary to achieve a therapeutic amount.

Method of Use

The present disclosure relates to methods for regulating angiogenesis in a human comprising administering to a human one or more of the disclosed compounds.

One example of the disclosed methods includes a method for treating an angiogenesis regulated disorder in a subject, wherein the angiogenesis regulated disorder is an angiogenesis elevated disorder, and said disorder is chosen from diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma and post-laser complications, diseases associated with rubeosis, and proliferative vitreoretinopathy.

Another example of the disclosed methods includes a method for treating an angiogenesis regulated disorder in a subject, wherein the angiogenesis regulated disorder is an angiogenesis elevated disorder, and said disorder is chosen from inflammatory bowel diseases such as Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors and acquired immune deficiency syndrome.

A further example of the disclosed methods includes a method for treating an angiogenesis regulated disorder in a subject wherein the angiogenesis regulated disorder is an angiogenesis reduced disorder and chosen from skeletal muscle and myocardial ischemia, stroke, coronary artery disease, peripheral vascular disease, coronary artery disease.

A yet further example of the disclosed methods includes a method of vascularizing ischemic tissue. As used herein, "ischemic tissue," means tissue that is deprived of adequate blood flow. Examples of ischemic tissue include, but are not limited to, tissue that lack adequate blood supply resulting from myocardial and cerebral infarctions, mesenteric or limb ischemia, or the result of a vascular occlusion or stenosis. In one example, the interruption of the supply of oxygenated blood may be caused by a vascular occlusion. Such vascular occlusion may be caused by arteriosclerosis, trauma, surgical procedures, disease, and/or other etiologies. Also included within the methods of treatment of the present disclosure is the treatment of skeletal muscle and myocardial ischemia, stroke, coronary artery disease, peripheral vascular disease, coronary artery disease.

A still further example of the disclosed methods includes a method of repairing tissue. As used herein, "repairing tissue"

means promoting tissue repair, regeneration, growth, and/or maintenance including, but not limited to, wound repair or tissue engineering. One skilled in the art appreciates that new blood vessel formation is required for tissue repair. In turn, tissue may be damaged by, including, but not limited to, traumatic injuries or conditions including arthritis, osteoporosis and other skeletal disorders, and burns. Tissue may also be damaged by injuries due to surgical procedures, irradiation, laceration, toxic chemicals, viral infection or bacterial infections, or burns. Tissue in need of repair also includes non-healing wounds. Examples of non-healing wounds include non-healing skin ulcers resulting from diabetic pathology; or fractures that do not heal readily.

The disclosed compounds are also suitable for use in effecting tissue repair in the context of guided tissue regeneration (GTR) procedures. Such procedures are currently used by those skilled in the arts to accelerate wound healing following invasive surgical procedures.

A yet still further example of the disclosed methods includes a method of promoting tissue repair characterized by enhanced tissue growth during the process of tissue engineering. As used herein, "tissue engineering" is defined as the creation, design, and fabrication of biological prosthetic devices, in combination with synthetic or natural materials, for the augmentation or replacement of body tissues and organs. Thus, the present methods may be used to augment the design and growth of human tissues outside the body for later implantation in the repair or replacement of diseased tissues. For example, antibodies may be useful in promoting the growth of skin graft replacements that are used as a therapy in the treatment of burns.

Other examples of the tissue engineering example of the disclosed methods includes in cell-containing or cell-free devices that induce the regeneration of functional human tissues when implanted at a site that requires regeneration. As discussed herein, biomaterial-guided tissue regeneration may be used to promote bone re-growth in, for example, periodontal disease. Thus, antibodies may be used to promote the growth of reconstituted tissues assembled into three-dimensional configurations at the site of a wound or other tissue in need of such repair.

A yet further example of the tissue engineering example of the disclosed methods, the compounds disclosed herein can be included in external or internal devices containing human tissues designed to replace the function of diseased internal tissues. This approach involves isolating cells from the body, placing them with structural matrices, and implanting the new system inside the body or using the system outside the body. For example, antibodies may be included in a cell-lined vascular graft to promote the growth of the cells contained in the graft. It is envisioned that the methods of the disclosure may be used to augment tissue repair, regeneration and engineering in products such as cartilage and bone, central nervous system tissues, muscle, liver, and pancreatic islet (insulin-producing) cells.

The present disclosure also relates to the use of the disclosed phenylsulfamic acids in the manufacture of a medicament for promoting the growth of skin graft replacements.

The present disclosure also relates to the use of the disclosed phenylsulfamic acids according to the present disclosure in the manufacture of a medicament for use in effecting tissue repair in the context of guided tissue regeneration (GTR) procedures.

The disclosed compounds can be used in the manufacture of one or more medicaments, non-limiting examples of these medicaments are:

Medicaments for the treatment an angiogenesis regulated disorder in a subject, wherein the angiogenesis regulated disorder is an angiogenesis elevated disorder.

Medicaments for the treatment an angiogenesis regulated disorder in a subject, wherein the angiogenesis regulated disorder is an angiogenesis elevated disorder chosen from Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors and acquired immune deficiency syndrome.

Medicaments useful for the purposes of tissue engineering thereby inducing enhanced tissue growth.

Medicaments for the treatment an angiogenesis regulated disorder in a subject, wherein the angiogenesis regulated disorder is an angiogenesis reduced disorder.

Procedures

Screening Assays Using In Vitro and In Vivo Models of Angiogenesis

Antibodies of the disclosed compounds may be screened in angiogenesis assays that are known in the art. Such assays include in vitro assays that measure surrogates of blood vessel growth in cultured cells or formation of vascular structures from tissue explants and in vivo assays that measure blood vessel growth directly or indirectly (Auerbach, R., et al. (2003). Clin Chem 49, 32-40, Vailhe, B., et al. (2001). Lab Invest 81, 439-452).

1. In Vitro Models of Angiogenesis

The in vitro models which are suitable for use in the present disclosure employ cultured endothelial cells or tissue explants and measure the effect of agents on "angiogenic" cell responses or on the formation of blood capillary-like structures. Non-limiting examples of in vitro angiogenesis assays include but are not limited to endothelial cell migration and proliferation, capillary tube formation, endothelial sprouting, the aortic ring explant assay and the chick aortic arch assay.

2. In Vivo Models of Angiogenesis

The in vivo agents or antibodies which are suitable for use in the present disclosure are administered locally or systemically in the presence or absence of growth factors (i.e. VEGF or angiopoietin 1) and new blood vessel growth is measured by direct observation or by measuring a surrogate marker such as hemoglobin content or a fluorescent indicator. Non-limiting examples of in vitro angiogenesis assays include but are not limited to chick chorioallantoic membrane assay, the corneal angiogenesis assay, and the MATRIGEL™ plug assay.

3. Procedures for Determining Vascularization of Ischemic Tissue.

Standard routine techniques are available to determine if a tissue is at risk of suffering ischemic damage from undesirable vascular occlusion. For example, in myocardial disease these methods include a variety of imaging techniques (e.g., radiotracer methodologies, x-ray, and MRI) and physiological tests. Therefore, induction of angiogenesis as an effective means of preventing or attenuating ischemia in tissues affected by or at risk of being affected by a vascular occlusion can be readily determined A person skilled in the art of using standard techniques can measure the vascularization of tissue. Non-limiting examples of measuring vascularization in a subject include SPECT (single photon emission computed tomography); PET (positron emission tomography); MRI (magnetic resonance imaging); and combination thereof, by measuring blood flow to tissue before and after treatment. Angiography may be used as an assessment of macroscopic vascularity. Histologic evaluation may be used to quantify vascularity at the small vessel level. These and other techniques are discussed in Simons, et al., "Clinical trials in coronary angiogenesis," *Circulation,* 102, 73-86 (2000).

The following are non-limiting examples of HPTPβ (IC$_{50}$ μM) and PTP1B (IC$_{50}$ μM) activity is listed herein below in Table A.

TABLE A

| Compound | HPTPβ IC$_{50}$ μM | PTP1B IC$_{50}$ μM |
|---|---|---|
| 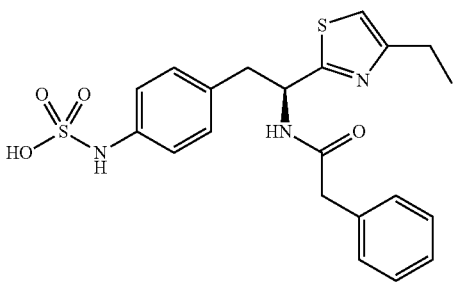<br>(S)-{4-[2-(4-Ethylthiazol-2-yl)-2-(phenylacetylamido)ethyl]-phenyl}sulfamic acid | 0.05 | 22.9 |
| 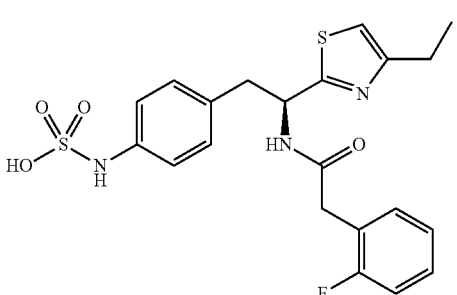<br>(S)-4-(2-(4-Ethylthiazol-2-yl)-2-(2-(2-fluorophenyl)acetamido)ethyl)phenyl-sulfamic acid | 0.012 | 5.36 |
| 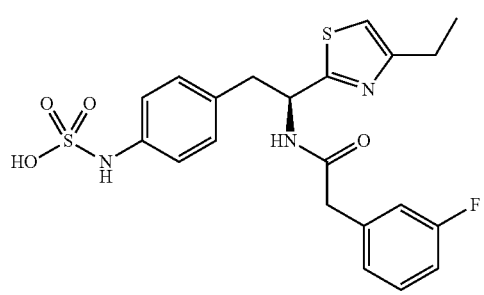<br>(S)-4-(2-(4-Ethylthiazol-2-yl)-2-(2-(3-fluorophenyl)acetamido)ethyl)phenyl-sulfamic acid | 0.0003 | 2.85 |
| 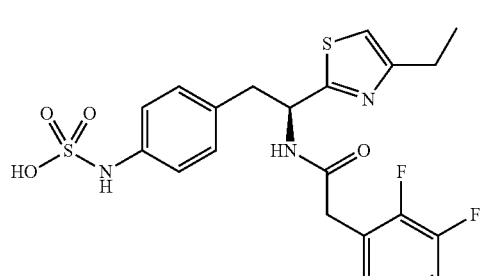<br>(S)-4-(2-(2-(2,3-Difluorophenyl)acetamido)-2-(4-ethylthiazol-2-yl)ethyl)phenyl-sulfamic acid | 0.028 | 5.36 |

TABLE A-continued
| Compound | HPTPβ IC$_{50}$ μM | PTP1B IC$_{50}$ μM |
|---|---|---|
| 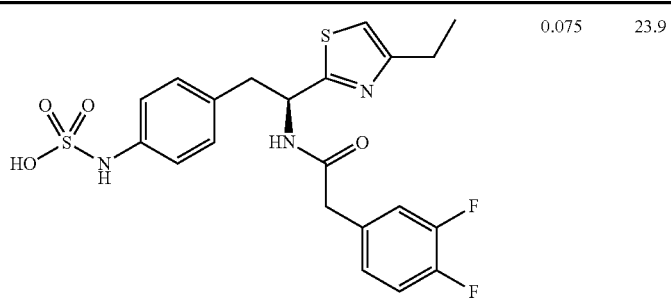<br>(S)-4-(2-(2-(3,4-Difluorophenyl)acetamido)-2-(4-ethylthiazol-2-yl)ethyl)phenyl-sulfamic acid | 0.075 | 23.9 |
| 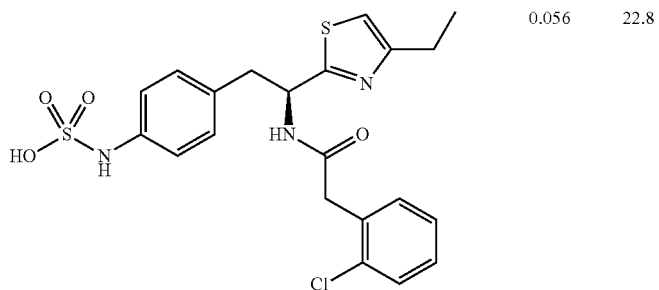<br>(S)-4-(2-(2-(2-Chlorophenyl)acetamido)-2-(4-ethylthiazol-2-yl)ethyl)phenyl-sulfamic acid | 0.056 | 22.8 |
| 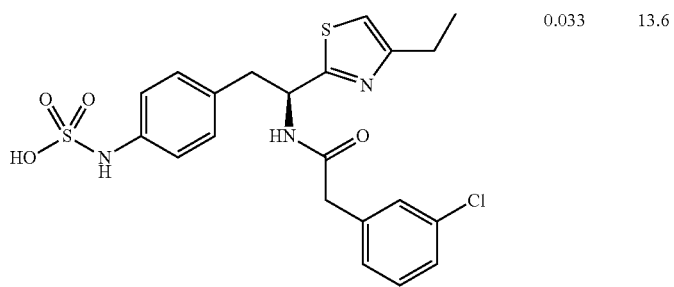<br>(S)-4-(2-(2-(3-Chlorophenyl)acetamido)-2-(4-ethylthiazol-2-yl)ethyl)phenyl-sulfamic acid | 0.033 | 13.6 |
| 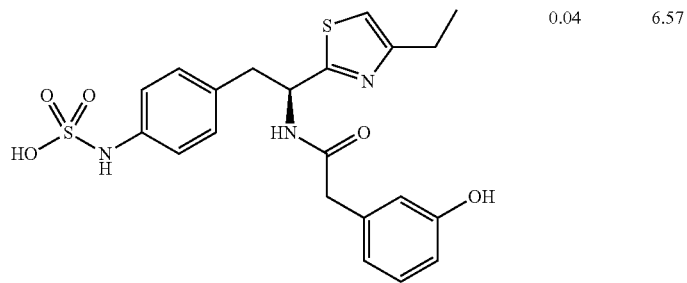<br>(S)-4-(2-(4-Ethylthiazol-2-yl)-2-(2-(3-hydroxyphenyl)acetamido)ethyl)phenyl-sulfamic acid | 0.04 | 6.57 |

TABLE A-continued
| Compound | HPTPβ IC$_{50}$ μM | PTP1B IC$_{50}$ μM |
|---|---|---|
| 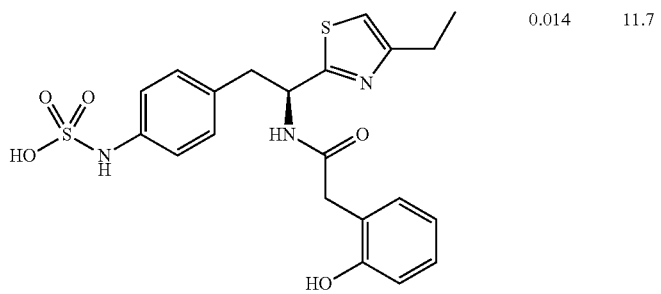<br>(S)-4-(2-(4-Ethylthiazol-2-yl)-2-(2-(2-methoxyphenyl)acetamido)ethyl)phenyl-sulfamic acid | 0.014 | 11.7 |
| 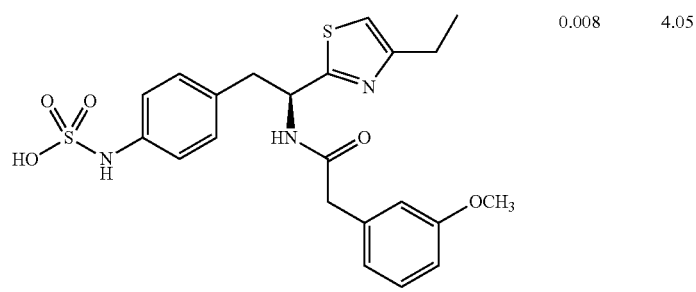<br>(S)-4-(2-(4-Ethylthiazol-2-yl)-2-(2-(3-methoxyphenyl)acetamido)ethyl)phenyl-sulfamic acid | 0.008 | 4.05 |
| 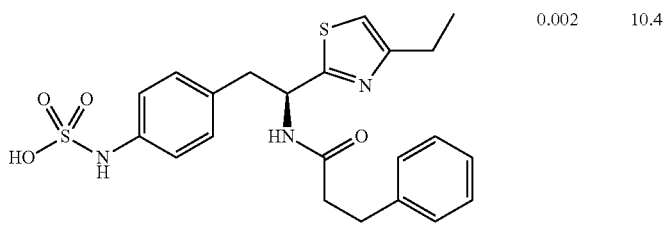<br>(S)-4-(2-(4-Ethylthiazol-2-yl)-2-(3-phenylpropanamido)ethyl)phenylsulfamic acid | 0.002 | 10.4 |
| 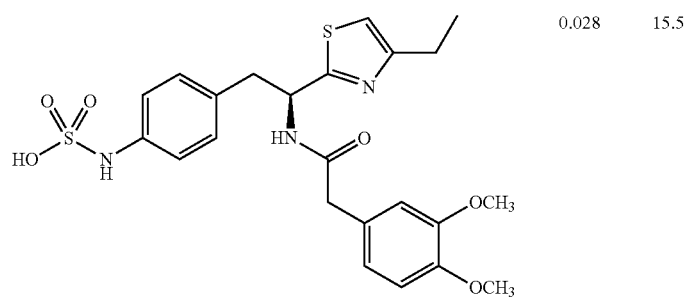<br>(S)-4-(2-(2-(3,4-Dimethoxyphenyl)acetamido)-2-(4-ethylthiazol-2-yl)ethyl)-phenylsulfamic acid | 0.028 | 15.5 |

TABLE A-continued

| Compound | HPTPβ IC$_{50}$ μM | PTP1B IC$_{50}$ μM |
|---|---|---|
| 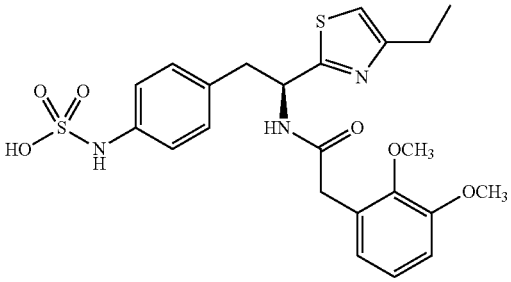<br>(S)-4-(2-(2-(2,3-Dimethoxyphenyl)acetamido)-2-(4-ethylthiazol-2-yl)ethyl)-phenylsulfamic acid | 0.037 | 25.4 |
| 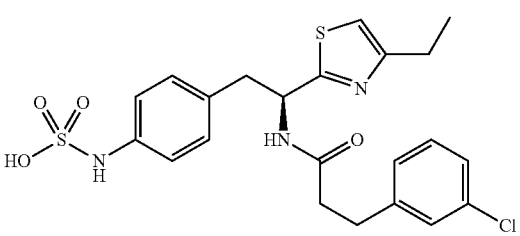<br>(S)-4-(2-(3-(3-Chlorophenyl)propanamido)-2-(4-ethylthiazol-2-yl)ethyl)phenyl-sulfamic acid | 0.0002 | 15.3 |
| 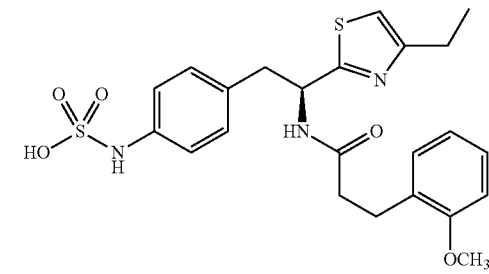<br>(S)-4-(2-(4-Ethylthiazol-2-yl)-2-(3-(2-methoxyphenyl)propanamido)ethyl)phenyl-sulfamic acid | 0.003 | 16.9 |
| 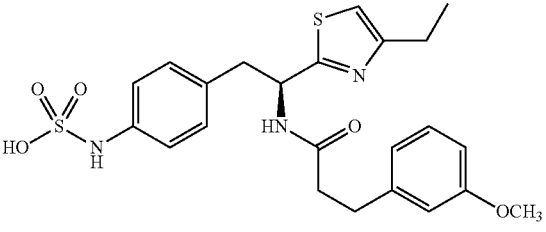<br>(S)-4-(2-(4-Ethylthiazol-2-yl)-2-(3-(3-methoxyphenyl)propanamido)ethyl)phenyl-sulfamic acid | 0.01 | 20.6 |
| 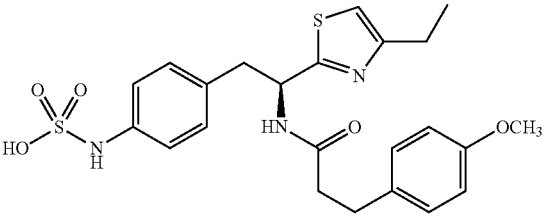<br>(S)-4-(2-(4-Ethylthiazol-2-yl)-2-(3-(4-methoxyphenyl)propanamido)ethyl)phenyl-sulfamic acid | 0.006 | 16.0 |

TABLE A-continued

| Compound | HPTPβ IC$_{50}$ μM | PTP1B IC$_{50}$ μM |
| --- | --- | --- |
| (S)-4-{2-[2-(4-Ethyl-2,3-dioxopiperazin-1-yl)acetamide]-2-(4-ethylthiazol-2-yl)ethyl}phenylsulfamic acid | 0.002 | 0.53 |
| (S)-4-{2-(4-Ethylthiazol-2-yl)-2-[2-(5-methyl-2,4-dioxo-3,4-dihydropyrimidin-1(2H)-yl)acetamide]ethyl}phenylsulfamic acid | 0.002 | 0.254 |
| (S)-4-[2-(Benzo[d][1,3]dioxole-5-carboxamido)-2-(4-ethylthiazol-2-yl)ethyl]phenylsulfamic acid | 0.042 | 19 |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A compound having the formula:

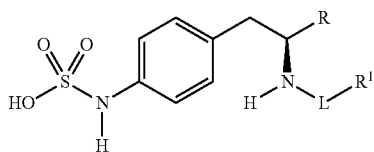

wherein R is a substituted or unsubstituted thiazolyl unit having the formula:

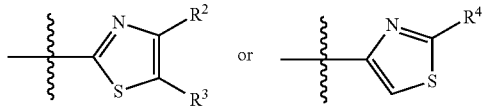

$R^2$ and $R^3$ are each independently chosen from:
i) hydrogen; or
ii) substituted or unsubstituted $C_1$-$C_6$ linear, $C_3$-$C_6$ branched, or $C_3$-$C_6$ cyclic alkyl;

$R^4$ is a unit chosen from:
i) hydrogen; or
ii) substituted or unsubstituted $C_1$-$C_6$ linear, $C_3$-$C_6$ branched, or $C_3$-$C_6$ cyclic alkyl;

$R^1$ is substituted or unsubstituted phenyl, said substitutions are independently chosen from one or more halogen, $C_1$-$C_6$ linear, $C_3$-$C_6$ branched, or $C_3$-$C_6$ cyclic alkyl, —$OR^{11}$, —CN, —$N(R^{11})_2$, —$CO_2R^{11}$, —C(O)N$(R^{11})_2$, —$NR^{11}$C(O)$R^{11}$, —$NO_2$, —$SO_2R^{11}$, phenyl, benzyl, or two substitutions can be taken together to form a cycloalkyl, heterocyclic, or heteroaryl ring comprising from 3-7 atoms, said rings comprising one or more heteroatoms chosen from oxygen, nitrogen, or sulfur; each $R^{11}$ is independently hydrogen; substituted or unsubstituted $C_1$-$C_4$ linear, $C_3$-$C_4$ branched, $C_3$-$C_4$ cyclic alkyl or substituted or unsubstituted phenyl or benzyl; or when $R^1$ is substituted by phenyl or benzyl, said phenyl or benzyl can be further substituted by halogen, $C_1$-$C_3$ linear alkyl, $C_1$-$C_3$ linear alkoxy, —$CO_2R^{11}$ and —$NHCOR^{16}$; each $R^{16}$ is independently hydrogen, methyl, or ethyl;

L has the formula:

—C(O)[C($R^{6a}R^{6b}$)]$_x$—;

$R^{6a}$ and $R^{6b}$ are each independently:
i) hydrogen; or
ii) $C_1$-$C_4$ linear or $C_3$-$C_4$ branched alkyl;
the index x is from 0 to 4; or
a pharmaceutically acceptable salt thereof.

2. The compound according to claim 1, wherein the compounds are salts comprising cations chosen from ammonium, sodium, lithium, potassium, calcium, magnesium, and bismuth.

3. The compound according to claim 1, wherein R has the formula:

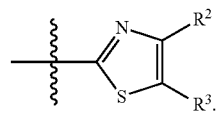

4. The compound according to claim 3, wherein $R^2$ and $R^3$ are each hydrogen or substituted or unsubstituted $C_1$-$C_6$ linear, $C_3$-$C_6$ branched, or $C_3$-$C_6$ cyclic alkyl.

5. The compound according to claim 3, wherein $R^2$ is methyl and $R^3$ is hydrogen.

6. The compound according to claim 1, wherein $R^1$ is chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl.

7. The compound according to claim 1, wherein L has the formula —C(O)CH$_2$—.

8. The compound according to claim 1, wherein L has the formula —C(O)CH$_2$CH$_2$—.

9. A compound having the formula:

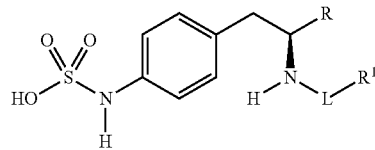

wherein R is a substituted or unsubstituted thiazolyl unit having the formula:

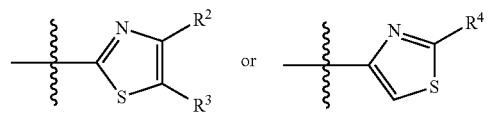

$R^2$ and $R^3$ are each independently chosen from:
i) hydrogen; or
ii) substituted or unsubstituted $C_1$-$C_6$ linear, $C_3$-$C_6$ branched, or $C_3$-$C_6$ cyclic alkyl;

$R^4$ is a unit chosen from:
i) hydrogen;
ii) substituted or unsubstituted $C_1$-$C_6$ linear, $C_3$-$C_6$ branched, or $C_3$-$C_6$ cyclic alkyl; or
iii) 5-member or 6-member heteroaryl, wherein the heteroaryl ring contains one or more heteroatoms chosen from oxygen, nitrogen, or sulfur;

$R^1$ is chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted phenyl; or
iv) substituted or unsubstituted 5-member or 6-member heteroaryl, wherein the heteroaryl ring contains one or more heteroatoms chosen from oxygen, nitrogen, or sulfur;

said substitutions are independently chosen from one or more halogen, $C_1$-$C_6$ linear, $C_3$-$C_6$ branched, or $C_3$-$C_6$ cyclic alkyl, —OR$^{11}$, —CN, —N(R$^{11}$)$_2$, —CO$_2$R$^{11}$, —C(O)N(R$^{11}$)$_2$, —NR$^{11}$C(O)R$^{11}$, —NO$_2$, —SO$_2$R$^{11}$, phenyl, benzyl, or two substitutions can be taken together to form a cycloalkyl, heterocyclic, or heteroaryl ring comprising from 3-7 atoms, said rings comprising one or more heteroatoms chosen from oxygen, nitrogen, or sulfur; each R$^{11}$ is independently hydrogen; substituted or unsubstituted C$_1$-C$_4$ linear, C$_3$-C$_4$ branched, C$_3$-C$_4$ cyclic alkyl or substituted or unsubstituted phenyl or benzyl; or when R$^1$ is substituted by phenyl or benzyl, said phenyl or benzyl can be further substituted by halogen, C$_1$-C$_3$ linear alkyl, C$_1$-C$_3$ linear alkoxy, —CO$_2$R$^{11}$ and —NHCOR$^{16}$; each R$^{16}$ is independently hydrogen, methyl, or ethyl;

L has the formula:

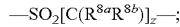

—SO$_2$[C(R$^{8a}$R$^{8b}$)]$_x$—;

R$^{8a}$ and R$^{8b}$ are each independently:
i) hydrogen; or
ii) C$_1$-C$_4$ linear or C$_3$-C$_4$ branched alkyl;
the index x is from 0 to 4; or
a pharmaceutically acceptable salt thereof.

10. The compound according to claim 9, wherein L is chosen from:
i) —SO$_2$CH$_2$—;
i) —SO$_2$CH$_2$CH$_2$—; or
i) —SO$_2$CH$_2$CH$_2$CH$_2$—.

11. The compound according to claim 9, wherein R$^4$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

12. The compound according to claim 9, wherein R$^4$ is thiophen-2-yl or thiophen-3-yl.

13. The compound according to claim 9, wherein R$^1$ is substituted or unsubstituted C$_1$-C$_6$ linear, C$_3$-C$_6$ branched, or C$_3$-C$_6$ cyclic alkyl.

14. The compound according to claim 9, wherein R$^1$ is substituted or unsubstituted phenyl.

15. The compound according to claim 9, wherein R$^1$ is substituted or unsubstituted 5-member or 6-member heteroaryl.

16. A compound having the formula:

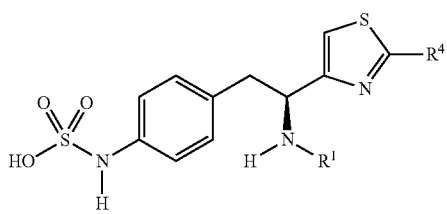

wherein R$^4$ is chosen from:
i) hydrogen;
ii) substituted or unsubstituted C$_1$-C$_6$ linear, C$_3$-C$_6$ branched, or C$_3$-C$_6$ cyclic alkyl;
iii) substituted or unsubstituted phenyl; or
iv) substituted or unsubstituted 5-member or 6-member heteroaryl, wherein the heteroaryl ring contains one or more heteroatoms chosen from oxygen, nitrogen, or sulfur;

R$^1$ is substituted or unsubstituted 5-member or 6-member heteroaryl, wherein the heteroaryl ring contains one or more heteroatoms chosen from oxygen, nitrogen, or sulfur; said substitutions are independently chosen from one or more halogen, C$_1$-C$_6$ linear, C$_3$-C$_6$ branched, or C$_3$-C$_6$ cyclic alkyl, —OR$^{11}$, —CN, —N(R$^{11}$)$_2$, —CO$_2$R$^{11}$, —C(O)N(R$^{11}$)$_2$, —NR$^{11}$C(O)R$^{11}$, —NO$_2$, —SO$_2$R$^{11}$, phenyl, benzyl, or two substitutions can be taken together to form a cycloalkyl, heterocyclic, or heteroaryl ring comprising from 3-7 atoms, said rings comprising one or more heteroatoms chosen from oxygen, nitrogen, or sulfur; each R$^{11}$ is independently hydrogen; substituted or unsubstituted C$_1$-C$_4$ linear, C$_3$-C$_4$ branched, C$_3$-C$_4$ cyclic alkyl or substituted or unsubstituted phenyl or benzyl; or when R$^1$ is substituted by phenyl or benzyl, said phenyl or benzyl can be further substituted by halogen, C$_1$-C$_3$ linear alkyl, C$_1$-C$_3$ linear alkoxy, —CO$_2$R$^{11}$ and —NHCOR$^{16}$; each R$^{16}$ is independently hydrogen, methyl, or ethyl.

17. The compound according to claim 16, wherein R$^1$ is chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

18. The compound according to claim 16, wherein R$^1$ is a phenyl or benzyl substituted 5-member or 6-member heteroaryl, wherein the heteroaryl ring contains one or more heteroatoms chosen from oxygen, nitrogen, or sulfur; wherein the phenyl ring or benzyl aryl ring can be further substituted with halogen, C$_1$-C$_3$ linear alkyl, C$_1$-C$_3$ linear alkoxy, —CO$_2$R$^{11}$ and —NHCOR$^{16}$; each R$^{16}$ is independently hydrogen, methyl, or ethyl.

19. The compound according to claim 16, wherein R$^4$ is substituted or unsubstituted C$_1$-C$_6$ linear, C$_3$-C$_6$ branched, or C$_3$-C$_6$ cyclic alkyl.

20. The compound according to claim 16, wherein R$^1$ is [1,3,4]thiadiazol-2-yl substituted with methyl, ethyl, propyl, benzyl, 3-methoxybenzyl, naphthalen-1-ylmethyl, (methoxycarbonyl)methyl, or (2-methylthiazol-4-yl)methyl.

\* \* \* \* \*